(12) United States Patent
Liu et al.

(10) Patent No.: US 11,286,304 B2
(45) Date of Patent: Mar. 29, 2022

(54) ANTI-GALECTIN-7 ANTIBODY, KIT COMPRISING THE SAME, AND USES THEREOF

(71) Applicant: Academia Sinica, Taipei (TW)

(72) Inventors: Fu-Tong Liu, Taipei (TW); Hung-Lin Chen, Taipei (TW); Po-Cheng Chiang, Taipei (TW)

(73) Assignee: ACADEMIA SINICA, Taipei (TW)

( * ) Notice: Subject to any disclaimer, the term of this patent is extended or adjusted under 35 U.S.C. 154(b) by 226 days.

(21) Appl. No.: 16/653,986

(22) Filed: Oct. 15, 2019

(65) Prior Publication Data
US 2020/0115456 A1 Apr. 16, 2020

Related U.S. Application Data

(60) Provisional application No. 62/745,484, filed on Oct. 15, 2018.

(51) Int. Cl.
*C07K 16/28* (2006.01)
*G01N 33/50* (2006.01)
*A61P 17/06* (2006.01)
*A61P 35/00* (2006.01)

(52) U.S. Cl.
CPC .......... *C07K 16/2851* (2013.01); *A61P 17/06* (2018.01); *A61P 35/00* (2018.01); *G01N 33/5011* (2013.01); *G01N 33/5023* (2013.01); *G01N 33/5044* (2013.01); *C07K 2317/56* (2013.01); *G01N 2333/705* (2013.01)

(58) Field of Classification Search
None
See application file for complete search history.

*Primary Examiner* — Nora M Rooney

(57) ABSTRACT

Provided herein is a novel antibody exhibiting binding affinity and specificity to galectin-7. Also provided herein are methods for treating psoriasis or cancer in a subject by administering to the subject a drug selected with the aid of the present anti-galectin-7 antibody.

18 Claims, 41 Drawing Sheets

Specification includes a Sequence Listing.

ANTI-GALECTIN-7 ANTIBODY, KIT COMPRISING THE SAME, AND USES THEREOF

CROSS-REFERENCE OF RELATED APPLICATION

This application claims priority to US. Application No. 62/745,484, filed on Oct. 15, 2018. The content of which application is incorporated herein by reference in its entirety.

BACKGROUND OF THE INVENTION

1. Field of the Invention

The present disclosure in general relates to the field of psoriasis and cancer treatment. More particularly, the present disclosure relates to a novel antibody, and the uses thereof as a platform for selecting a drug candidate to treat psoriasis or cancer.

2. Description of Related Art

Galectins are a family of beta-galactoside-binding proteins implicated in modulating cell-cell and cell-matrix interactions. Completion of the human, mouse and rat genome sequences reveal about 15 galectins and galectin-like proteins in one mammalian genome with slight variation between species. Strong evidence suggests roles for galectins in the pathogenesis of a spectrum of diseases, particularly diseases involving inflammation or cancers. For example, galectin-3 is now an established histochemical marker of thyroid cancer; galectin-1 is frequently found to be over-expressed in low differentiated cancer cells; and galectin-9 or its relatives galectin-4 and galectin-8 may be induced in specific cancer types.

Human galectin-7 encoded by LGALS7 gene is found in many tissues such as cerebral cortex, colon, liver, kidney, testis, skin and lymph nodes, with skin having the highest expressed level of galectin-7. Accordingly, human galectin-7 has been highlighted as an important marker for the pathogeneses of various diseases in these tissues.

In view of the forgoing, there exists a need for a novel drug for efficiently and safely treating diseases and/or disorders associated with the expression of galectin-7.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

The present disclosure aims at providing a platform for selecting a drug candidate for the treatment of psoriasis or other diseases such as cancer caused by and/or associated with abnormal expression of galectin-7. As embodied and broadly described herein, one aspect of the disclosure is thus directed to an antibody or a fragment thereof serving as the drug candidate-selecting platform. The antibody comprises a heavy chain variable (VH) region and a light chain variable (VL) region, in which the VH region comprises a first heavy chain complementarity determining region (CDR-H1), a second heavy chain CDR (CDR-H2), and a third heavy chain CDR (CDR-H3); and the VL region comprises a first light chain CDR (CDR-L1), a second light chain CDR (CDR-L2), and a third light chain CDR (CDR-L3).

According to embodiments of the present disclosure, the CDR-H1, CDR-H2 and CDR-H3 respectively comprise the amino acid sequences of SEQ ID NOs: 1, 2 and 3, and the CDR-L1, CDR-L2 and CDR-L3 respectively comprise the amino acid sequences of SEQ ID NOs: 4, 5 and 6.

In certain embodiments, the heavy chain variable region is at least 85% identical to SEQ ID NO: 7, and the light chain variable region is at least 85% identical to SEQ ID NO: 8. Preferably, the heavy chain variable region is at least 90% identical to SEQ ID NO: 7, and the light chain variable region is at least 90% identical to SEQ ID NO: 8. More preferably, the heavy chain variable region is at least 95% identical to SEQ ID NO: 7, and the light chain variable region is at least 95% identical to SEQ ID NO: 8. According to one working example, the heavy chain variable region has the amino acid sequence of SEQ ID NO: 7, and the light chain variable region has the amino acid sequence of SEQ ID NO: 8.

Also disclosed herein is a kit for selecting a drug candidate suitable for treating a galectin-7 associated disease. The kit comprises the antibody of the present disclosure, and a pharmaceutically acceptable carrier.

The galectin-7 associated disease may be a cancer, inflammatory disease, or allergy. According to certain embodiments of the present disclosure, the galectin-7 associated disease is psoriasis. According to other embodiments of the present disclosure, the galectin-7 associated disease is cancer.

Another aspect of the present disclosure pertains to a method of selecting a drug candidate suitable for treating psoriasis or cancer. According to embodiments of the present disclosure, the method comprises the steps of, (a) incubating keratinocytes with one or more candidate drugs;

(b) determining the expression level of galectin-7 in the keratinocytes of step (a) by use of the present antibody or kit; and (c) selecting the drug candidate from the one or more candidate drugs based on the expression level determined in step (b), wherein the drug candidate increases the expression level of galectin-7.

According to some embodiments, the selected drug candidate is a statin. In the preferred example, in the case when the subject has the psoriasis, the statin is fluvastatin, atorvastatin, cerivastatin, pitavastatin, or simvastatin; while in the case when the subject has the cancer, the statin is fluvastatin, atorvastatin, cerivastatin, pitavastatin, simvastatin, lovastatin, mevastatin, pravastatin, or rosuvastatin.

Another aspect of the present disclosure is directed to a pharmaceutical composition and the uses thereof in the treatment of psoriasis or cancer.

Another aspect of the present disclosure is directed to a method of treating psoriasis or cancer in a subject, comprising: (1) selecting a drug candidate suitable for treating the psoriasis or the cancer by, (1a) incubating keratinocytes with one or more candidate drugs;

(1b) determining the expression level of galectin-7 in the keratinocytes of step (1a) by use of the present antibody or kit; and (1c) selecting the drug candidate from the one or more candidate drugs based on the expression level determined in step (1b), wherein the drug candidate increases the expression level of galectin-7; and (2) treating the subject by administering to the subject an effective amount of a pharmaceutical composition, which comprises the selected drug candidate in the step (1c); and a pharmaceutically acceptable carrier.

According to some embodiments, the selected drug candidate in the step (1c) is a statin. In the preferred example, in the case when the subject has the psoriasis, the statin is fluvastatin, atorvastatin, cerivastatin, pitavastatin, or simvastatin; while in the case when the subject has the cancer, the statin is fluvastatin, atorvastatin, cerivastatin, pitavastatin, simvastatin, lovastatin, mevastatin, pravastatin, or rosuvastatin.

In the case when the subject has psoriasis, the pharmaceutical composition comprises the drug candidate selected by the present method described above and a TNF-α inhibitor; and a pharmaceutically acceptable carrier. In preferred embodiments, the drug candidate selected by the present method is a statin, accordingly, the pharmaceutical composition comprises the statin, the TNF-α inhibitor; and a pharmaceutically acceptable carrier. The statin may be any of fluvastatin, atorvastatin, cerivastatin, pitavastatin, or simvastatin. The TNF-α inhibitor may be an anti-TNF-α antibody or a TNF-α antagonist.

In the case when the subject has cancer, the pharmaceutical composition comprises the drug candidate selected by the present method described above and a renin-angiotensin system (Ras) inhibitor; and a pharmaceutically acceptable carrier. In preferred embodiments, the drug candidate selected by the present method is a statin, accordingly, the pharmaceutical composition comprises the statin, the RAS inhibitor; and a pharmaceutically acceptable carrier. The statin may be any of fluvastatin, atorvastatin, cerivastatin, pitavastatin, simvastatin, lovastatin, mevastatin, pravastatin, or rosuvastatin. The RAS inhibitor may be farnesyl thiosalicylic acid (FTS), ARS-853 or ARS-162.

According to some embodiments, the cancer treatable by the present pharmaceutical composition and/or method includes, but is not limited to, bladder cancer, biliary cancer, bone cancer, brain tumor, breast cancer, cervical cancer, colorectal cancer, dysgerminoma, esophageal cancer, epidermal cancer, gastric cancer, gastrointestinal stromal tumor (GIST), glioma, non-Hodgkin's lymphoma, head and neck cancer, intestinal cancer, Kaposi's sarcoma, liver cancer, lung cancer, lymphoma, lymphoid leukemia, melanoma, myeloid leukemia, nasopharyngeal cancer, oral cancer, ovary cancer, pancreatic cancer, prostate cancer, retinoblastoma, renal cell carcinoma, sarcoma, seminoma, skin cancer, spleen cancer, squamous cell carcinoma, teratoma, teratocarcinoma, thyroid cancer, or thyroid follicular cancer. In some embodiments, the cancer is esophageal cancer. In other embodiments, the cancer is lung cancer. In yet other embodiments, the cancer is oral cancer. In still yet other embodiments, the cancer is skin cancer.

Many of the attendant features and advantages of the present disclosure will become better understood with reference to the following detailed description considered in connection with the accompanying drawings.

BRIEF DESCRIPTION OF THE DRAWINGS

The present description will be better understood from the following detailed description read in light of the accompanying drawings, where.

DETAILED DESCRIPTION OF THE INVENTION

Figure 1:
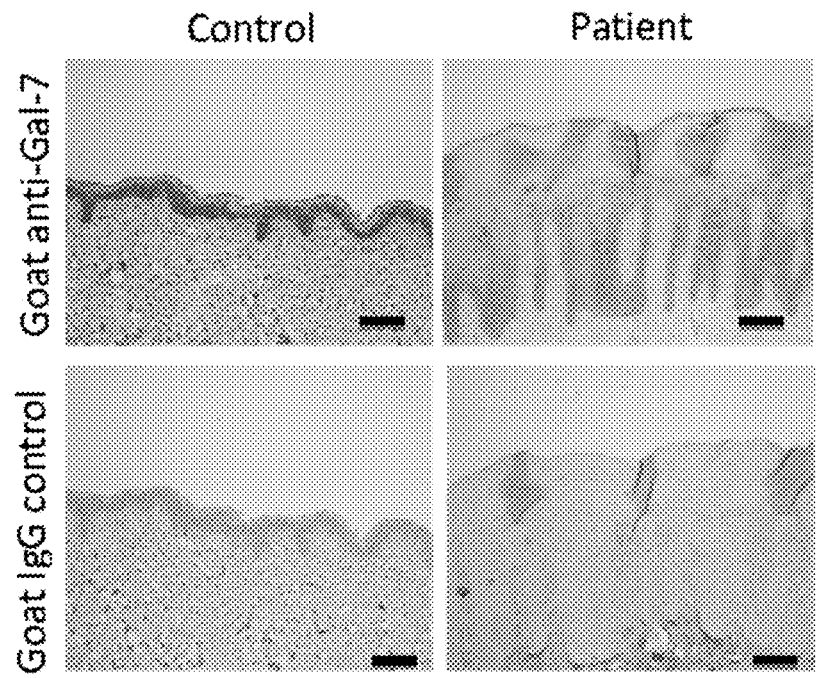
FIG. 1. The expression of galectin-7 is downregulated in epidermal keratinocytes of patients with psoriasis. Panel a: Immunohistochemical (IHC) staining of galectin-7 in skin sections from a healthy control and a psoriatic lesion. Scale bar: 100 m. Panel b: Immunohistochemical staining of galectin-7 in sections of normal skin from healthy controls (n=75) and sections of lesional skin from patients with psoriasis (n=27). Quantification of immunohistochemical staining was performed by computer-assisted methods as described in Methods. The y-axis indicates the arbitrary numbers representing mean intensity across an area of epidermis (InteDen/Area). Panel c: Immunohistochemical staining of galectin-7 in a skin section isolated from intradermally IL-23-injected and PBS-injected mice, respectively. Scale bar: 100 m. Panel d: Immunohistochemical-quantification results from the mouse IL-23-induced psoriasis model (PBS, n=6; IL-23, n=13). Panel e: Immunoblot analysis of galectin-7 levels in HaCaT and HEKn cells stimulated with the indicated cytokines (e.g., IFN-γ, LPS, TNF-α, IL-23, or IL-17A). Both cell groups were stimulated with 100 ng/ml IFN-γ and 50 μg/ml LPS. Cells were treated with cytokines for 2 days, and cell lysates were prepared for immunoblot analysis. GAPDH served as a loading control in the assay. P<0.01 and *P<0.001.
Figure 1:
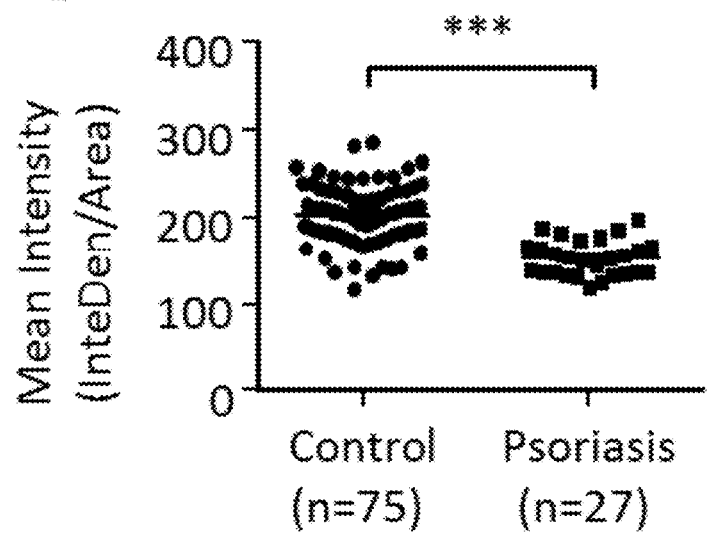
Figure 1:
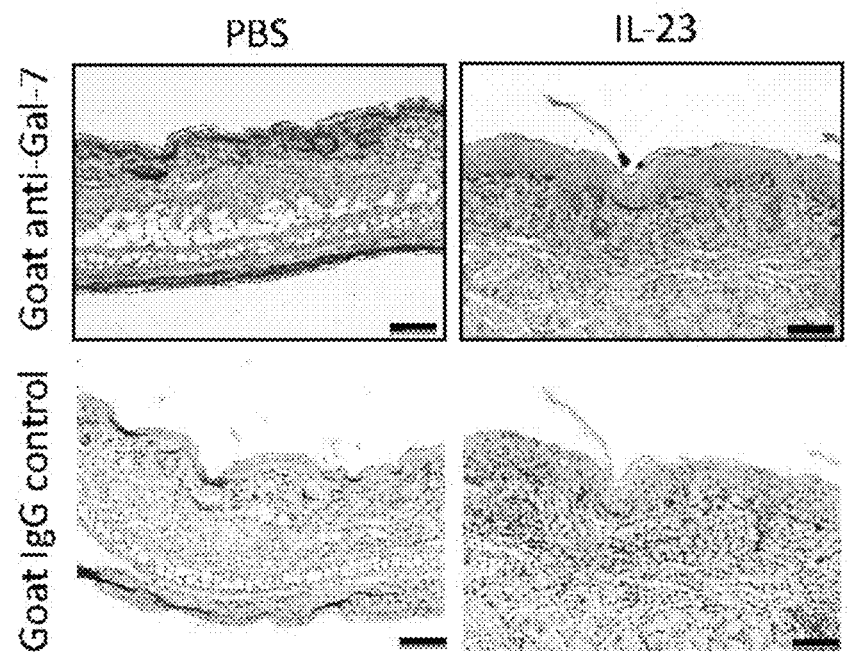
Figure 1:
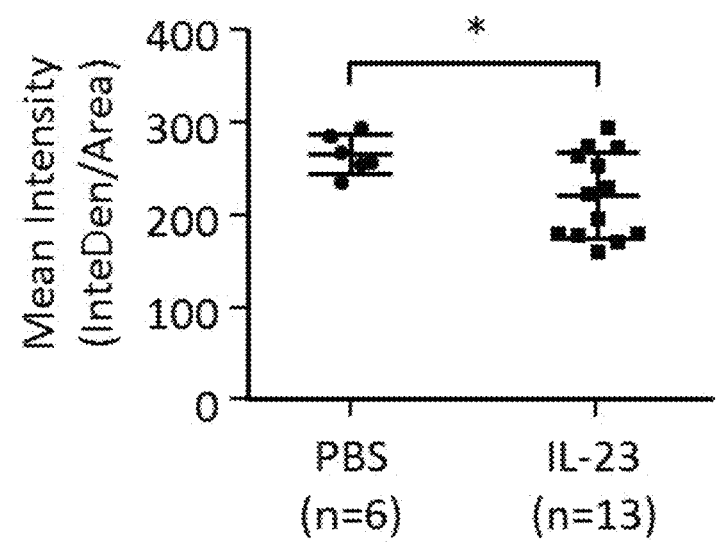
Figure 1:
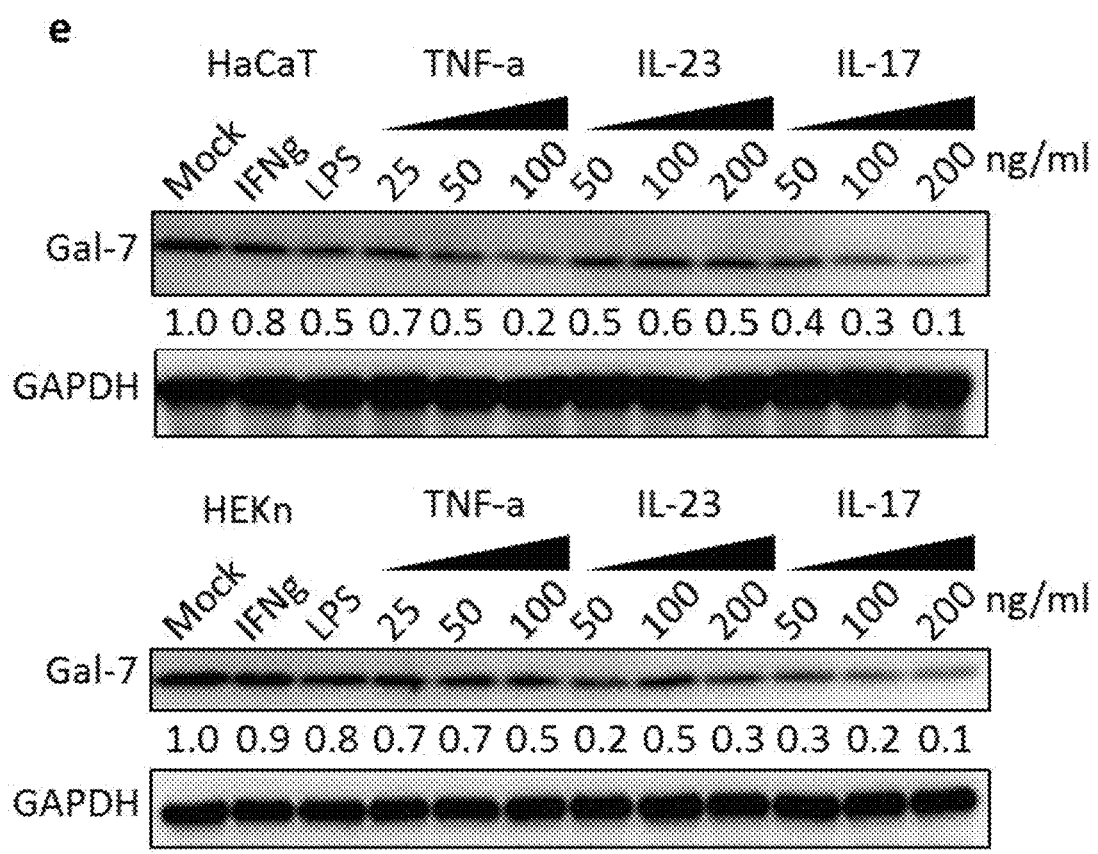

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

I. DEFINITION

For convenience, certain terms employed in the specification, examples and appended claims are collected here. Unless otherwise defined herein, scientific and technical terminologies employed in the present disclosure shall have the meanings that are commonly understood and used by one of ordinary skill in the art. Also, unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Also, as used herein and in the claims, the terms "at least one" and "one or more" have the same meaning and include one, two, three, or more.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about". Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

The term "antibody" is used in the broadest sense and specifically covers monoclonal antibodies (including full length monoclonal antibodies), polyclonal antibodies, multi-specific antibodies (e.g., bi-specific antibodies), and antibody fragments so long as they exhibit the desired biological activity. "Antibody fragments" comprise a portion of a full length antibody, generally the antigen binding or variable region thereof. Examples of antibody fragments include Fab, Fab', F(ab')2, and Fv fragments; diabodies; linear antibodies; single-chain antibody molecules; and multi-specific antibodies formed from antibody fragments.

"Antibody fragments" comprise only a portion of an intact antibody, wherein the portion retains at least one, and as many as most or all, of the functions normally associated with that portion when present in an intact antibody. In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody, such as neonatal Fc receptor (FcRn) binding, antibody half-life modulation, antibody-dependent cell-mediated cytotoxicity (ADCC) function, and complement binding. In one embodiment, an antibody fragment is a monovalent antibody that has an in vivo half-life substantially similar to an intact antibody. For example, such an antibody fragment may comprise an antigen binding arm linked to an Fc sequence capable of conferring in vivo stability to the fragment. The antibody fragment in the present invention may exist in a variety of forms including, for example, variable fragment (Fv), single-chain variable fragment (scFv), antigen-binding fragment (Fab) and F(ab)$_2$, as well as single chain antibodies.

The "variable region" or "variable domain" of an antibody refers to the amino-terminal domains of heavy or light chain of the antibody. These domains are generally the most variable parts of an antibody and contain the antigen-binding sites.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in binding an antibody to an antigen, but exhibit various effector functions, such as participation of the antibody in antibody-dependent cellular toxicity.

The term "complementarity determining region" (CDR) used herein refers to the hypervariable region of an antibody molecule that forms a surface complementary to the 3-dimensional surface of a bound antigen. Proceeding from N-terminus to C-terminus, each of the antibody heavy and light chains comprises three CDRs (CDR 1, CDR 2, and CDR3). A HLA-DR antigen-binding site, therefore, includes a total of six CDRs that comprise three CDRs from the variable region of a heavy chain and three CDRs from the variable region of a light chain.

Depending on the amino acid sequences of the constant domains of their heavy chains, antibodies (immunoglobulins) can be assigned to different classes. There are five major classes of immunoglobulins: IgA, IgD, IgE, IgG and IgM, and several of these may be further divided into subclasses (isotypes), e.g., IgG1, IgG2, IgG3, IgG4, IgA1, and IgA2. The heavy chain constant domains that correspond to the different classes of immunoglobulins are called α, δ, ε, γ, and μ, respectively. The subunit structures and three-dimensional configurations of different classes of immunoglobulins are well known and described generally in, for example, Abbas et al. Cellular and Mol. Immunology, 4th ed. (2000). An antibody may be part of a larger fusion molecule, formed by covalent or non-covalent association of the antibody with one or more other proteins or peptides.

As discussed herein, minor variations in the amino acid sequences of antibodies are contemplated as being encompassed by the presently disclosed and claimed inventive concept(s), providing that the variations in the amino acid sequence maintain at least 85% sequence identity, such as at least 85%, 86%, 87%, 88%, 89%, 90%, 91%, 92%, 93%, 94%, 95%, 96%, 97%, 98% and 99% sequence identity. Antibodies of the present disclosure may be modified specifically to alter a feature of the peptide unrelated to its physiological activity. For example, certain amino acids can be changed and/or deleted without affecting the physiological activity of the antibody in this study (i.e., its ability to treat and/or preventing HBV infection). In particular, conservative amino acid replacements are contemplated. Conservative replacements are those that take place within a family of amino acids that are related in their side chains. Genetically encoded amino acids are generally divided into families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. More preferred families are: serine and threonine are aliphatic-hydroxy family; asparagine and glutamine are an amide-containing family; alanine, valine, leucine and isoleucine are an aliphatic family; and phenylalanine, tryptophan, and tyrosine are an aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the peptide derivative. Fragments or analogs of antibodies can be readily prepared by those of ordinary skill in the art. Preferred amino- and carboxyl-termini of fragments or analogs occur near boundaries of functional domains. In one example, one amino acid residue (e.g., valine) of the present antibody is conservatively replaced (e.g., by leucine). In other examples, two amino acid residues of the present antibody are conservatively replaced by other suitable amino acid residues, for example, valine (V) and arginine (R) are replaced by the pair of amino acids that includes, but is not limited to, methionine (M) and lysine (K), lysine (K) and proline (P), tryptophan (W) and isoleucine (I), isoleucine (I) and proline (P), asparagine (N) and valine (V), and glutamine (G) and lysine (K).

"Percentage (%) sequence identity" is defined as the percentage of amino acid residues in a candidate sequence that are identical with the amino acid residues in the specific peptide sequence, after aligning the sequences and introducing gaps, if necessary, to achieve the maximum percent sequence identity, and not considering any conservative substitutions as part of the sequence identity. Alignment for purposes of determining percentage sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, sequence comparison between two amino acid sequences was carried out by computer program Blastp (protein-protein BLAST) provided online by Nation Center for Biotechnology Information (NCBI). The percentage amino acid sequence identity of a given amino acid sequence A to a given amino acid sequence B (which can alternatively be phrased as a given amino acid sequence A that has a certain % amino acid sequence identity to a given amino acid sequence B) is calculated by the formula as follows:

$$\frac{X}{Y} \times 100$$

where X is the number of amino acid residues scored as identical matches by the sequence alignment program BLAST in that program's alignment of A and B, and where Y is the total number of amino acid residues in A or B, whichever is shorter.

The phrase "pharmaceutically acceptable" refers to molecular entities and compositions that are "generally regarded as safe", e.g., that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans.

The terms "cancer" and "tumor" are used alternatively in the present disclosure and preferably refer to the physiological condition in mammals and especially in humans that is typically characterized by un-regulated cell growth. Cancers in this respect include metastatic cancers, and/or drug-resistant cancers.

II. DESCRIPTION OF THE INVENTION

The present disclosure aims at providing a novel antibody or a fragment there of that exhibits binding affinity and/or specificity to galectin-7, and accordingly, may serve as a platform for selecting a drug candidate suitable for treating galectin-7 associated disease (e.g., psoriasis).

(i) Anti-Galectin-7 Antibody

For the purpose of producing the present antibody, a polypeptide (i.e., galectin-7 or a fragment thereof, serving as an antigen) may be synthesized by commonly used methods such as t-BOC or FMOC protection of alpha-amino groups. Both methods involve stepwise syntheses whereby a single amino acid is added at each step starting from the C terminus of the peptide. Polypeptides of the invention can also be synthesized by the well-known solid phase peptide synthesis methods.

Then, the antibody can be produced by immunizing a host animal, such as a mouse, a rat, or a rabbit, with the synthetic polypeptide. The immunization may be performed in accordance with commonly adopted procedures. The immunization interval is not particularly limited. Immunization may be carried out at intervals of several days to several weeks, preferably one week, for 2-10 times, until a desired antibody titer is reached. For example, the host animals may be vaccinated by subcutaneously injecting with the synthetic polypeptide on weekly basis for 8 consecutive weeks.

After the final immunization, splenic cells and regional lymph nodes are removed. Blood samples are taken regularly after immunization and subject to centrifugation to separate sera. The resultant sera are then subject to measurement of antibody titers by any suitable method, which includes, but is not limited to, enzyme linked immunosorbent assay (ELISA), enzyme immunoassay (EIA), or radio immunoassay (RIA). In one preferred example, antibody titers are measured by ELISA. Then, final immunization is given to those animals showing high antibody titers to the synthetic polypeptide. Antibody-producing cells are prepared from splenic cells and regional lymph nodes or the like of the immunized animals. In the preparation of antibody-producing cells, it is preferably to remove tissue debris and erythrocytes as much as possible. Commercial erythrocyte remover may be used to this purpose. Alternatively, a buffer ammonium chloride and Tris may be prepared and used. The thus prepared antibody-producing cells should be immediately fused with immortal cells such as myeloma cells to produce hybridoma cells, which semi-eternally continue to proliferate while producing antibodies. Commonly available cell strain derived from an animal such as mouse may be used. A preferable cell strain to be used in this invention should not survive in HAT selection medium, which contains hypoxanthine, thymidine and aminopterin; and should survive there only when fused with antibody-producing cells. Examples of myeloma cells include, but are not limited to, mouse myeloma cell line (such as myeloma FO cells) and human myeloma cell line (such as Karpas 707H). Cell fusion is usually carried out by mixing splenic cells or lymph node cells with a commercial available myeloma cells in the presence of a cell-fusion promoter, such as polyethylene glycol (PEG) having an average molecular weight from about 200 to 20,000 daltons or the like. Alternatively, cell fusion may be carried out in a commercial cell fusion device utilizing electric stimulation such as electroporation. After the fusion, the resultant cells are then diluted and cultured in HAT medium.

Hybridomas of interest are then selected from the fused cells. The fused cells surviving cultured in HAT medium would form colonies. The supernatant of each culture well is then collected and examine for the presence or absence of antibody titers to the polypeptide. As a method of confirmation, ELISA, EIA or RIA may be used. Once antibody-positive wells are identified, cells are then cultured in a HT medium, which does not contain aminopterin. After culturing for a while, antibody titers in the culture supernatant are confirmed again. Cells that are finally selected are then subject to cloning to obtain single cells. Clones that exhibit high specificity to the polypeptide are selected, and are proliferated to some extent to establish hybridomas.

The monoclonal antibodies produced by the hybridomas may be isolated or prepared by any known method. For example, antibodies may be prepared from cultured supernatant obtained by culturing hybridomas in a medium with low serum concentration. Alternatively, hybridomas may be injected into abdominal cavities of animals and the resultant abdominal dropsies are collected to prepare antibodies. Antibodies may be purified or isolated by methods that employ affinity column, gel filtration chromatography, ion exchange chromatography or the like. Any of these known methods may be appropriately selected or used in combination.

The thus-produced antibody comprises a VH region and a VL region, in which the VH region comprises CDR-H1, CDR-H2 and CDR-H3, and the VL region comprises CDR-L1, CDR-L2 and CDR-L3.

According to certain embodiments of the present disclosure, the antibody is derived from a hybridoma clone 8F4B11, and accordingly, designated as antibody 8F4B11. In these embodiments, the CDR-H1, CDR-H2 and CDR-H3 of antibody 8F4B11 respectively comprise the amino acid sequences of SEQ ID NOs: 1, 2 and 3; and the CDR-L1, CDR-L2 and CDR-L3 of antibody 8F4B11 respectively comprise the amino acid sequences of SEQ ID NOs: 4, 5 and 6.

Preferably, the VH of antibody 8F4B11 is at least 85% (i.e., 85%, 86%, 87%, 88%, 89%, 90%, 91%, 92%, 93%, 94%, 95%, 96%, 97%, 98%, 99% or 100%) identical to SEQ ID NO: 7, and the VH region of antibody 8F4B11 is at least 85% (i.e., 85%, 86%, 87%, 88%, 89%, 90%, 91%, 92%, 93%, 94%, 95%, 96%, 97%, 98%, 99% or 100%) identical to SEQ ID NO: 8. As could be appreciated, the framework sequence of the VL and VH regions may vary (e.g., being substituted by conserved or non-conserved amino acid residues) without affecting the binding affinity and/or specificity of the present antibody. Preferably, the sequences of the framework is conservatively substituted by one or more suitable amino acid(s) with similar properties; for example, the substitution of leucine (an nonpolar amino acid residue) by isoleucine, alanine, valine, proline, phenylalanine, or tryptophan (another nonpolar amino acid residue); the substitution of aspartate (an acidic amino acid residue) by glutamate (another acidic amino acid residue); or the substitution of lysine (an basic amino acid residue) by arginine or histidine (another basic amino acid residue). More preferably, the VH and VL regions of antibody 8F4B11 are respectively at least 90% identical to SEQ ID NOs: 7 and 8. Most preferably, the VH and VL regions of antibody 8F4B11 are respectively at least 95% identical to SEQ ID NOs: 7 and 8. In one specific embodiment, the VH and VL regions of antibody 8F4B11 respectively has the amino acid sequences of SEQ ID NOs: 7 and 8.

According to certain embodiments of the present disclosure, the antibody is derived from a hybridoma clone 7B12F11, and accordingly, designated as antibody 7B12F11.

Alternatively, the present antibody (i.e., antibody 8F4B11 or 7B12F11) may be produced by DNA cloning. DNA encoding the present antibody may be easily isolated and sequenced by use of conventional procedures, such as using oligonucleotide probes that are capable of binding specifically to genes encoding the heavy and light chains of the antibody. The hybridoma cells serve as a preferred source of such DNA. Once isolated, the DNA may be placed into expression vectors, which are then transfected into host cells such as *E. Coli* cells, simian COS cells or Chinese hamster ovary (CHO) cells or myeloma cells that do not produce immunoglobulin proteins, to synthesize the desired antibodies in the recombinant host cells.

In certain examples, the CDR-H1, CDR-H2 and CDR-H3 of antibody 8F4B111 are respectively encoded by nucleotide sequences of SEQ ID NOs: 9, 10 and 11, and the CDR-L1, CDR-L2 and CDR-L3 of antibody 8F4B11 are respectively encoded by nucleotide sequences of SEQ ID NOs: 12, 13 and 14. In one working embodiment, the VH and VL regions of antibody 8F4B111 are respectively encoded by nucleotide sequences of SEQ ID NOs: 15 and 16. All degenerate nucleotide sequences are included within the scope of the invention as long as the peptide/polypeptide/protein (e.g., the present CDR, VH region or VL region) encoded by the nucleotide sequence maintains the desired activity or function. The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

Depending on intended uses, the present antibody or the DNA encoding the antibody may be used to produce chimeric antibodies (e.g., bi-specific antibodies), humanized antibodies and/or antibody fragments derived thereof.

(ii) Kit Comprising Anti-Galectin-7 Antibody

According to certain embodiments of the present disclosure, compared with the control group (i.e., the healthy skin without any symptom of psoriasis), the expression level of galectin-7 is downregulated in the skin lesion of psoriasis; and the agent enhancing galectin-7 expression provides a potential means to treat psoriasis or cancer. Based on the finding, the second aspect of the present disclosure is thus directed to a kit serving as a platform for selecting psoriasis or cancer drugs. The present kit comprises the antibody as described in Part (I) of the present disclosure, and a pharmaceutically acceptable carrier.

The pharmaceutically acceptable carrier may be a solvent, dispersion agent, antibacterial agent, antifungal agent, isotonic agent, or other agents that are physiologically compatible. Examples of the pharmaceutically acceptable carrier suitable for use in the present kit include, but are not limited to, water, saline, phosphate buffered saline (PBS), tris-buffered saline (TBS), glycerol, ethanol and a combination thereof. The pharmaceutically acceptable carrier may further comprise minor amounts of auxiliary substances such as wetting or emulsifying agents, preservatives or buffers, which enhance the stability or effectiveness of antibody, or antigen-binding portion thereof.

In practice, the antibody of the present kit is employed as a detecting antibody for the detection of galectin-7 expression. Depending on desired purposes, the present kit may further comprise a second antibody specific to galectin-7, a blocking agent (i.e., the agent for blocking non-specific binding between galectin-7 and anti-galectin-7 antibody), and/or a reporter conjugated anti-mouse antibody. For example, in the case when the expression level of galectin-7 in a sample is determined by the present kit via western blotting assay, flow cytometry assay, immunochemistry assay or immunofluorescence assay, then the present kit may comprise the present antibody as the first antibody for detecting galectin-7, the reporter conjugated anti-mouse antibody as the second antibody for detecting the first antibody (i.e., the present antibody), and optionally, the blocking agent. Alternatively, when the present kit is employed to detect the expression level of galectin-7 via ELISA, then it may comprise the present antibody as the capture antibody or the detection antibody, the second anti-galectin-7 antibody as the detection antibody (in the case when the present antibody serving as the capture antibody) or the capture antibody (in the case when the present antibody serving as the detection antibody), and optionally, the blocking agent.

As could be appreciated, in addition to psoriasis, the kit of the present disclosure is also useful in selecting a drug candidate suitable for treating other inflammatory diseases (e.g., lichen sclerosus, atopic dermatitis, or inflammatory bowel disease) or diseases associated with and/or caused by abnormal expression (e.g., upregulation or downregulation) of galectin-7, for example, allergy.

(iii) Uses of the Present Antibody or Kit for Selecting a Drug Candidate

The third aspect of the present disclosure pertains to the use of the antibody or kit in accordance with any aspect or embodiment of the present disclosure in selecting a drug candidate for the treatment of a galectin-7 associated disease, for example, a cancer, inflammatory disease (e.g., psoriasis), or allergy.

According to certain embodiments, the method of selecting a drug candidate for the treatment of psoriasis or cancer comprises the steps of, (a) incubating keratinocytes with one or more candidate drugs;

(b) determining the expression level of galectin-7 in the keratinocytes of step (a) by the present antibody or kit; and (c) selecting the drug candidate from the one or more candidate drugs based on the expression level determined in step (b), wherein the drug candidate increases the expression level of galectin-7.

In the step (a), keratinocytes are treated with one or more candidate drugs for a period of time. According to one embodiment of the present disclosure, the keratinocytes are immortalized keratinocytes. According to another embodiment of the present disclosure, the keratinocytes are primary neonatal epidermal keratinocytes.

Next, the expression level of galectin-7 in the keratinocytes of step (a) is determined by the present antibody or kit as described in the step (b). For the purposes of determining the expression level of galectin-7 in keratinocytes, the keratinocytes are first lysed by a method familiar with a person skilled in the art, for example, freezing and thawing, sonication, pressure, enzyme, detergent, or a combination thereof. The protein in the cell lysate is then quantified by the present kit or antibody via suitable assay, for instance, ELISA, western blotting assay, or flow cytometry assay.

Alternatively, it is known that galectin-7 would be released into culture medium. Thus, the expression level of galectin-7 may be directly measured by collecting the supernatant of culture medium followed by quantitating by the present kit or antibody via suitable assay.

As aforementioned, the expression level of galectin-7 is downregulated in psoriasis as compared to healthy skin, and the agent enhancing the expression of galectin-7 is useful in treating psoriasis. Similarly, the expression level of galectin-7 is downregulated in a cancer as compared to its non-malignant counterpart, and the agent enhancing the expression of galectin-7 is useful in treating such cancer. Accordingly, based on the quantitated result of step (b), a person skilled in the art may select a proper drug candidate to treat psoriasis or cancer as described in the step (c), in which the selected drug candidate increases the expression level of galectin-7.

In some examples, the selected drug candidate is a statin, such as fluvastatin, atorvastatin, cerivastatin, pitavastatin, or simvastatin for treating psoriasis, while using fluvastatin, atorvastatin, cerivastatin, pitavastatin, simvastatin, lovastatin, mevastatin, pravastatin, or rosuvastatin for treating cancer. Preferably, the selected drug candidate is fluvastatin.

The present method may be applied to select a drug candidate for treating other galectin-7 associated diseases, such as allergy.

(iv) Pharmaceutical Composition and Uses Thereof

The fourth aspect of the present disclosure pertains to a pharmaceutical composition for treating psoriasis or cancer. The present pharmaceutical composition comprises the drug candidate selected by the present method described above; and a pharmaceutically acceptable carrier. In some embodiments, the selected drug candidate is a statin, which includes but is not limited to, fluvastatin, atorvastatin, cerivastatin, pitavastatin, simvastatin, lovastatin, mevastatin, pravastatin, and rosuvastatin. Preferably, the selected drug candidate is fluvastatin.

In the case when the subject has psoriasis, the pharmaceutical composition further comprises a TNF-α inhibitor, which may be an anti-TNF-α antibody or a TNF-α antagonist. According to certain embodiments of the present disclosure, the administration of the statin and the TNF-α inhibitor exhibits a therapeutic effect on psoriasis via enhancing galectin-7 expression. In these embodiments, the statin and the TNF-α inhibitor additively or synergistically ameliorate or alleviate the symptoms associated with psoriasis.

In the case when the subject has cancer, then the pharmaceutical composition may further comprise a RAS inhibitor, which may be farnesyl thiosalicylic acid (FTS), ARS-853 or ARS-162. According to other embodiments of the present disclosure, the administration of the statin and the RAS inhibitor exhibits a therapeutic effect on cancer via enhancing galectin-7 expression. In these embodiments, the statin and the RAS inhibitor additively or synergistically ameliorate or alleviate the symptoms associated with the cancer.

Exemplary cancers or tumors treatable by the present pharmaceutical composition and/or method include, but are not limited to, bladder cancer, biliary cancer, bone cancer, brain tumor, breast cancer, cervical cancer, colorectal cancer, dysgerminoma, esophageal cancer, epidermal cancer, gastric cancer, gastrointestinal stromal tumor (GIST), glioma, non-Hodgkin's lymphoma, head and neck cancer, intestinal cancer, Kaposi's sarcoma, liver cancer, lung cancer, lymphoma, lymphoid leukemia, melanoma, myeloid leukemia, nasopharyngeal cancer, oral cancer, ovary cancer, pancreatic cancer, prostate cancer, retinoblastoma, renal cell carcinoma, sarcoma, seminoma, skin cancer, spleen cancer, squamous cell carcinoma, teratoma, teratocarcinoma, thyroid cancer, or thyroid follicular cancer.

Accordingly, the method comprises administering to a subject in need thereof an effective amount of the present pharmaceutical composition.

The subject is a mammal, including a rat, a mouse, a human, a pig, a monkey, a goat, a sheep, a horse, a cat, and a dog. Preferably, the subject is a human.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

EXAMPLE

Materials and Methods

Human Skin Tissue Samples

Human skin tissues from patients with psoriasis (n=27) and healthy volunteers (n=75) were acquired in accordance with a protocol approved by the Chung Shan Medical School Institutional Review Board with informed consent forms. Patients with psoriasis vulgaris received a diagnosis based on clinical and histopathological criteria and patients receiving systemic therapies were excluded. The analysis of human tissue samples was approved by the Institutional Review Board of Academia Sinica, Taiwan.

Galectin-7 IHC Quantification

Quantification of immunohistochemical staining was performed by computer-assisted methods. The 100× magnified visual fields of tissue sections (size area of 1.5 mm$^2$) were examined. The epidermal region of each visual field was selected, and the intensity of galectin-7 staining from each pixel in the epidermis region was quantified by software. To calculate the mean intensity of galectin-7 staining in each skin section, the intensity of galectin-7 staining was divided by the epidermal-area size. All tissue sections from healthy controls (n=75) and patients with psoriasis (n=27) were analyzed.

Mice

Galectin-7$^{-/-}$ mice with the C57BL/6 background were generated by the European Conditional Mouse Mutagenesis Program (EUCOMM) from embryonic stem cell line EPD0327_3_B05 and were acquired from the Wellcome Trust Sanger Institute (Cambridge, UK). All animal experiments were conducted at a specific pathogen-free facility and complied with the guidelines approved by the Animal Care and Use Committee of the Institute of Biomedical Sciences (Academia Sinica, Taipei, Taiwan).

Keratinocyte Culture and Preparation of Galectin-7 Knockdown Cells

Human keratinocyte cell line HaCaT was maintained at 37° C. in Dulbecco's modified Eagle's medium (DMEM) supplemented with 10% of fetal bovine serum (FBS), 2 mM glutamine, 100 U/ml penicillin and 100 µg/ml streptomycin. Short hairpin RNA (shRNA) reagents were obtained from the National RNAi Core Facility located at the Institute of Molecular Biology and Genomic Research Center, Academia Sinica, supported by the National Core Facility Program for Biotechnology Grants of NSC. Four shRNAs with clone IDs of TRCN0000057393, TRCN0000057394, TRCN0000057395, and TRCN0000057396 were used to generate stable galectin-7 knockdown HaCaT clones. HaCaT cells were infected with one of the four shRNA-expressing lentiviruses and puromycin was employed to select stable cell clones after 3 days of infection. After puromycin selection, four individual pooled clones were cultured in puromycin-free medium for 2 weeks before further analysis.

Primary neonatal human epithelial keratinocytes, HEKn cells, were purchased from Gibco. HEKn cells were cultured at 37° C. in keratinocyte serum-free medium (K-SFM) supplemented with 30 µg/ml bovine pituitary extract and 5 ng/ml recombinant human epidermal growth factor from the same company. Compared with HaCaT cells, HEKn cells have a limited proliferation ability and are not suitable for establishing shRNA-based stable knockdown cells; therefore, a small interfering RNA (siRNA) oligo was used to transiently knock down the expression of galectin-7. The Silencer® Select siRNAs were purchased from Invitrogen, including negative control #1 and a predesigned siRNA targeting human galectin-7 (Catalog number: s230574, which targets the sequence of exon 3 of NM_002307.3). Thirty picomoles of siRNAs were delivered into HEKn cells in a 6-well plate setup by means of Lipofectamine 2000.

Measurement of Cytokine Production

To measure the concentrations of proinflammatory cytokines secreted by keratinocytes, $2 \times 10^4$ cells were seeded in 96-well plates. Cells were incubated for 24 hours and then treated with 50 µg/ml LPS, 100 ng/ml human TNF-α, 100 or 200 ng/ml human IL-17A, 200 ng/ml human IL-22, 100 ng/ml human IL-23, or 50 ng/ml IFN-γ at 37° C. for 48 hours. In addition, the MEK inhibitor PD98059 was added along with stimulation by LPS or IL-17A (48 hours). The supernatants were then collected and analyzed by ELISAs, which were performed using a specific combination of paired antibodies (capture and detection antibodies).

Immunoblot Analysis

Cells were harvested and lysed in RIPA lysis buffer containing 1% of Triton X-100 and a protease inhibitor cocktail, and total protein concentrations were measured with a protein assay kit. Proteins in the samples of the lysates with the same amounts of total protein were separated by sodium dodecyl sulfate polyacrylamide gel electrophoresis (SDS-PAGE) and analyzed by immunoblotting. Primary antibodies against phospho-Erk1 (pT202)/Erk2 (pT185), Erk1, Erk2, NF-κB p65, phospho-NF-κB p65 (pS536), IκBα, phospho-IκBα pS32, β-actin, or GAPDH were applied to detect the corresponding proteins. Horseradish peroxidase (HRP)-conjugated secondary antibodies against mouse, rabbit, or goat IgG were then incubated with the membranes, and proteins were visualized by chemiluminescence according to the manufacturer's instructions. Protein quantification was performed by software.

Quantitative RT-PCR (RT-qPCR)

Total RNAs (including mRNA and miRNA) were extracted from cultured cells or mouse ears with the TRIzol Reagent. For measurement of human galectin-7, IL-6, IL-8, IL-17A, and IFN-γ levels, mRNAs were reverse-transcribed into cDNA by means of the cDNA synthesis kit, and real-time PCR was carried out with specific probes accompanied with primers targeting humangalectin-7, IL-6, and IL-8 according to the manufacturer's instructions.

For miR-146a quantification, total RNA samples were converted to cDNA, and real-time PCR was conducted with specific primers targeting miR-146a. Human GAPDH and U6 snRNA were selected as internal controls for normalization of the levels of mRNAs and miRNAs, respectively. Relative levels of mRNAs and miRNAs were calculated, and fold changes were obtained by the ΔΔCt method and compared with vector-only control cells.

The Model of IL-23-Induced Psoriasis

The IL-23-induced mouse psoriasis-like model was used in this study. Intradermal injection of recombinant IL-23 (1 µg) (or PBS as control) into the right ear of anesthetized mice was performed with an insulin syringe every other day for 16-21 days. Ear thickness was measured before and after the intradermal injection and measurements were taken at the center of the ears using a pocket thickness gage. Mice were euthanized, the ears were collected, and a half of the ears were embedded in paraffin for H&E, immunohistochemical, and in situ hybridization staining, while RNAs from the other half of ears were extracted for analysis of the cytokine and miRNA profiles by RT-qPCR.

To study the effect of statins in this mouse psoriatic model, 30 mg/kg/day fluvastatin or pravastatin were administrated to mice using oral gavage for 14 days. The saline was used as the control. The experimental groups were designed and arranged as PBS (n=2), IL-23 (n=3), PBS+Saline (n=5), IL-23+Saline (n=5), PBS+Fluvastatin (n=3), IL-23+Fluvastatin (n=4), PBS+Pravastatin (n=4), IL-23+Pravastatin (n=4). Ear thickness was measured as described above. On day 15, mice were euthanized, the ears were collected, and a half of the ears were embedded in paraffin for H&E staining, immunohistochemical staining, and RNAs from the other half of ears were extracted for analysis of galectin-7 expression.

The animal experiment protocol was evaluated and approved by the Institutional Animal Care and Use Committee of Academia Sinica.

Histology and Immunohistochemistry

Sections of paraffin-embedded mouse ears were prepared and stained with H&E. For immunohistochemical staining, 5-µm-thick sections of 4% paraformaldehyde-fixed mouse ears or human skin were deparaffinized and hydrated with distilled water. Heat-induced epitope retrieval was performed by incubation in citrate buffer at 98° C. for 10 minutes, and endogenous peroxidase was quenched by treatment with 3% $H_2O_2$ in PBS for 5 minutes. Next, 2.5% horse serum was applied to block nonspecific binding on the tissue sections for 1 hour. Galectin-7 in both mouse and human skin was detected by incubation with a goat anti-galectin-7 antibody (primary antibody) for 1 hour. After washes with PBS, the histological slides were incubated with a polymer-HRP-conjugated horse anti-goat IgG antibody (secondary antibody) for 30 minutes. The staining reaction for galectin-7 was visualized by peroxidase substrate kit, and positive signals of 3,3'-diaminobenzidine (DAB) chromogen were developed as red-brown precipitates. The slides were counterstained with hematoxylin to detect nuclei.

MiRNA In Situ Hybridization

LNA-modified, digoxigenin (DIG)-labeled DNA probes complementary to human miR-146a were designed for in situ hybridization of mouse and human skin sections according to the manufacturer's instructions. A scrambled miRNA probe was a negative control, and the probe complementary to U6 snRNA served as a positive control. All the sections were deparaffinized in xylene and rehydrated in a graded series of ethanol solutions. For reagent penetration, the sections were subjected to proteinase K digestion (5-10 µg/ml) at 37° C. for 5 minutes, followed by treatment with 4% paraformaldehyde in PBS for 15 minutes and with a prehybridization solution at 50° C. for 3-4 hours. The tissue samples were hybridized with specific probes overnight at 53° C. After the sections were washed with an SSC buffer dilution series, immunological detection with an alkaline phosphatase-conjugated anti-DIG antibody was carried out. Detection of signals was based on a reaction with nitro blue tetrazolium chloride/5-bromo-4-chloro-3-indolyl phosphate substrate, followed by counterstaining of nuclei with nuclear fast red.

Antibodies and Compounds

Gefitinib (cat. #G304000, Toronto Research Chemicals), the epidermal growth factor receptor (EGFR) inhibitor (cat. #324674, Merck), farnesyl thiosalicylic acid (FTS) (cat. #10010501, Cayman), goat anti-galectin-7 antibody (Novagen), rabbit anti-phospho-EGFR antibody (Tyr1068) (cat. #2234, Cell Signaling Technology), rabbit anti-phospho-ERK antibody (cat. #4370, Cell Signaling Technology), rabbit anti-CDH1 antibody (cat. #3195, Cell Signaling Technology), rabbit anti-VIM antibody (cat. #5741, Cell Signaling Technology), rabbit anti-EGFR antibody (cat. #1902, Epitomics), and rabbit anti-phospho-Akt antibody (cat. #2118, Epitomics) were available commercially.

Cancer Cell Culture and Generation of Galectin-7 Overexpressing, Knockdown, and Knockout Stable Cells CL83, CL141, CL100, CL25, PC9, PC9-IR, CL97, H1975, and H3255 cells were obtained from Dr. Pan-Chyr Yang (National Taiwan University, Taiwan), and A-431 (ATCC© CRL-1555™), H1650 ((ATCC© CRL-5883™)) and HCC827 ((ATCC© CRL-2868™)) cells were purchased from ATCC. Cells were cultured in RPMI 1640 medium supplemented with 10% fetal bovine serum (Gibco). The mRNA of A549, H23, H226BR, H358, H460, H661, H928, H1299, H1435, and H1437 cells were produced by conventional method, such as the method as described herein.

Wild-type galectin-7 was cloned into pEGFP-N1 and p3×FLAG-CMV-14 expression vectors. Control and galectin-7-encoding plasmids were transfected into lung cancer cell lines as aforementioned using the jetPRIME transfection reagent (Polyplus). After transfection, G418 was applied to select stable cell clones. After selection, galectin-7-overexpressing cell clones were obtained. The galectin-7-overexpressing cell clones were cultured in G418-free RPMI 1640 medium for 2 weeks prior to analysis.

Lentivirus-encoded short hairpin RNAs (shRNAs) against human galectin-7 with IDs TRCN0000057393, TRCN0000057394, TRCN0000057395, and TRCN0000057396 as aforementioned were used to generate stable galectin-7 knockdown lung cancer cell clones. After infection with shRNA-carrying lentivirus for 3 days, puromycin was given for selecting stable cell clones. After selection, galectin-7 knockdown cell clones were obtained. Galectin-7 knockdown cell clones were cultured in puromycin-free RPMI 1640 medium for 2 weeks prior to analysis.

For generation of galectin-7 knockout cell clones, PC9-IR cells were used by clustered regularly interspaced short palindromic repeats (CRISPR) technology. Two single-stranded DNA oligonucleotides, one is the galectin-7-specific crRNA (5'-CTGCCCGAGGGCATCCGCCC-3', SEQ ID NO: 17) with GTTTT 3' overhang, while the other is the reverse complementary sequence (5'-GGGCGGATGCCCTCGGGCAG-3', SEQ ID NO: 18) with CGGTG 3' overhang, were cloned into GeneArt CRISPR Nuclease OFP Vector (Invitrogen). PC9-IR cells were transfected with the generated CRISPR plasmid for 4 hours, cultured in fresh medium for 2 days, and sorted by FACSJazz cell sorter (BD biosciences) to isolate the single transfected cells with OFP. Cell lysate and genomic DNA of each single cell clone were collected and analyzed by immunoblot and ABI PRISM 96-capillary 3730xl DNA Analyzer respectively. The successfully transfected cell clones without deletion of galectin-7 were defined as control cell clones.

RNA Extraction, mRNA, and miRNA Quantitative Real-Time PCR

Total RNA from each lung cancer cell clone was extracted using TRIzol Reagent (Invitrogen), and cDNA for real-time PCR was generated using the iScript cDNA synthesis kit (Bio-Rad). Quantitative real-time PCR was performed using TaqMan buffer (Roche), and the primers and probes were designed using the Roche Universal Library (UPL). The following forward and reverse primers and probes were used: for galectin-7 (NM_002307), forward primer 5'-CAGACGACGGCTTCAAGG-3' (SEQ ID NO: 19), reverse primer 5'-AAGATCCTCACGGAGTCCAG-3' (SEQ ID NO: 20), and probe #10 (cat. #04685091001); galectin-3 (NM_002306), forward primer 5'-GAGCCTACCCTGCCACTG-3' (SEQ ID NO: 21), reverse primer 5'-AGGCAAAGGCAGGTTATAAGG-3' (SEQ ID NO: 22), and probe #3 (cat. #04685008001); and glyceraldehyde-3-phosphate dehydrogenase (GAPDH) (NM_002046), forward primer 5'-AGCCACATCGCTCAGACAC-3' (SEQ ID NO: 23), reverse primer 5'-GCCCAATACGACCAAATCC-3' (SEQ ID NO: 24), and probe #33 (cat. #04687663001). For real-time PCR, the CFX Connect Real-Time PCR System (Bio-Rad) was used, and the data were analyzed using CFX Manager software, in which the ΔΔCt method was employed to normalize the data against the endogenous control GAPDH.

For miRNA quantitative real-time PCR, the Mir-X miRNA First-Strand Synthesis Kit (Clontech) was used according to manufacturer's instructions. The primers for miR-203 (MI0000283) were based on their mature sequences: hsa-miR-203a-5p (MIMAT0031890) AGUGGUUCUUAACAGUUCAACAGUU (SEQ ID NO: 25), and hsa-miR-203a-3p (MIMAT0000264) GUGAAAUGUUUAGGACCACUAG (SEQ ID NO: 26) according to miRbase (v16.0). Real-time PCR was performed using the CFX Connect Real-Time PCR System using the SYBR Green qRT-PCR master mix (Applied Biosystems), and relative quantification was performed using CFX Manager software, in which the ΔΔCt method was employed to normalize the data against the endogenous control U6.

Immunohistochemistry Staining

Tissue arrays of stage 1 and variable stage lung adenocarcinomas archived at the Biobank of Veterans General Hospital in Taipei, Taiwan were acquired under IRB-approved protocol (IRB-TPEVGH No.: 2017-03-001BC and IRB-AS No.: AS-IRB-BM-17022). Tissue sections underwent immunohistochemical (IHC) detection of galectin-7 by the following protocol. In brief, the tissue sections were incubated with the primary antibody goat anti-galectin-7 antibody at 1 µg/ml (Novagen). Following incubation, the ImmPRESS HRP horse anti-goat IgG (peroxidase) polymer detection kit (Vector Laboratories) was used for signal detection.

Transwell Migration and Invasion Assay

A transwell migration and invasion assay using a 24-well transwell culture plate (8.0 m PET membrane, Corning) and matrigel-coated invasion chambers (8.0 m, BD biosciences) was employed using the protocol as described in Justus C R et al. In vitro cell migration and invasion assays. J Vis Exp 2014(88). $5 \times 10^4$ lung cancer cells were suspended in 100 µl serum-free RPMI 1640 medium and plated in the upper well, while 600 µl medium containing 10% FBS was plated into the bottom well. After 18 hours incubation, the transwell membranes were fixed with cold methanol and stained using a 0.5% crystal violet solution. Cells on the upper side of the transwell membrane were removed by cotton swab, and those on the lower side were counted under a microscope. Four images for each sample were randomly chosen.

Single Cell Migration Assay

A Leica MDI600B time-lapse microscope was used to monitor single cell migration. Lung cancer cells were seeded at a density of $1 \times 10^4$ cells/ml in 24-well plates, and movement of the cells was examined using the time-lapse microscopy. Images of cells were automatically captured every 10 minutes for 24 hours using a 10× objective lens. For each cell line, the movements of 20-30 separate cells were tracked. Cell migration was analyzed using MetaMorph software.

Wound Healing Scratch Assay $2 \times 10^5$ cells/well lung cancer cells were plated in 24-well plates and cultured overnight to form confluent cell monolayers. The monolayers were scratched with a 1 ml pipette tip across the center of the wells, and the recovery of the wounded area was recorded using a Leica MDI600B time-lapse microscope. Images of cells were automatically captured after 24 hours using a 4× objective lens. Recovered surface area was analyzed using MetaMorph software.

Knockdown and Overexpression of miR-203 in Lung Cancer Cells

A miR-203-overexpressing vector (PMIRH203AA-1, System Biosciences) and a scrambled control hairpin in pCDH-CMV-MCS-EF1-copGFP (CD511B-1, System Biosciences) were used to generate miR-203-overexpressing and control lung cancer cells. To downregulate miR-203 in lung cancer cells, an antisense miR-203 vector (MZIP203-PA-1, System Biosciences) and a miRZip scrambled hairpin control vector (MZIP000-PA-1, System Biosciences) were used. System Biosciences Lung cancer cells were transfected with the individual vectors using the jetPRIME transfection reagent (Polyplus). After 4 hours transfection, transfected cells were cultured in fresh medium for 24 hours prior to analysis. The level of miR-203 of each sample was assessed by quantitative real-time PCR.

Animal Studies In Vivo

NOD.CB17-Prkdcscid/JNarl mice obtained from National Laboratory Animal Center (Taiwan) were engrafted $2 \times 10^6$ lung cancer cells subcutaneously at the left and right flanks of the mice. After 10 days of tumor growth, mice were treated by oral gavage with 30 mg/kg fluvastatin or lovastatin in saline solution, or saline solution alone as control, once per day for 21 days. The tumor plaques were harvested and each of them was cut into two pieces. One piece was for immunoblot analysis, and the other one was fixed with 10% formalin and embedded into paraffin block for IHC staining. All animal studies were conducted in the experimental animal facilities of Institute of Biomedical Sciences, Academia Sinica, Taipei, Taiwan, in accordance to institutional rules and ethical guidelines for experimental animal care.

Immunoblot Analysis

Lysates from different lung cancer cell samples were prepared and aliquots containing 30 µg of protein from each lysate were analyzed using either 10% or 12% sodium dodecyl sulfate-polyacrylamide gel electrophoresis (SDS-PAGE). A polyvinylidene difluoride Immobilon H-bond membrane (EMD Millipore) was used for immunoblot analysis. The primary antibody against galectin-7 (Novagen) was used.

Ras-GTP Pull-Down Assay

Active GTP-bound Ras was pulled down and detected using the Ras Pull-down Activation Assay Biochem Kit (cat. #BK008, Cytoskeleton) according to the manufacturer's instructions.

Colony Formation Assay

Lung cancer cells were seeded in 24-well plate at the density of 200 cells/well. Cells were incubated for 14 days before being fixed by ice-cold methanol for 10 minutes. After fixation, cells were stained with 0.05% crystal violet solution (0.5 g crystal violet in 1 L 20% ethanol).

Sphere Formation Assay

Lung cancer cells were trypsinized and resuspended in serum free stem cell culture medium (DMEM/F12 (Gibco) with N2 supplement (Thermo Fisher), 10 ng/ml human EGF, and 10 ng/ml human bFGF) and seeded in ultra-low attachment 24-well plate (Corning) at the density of $10^3$ cells/well. Cultures were fed every 4 days by replacing half the medium. After 12 days incubation, sphere number and diameter were counted and analyzed under a microscope.

Statistics

All quantitative data are presented as mean±SEM, SE, or SD unless indicated otherwise. Quantitative results were analyzed using Prism 6 (GraphPad Software). Fisher's exact test was used to analyze the association between EGFR mutations and galectin-7 expression. Log-rank (Mantel-Cox) test was used to analyze the differences in overall and disease-free survival. One-way analysis of variance (ANOVA) with Tukey's post-hoc test was used to analyze the differences between the groups and pairs. Two-tailed, unpaired Student's t test was applied to compare the samples, and differences with P values less than 0.05 were considered statistically significant.

Example 1 Down-Regulated Expression of Galectin-7 in Human Psoriatic Lesions and Mouse Psoriasiform Dermatitic Lesions Induced by IL-23

Galectin-7 protein levels in the skin lesions of patients with psoriasis and normal skin of healthy controls were examined by immunohistochemical staining (FIG. 1, Panels a and b). The data indicated that galectin-7 was strongly expressed in all epidermal layers of normal skin (FIG. 1, Panel a), but was significantly down-regulated in psoriatic skin (FIG. 1, Panel b). The reduction of galectin-7 protein levels in psoriatic epidermis was verified by computer-assisted quantitation analysis of immunohistochemical staining (FIG. 1, Panel b).

To test whether galectin-7 expression is also reduced in mouse models of psoriasis, IL-23 was intradermally injected in mice to induce inflammation. Injection of IL-23 into the ears of wild-type (WT) mice induced marked ear swelling as expected. This response was associated with epidermal hyperplasia and lymphocyte infiltration, which were not seen after PBS injection (controls; FIG. 1, Panel c), as evaluated by measurement of epidermal thickness as well as by hematoxylin and eosin (H&E) staining. IL-23-injected epidermis also showed drastically reduced galectin-7 expression (FIG. 1, Panels c and d).

The effects of cytokines (i.e., IL-17A, IL-23, and TNF-α, which are known to promote psoriatic inflammation) on galectin-7 expression in immortalized human keratinocytes (HaCaT cells) and primary neonatal epidermal keratinocytes (HEKn cells) were then examined. The data indicated that IL-17A alone reduced galectin-7 protein expression in both HaCaT and HEKn cells (FIG. 1, Panel e). TNF-α significantly reduced galectin-7 expression in HaCaT cells, and interferon (IFN)-γ, lipopolysaccharide (LPS), and IL-23 had modest effects on galectin-7 expression in these cells.

Example 2 Suppression of Galectin-7 Expression Promotes Production of Proinflammatory Cytokines and Chemokines Microarray analysis of galectin-7 knockdown HaCaT cells revealed upregulation of several chemokines genes (CCL3, CCL4, CXCL2, CXCL3, and others) and psoriasis-related genes (including serine protease inhibitors, SER-PINA3 and SERPINB4; S100 calcium-binding proteins, S100A7 and S100A7A; and defensin 04A, DEFB4A) in these cells, as compared with control cells (data not shown). This finding suggested that reduced galectin-7 expression might promote inflammation, thereby contributing to the pathogenesis of psoriasis. The expression of cell surface receptors, IL-17RA, TLR4, and IFN-γR were examined by flow cytometry, and no significant changes were found in galectin-7 knockdown cells compared with controls (data not shown). Accordingly, galectin-7 was hypothesized to exhibit a suppressive effect on the cell signaling pathways of inflammatory responses, i.e., galectin-7 downregulation favored proinflammatory-cytokine production during inflammation.

Figure 2:
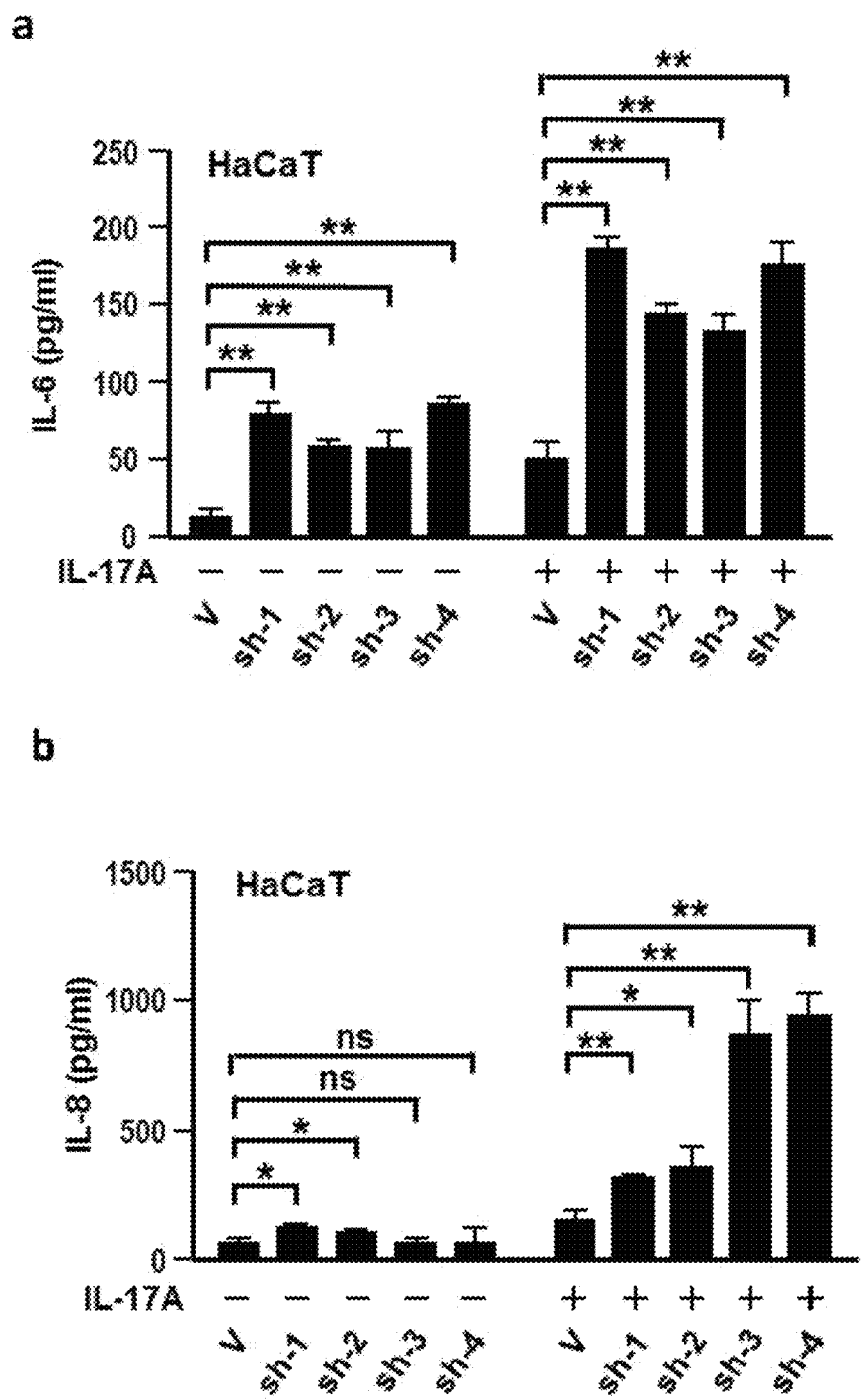
FIG. 2. Downregulation of galectin-7 in keratinocytes causes elevated production of pro-inflammatory cytokines (IL-6 and IL-8) in IL-17A-stimulated keratinocytes. Panels a and b: Galectin-7 knockdown cell lines (sh-1, sh-2, sh-3, and sh-4) and controls were incubated with or without IL-17A for 2 days, and the expression level of IL-6 and IL-8 was measured by ELISA. All the experiments included three biological replicates. Panels c and d: HEKn cells were transfected with the siRNA to knock down galectin-7 and then incubated with or without IL-17A for 2 days. The supernatants were collected for IL-6 and IL-8 analyses by ELISA. For statistical analysis, each shRNA- or siRNA-treated cell line was compared with its corresponding control (V and si-NC) for both mock and IL-17-treated groups. The shRNAs and siRNAs for the knockdown of galectin-7 expression are as described in Methods; ns: not significant, *P<0.05, **P<0.01.
Figure 2:
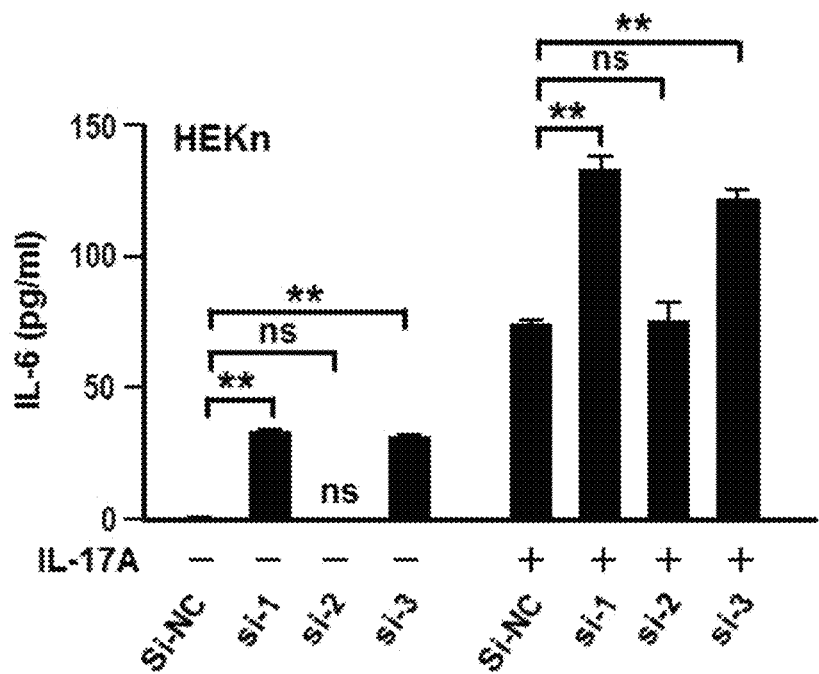
Figure 2:
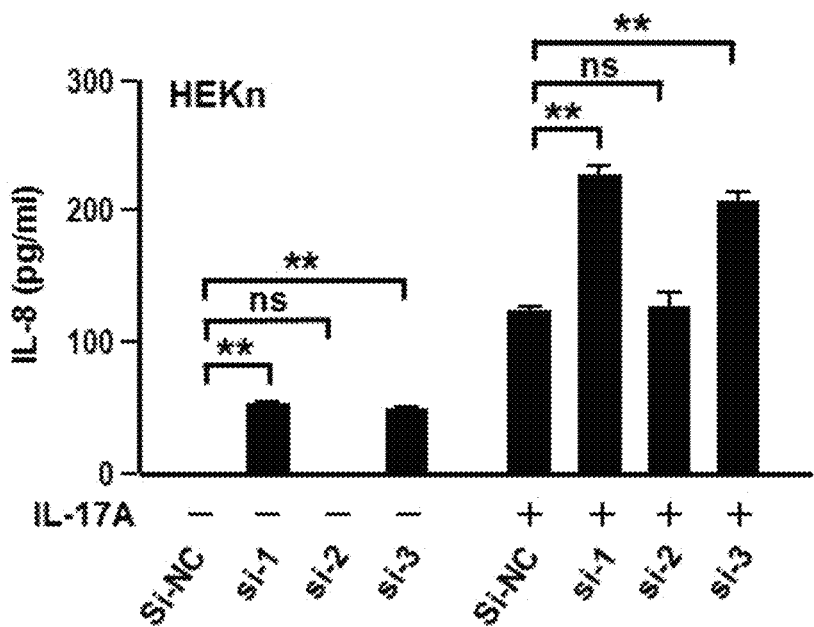

HaCaT and HEKn cells were subjected to different immune stimuli, including IL-17A, IL-21, IL-22, IL-23, TNF-α, LPS, or IFN-γ, and the cytokine secretion was measured by enzyme-linked immunosorbent assays (ELISAs). Among these stimuli, only IL-17A (FIG. 2), TNF-α, and LPS (data not shown) induced IL-6 and IL-8 production. Galectin-7 knockdown cells secreted greater amounts of IL-6 and IL-8 in response to stimulation with IL-17A, as compared to control cells (FIG. 2). Stronger constitutive secretion of IL-6 and IL-8 was observed in galectin-7 knockdown cells without stimulation (FIG. 2).

Figure 3:
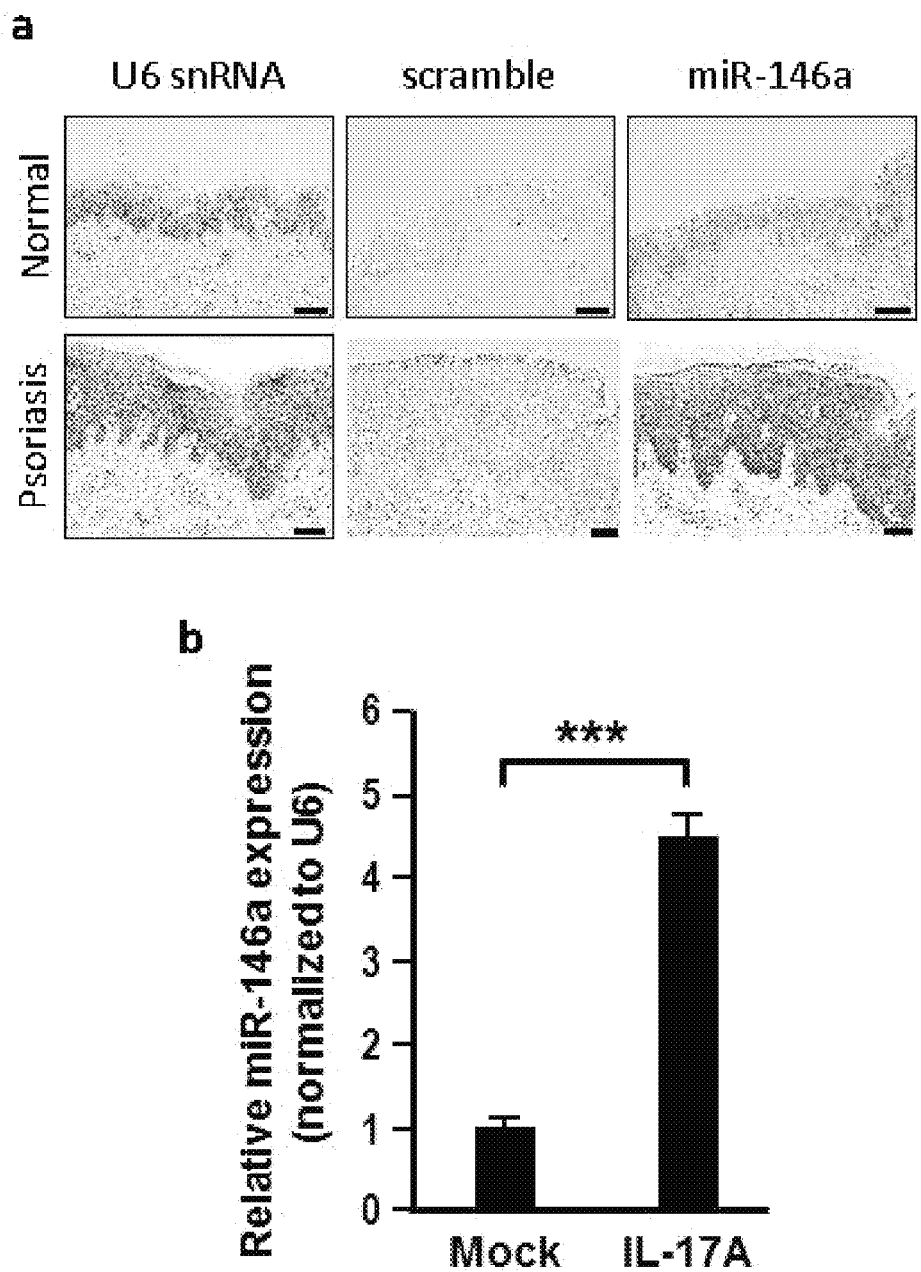
FIG. 3. MicroRNA-146a promoted expression of IL-6 and IL-8 is upregulated in galectin-7 knockdown cells and in the epidermis of psoriatic lesions. Panel a: MiR-146a in the epidermis of normal and psoriatic keratinocytes was detected by RNA in situ hybridization assay (ISH). Scale bar: 100 m. Panel b: The miR-146a level in HaCaT cells treated with IL-17A was quantified by real-time PCR. Panels c and d: The secretion of cytokines (IL-6 and IL-8) by HaCaT cells stably transfected with pmiR or pmiR-146a vectors was measured 2 days after stimulation with 25 or 100 ng/ml IL-17A. For statistical analysis, each group was compared to the mock (0 ng/ml) pmiR group; ns: not significant, *P<0.05.
Figure 3:
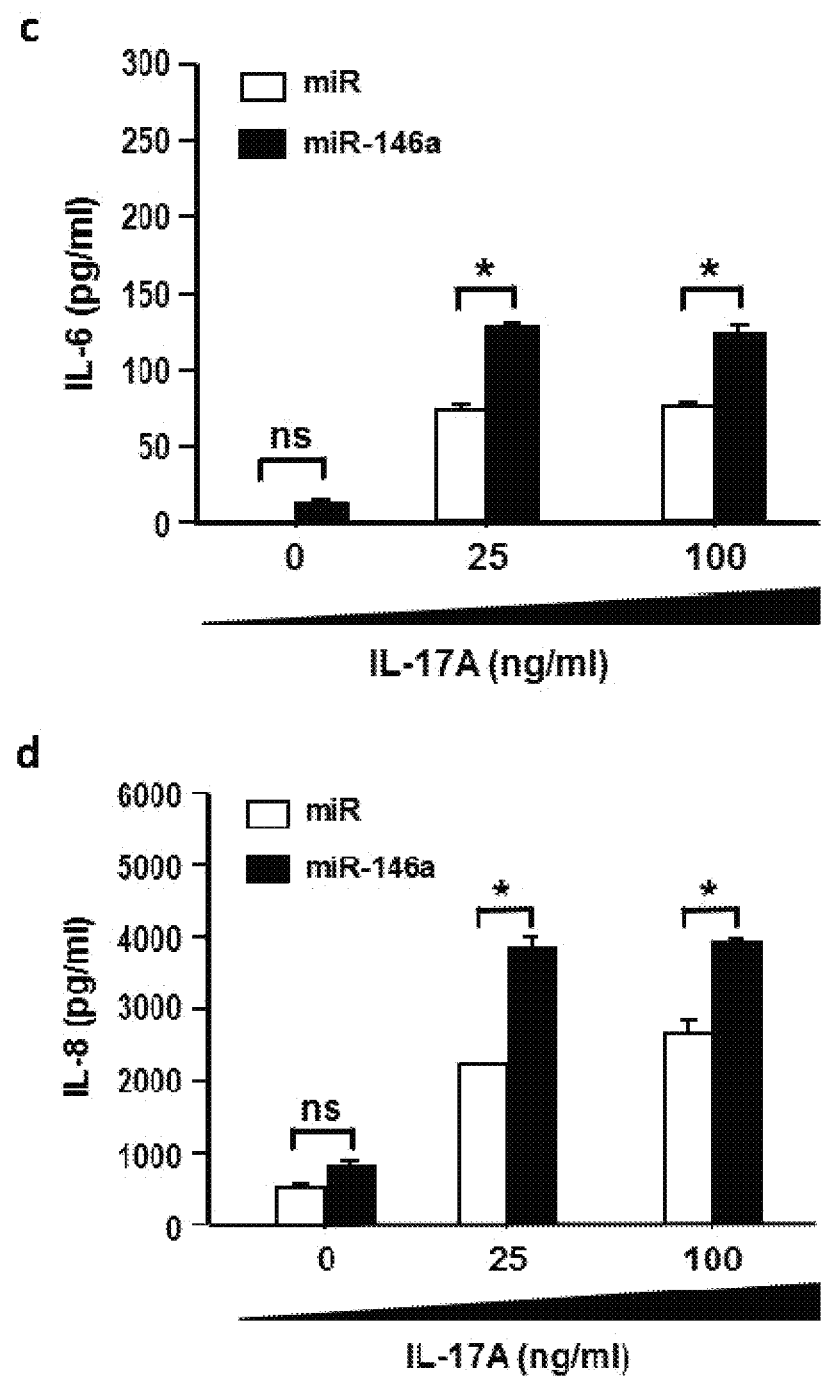

Example 3 MiR-146a Expression in Keratinocytes is Suppressed by Galectin-7 and Induced by IL-17A It is found that miR-146a is upregulated in galectin-7 knockdown HaCaT cells via microarray analysis, deep sequencing, and real-time PCR analyses (data not shown). Similarly, miR-146a was significantly overexpressed in HEKn cells with a transient galectin-7 knockdown (data not shown). In situ hybridization using locked nucleic acid (LNA)-modified nucleotide probes was performed, and the results demonstrated that miR-146a was expressed in the epidermis of normal human skin but rather weakly (FIG. 3, Panel a). MiR-146a expression was greatly increased in all epidermal layers in psoriatic lesions compared to healthy human skin (FIG. 3, Panel a). To determine whether IL-17A affects the expression of miR-146a, HaCaT and HEKn cells were respectively treated with IL-17A. The data indicated that IL-17A induced miR-146a expression in keratinocytes (FIG. 3, Panel b).

Next, keratinocytes stably overexpressing miR-146a were generated so as to investigate the effects of miR-146a under inflammatory conditions. It is noticed that overexpression of miR-146a in HaCaT cells did not affect galectin-7 expression (data not shown). Overexpression of miR-146a markedly enhanced production of IL-6 and IL-8 after IL-17A stimulation, as compared with control cells (FIG. 3, Panels c and d).

Figure 4:
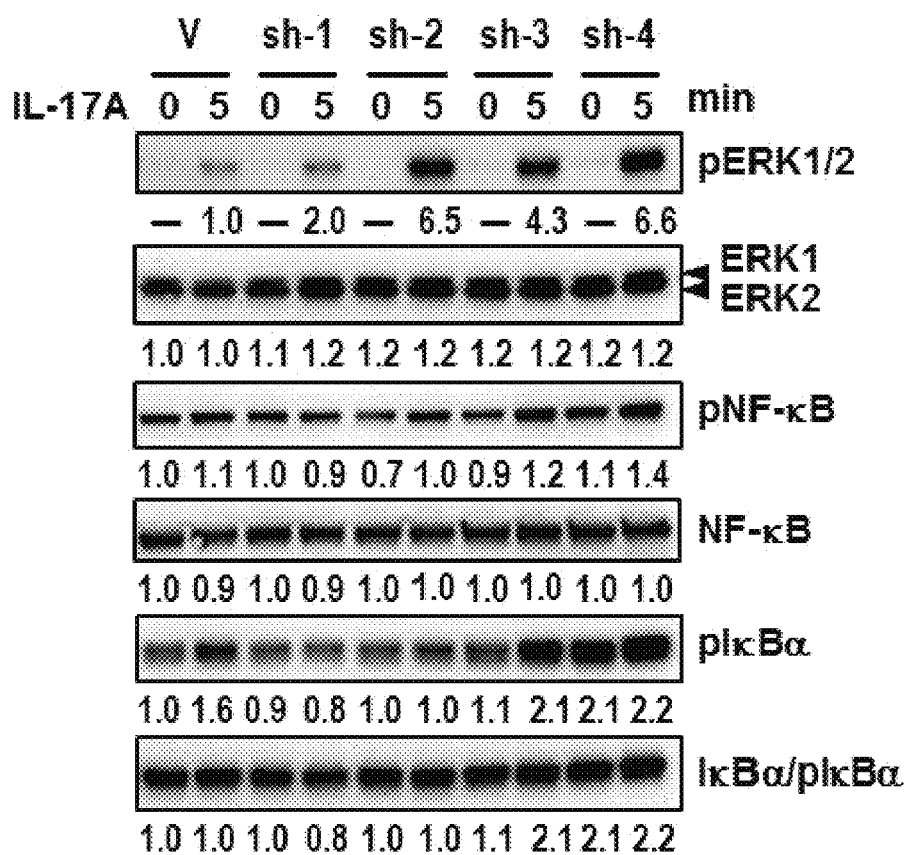
FIG. 4. The expression of proinflammatory cytokines is regulated by galectin-7 and miR-146a via ERK1 and ERK2 signaling pathway. Panel a: Galectin-7 knockdown HaCaT cells and control cells were treated with IL-17A for 5 minutes, and cell lysates were prepared and analyzed by immunoblotting. Total ERK1, ERK2, NF-κB, and IκBα and their phosphorylated forms were detected with the corresponding antibodies. Panel b: HaCaT cells stably transfected with pmiR (control vector) or pmiR-146a were treated with IL-17A. Immunoblotting was performed as described in Panel a. Protein quantification data on phospho-ERK1 (pERK1) and phospho-ERK2 (pERK2) were normalized to the control cells treated with IL-17 for 5 minutes. Data on total protein levels and levels of phosphorylated NF-κB and IκBα and on the total protein levels of ERK1 and ERK2 were normalized to the control cells (treated with IL-17 for 0 minute).
Figure 4:
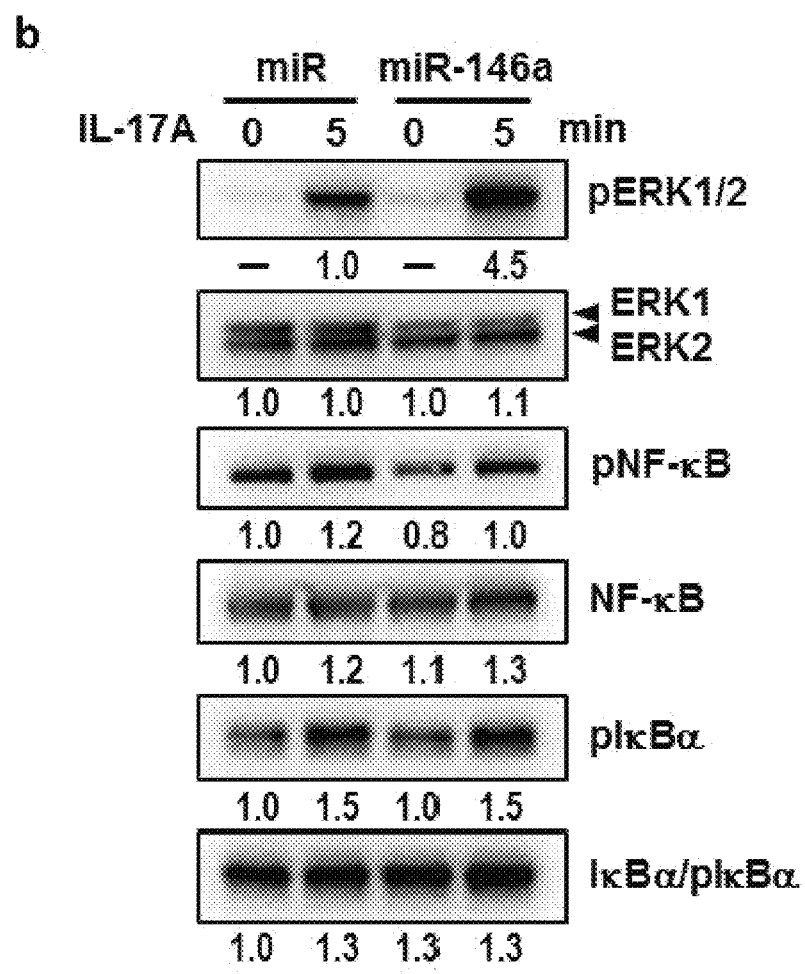

Example 4 Galectin-7 Knockdown Activates the IL-17-Induced MAPK ERK Signaling Pathway In response to IL-17A exposure, both the MAPK and NF-κB pathways participate in the production of proinflammatory cytokines in keratinocytes. To further dissect the mechanism underlying the involvement of galectin-7 in psoriasis pathogenesis, the IL-17A signaling pathway was investigated in this example. To distinguish whether galectin-7 affects MAPK or NF-κB activation, HaCaT cells were starved overnight in serum-free medium and then incubated the cells in the presence or absence of IL-17A. The results of immunoblotting analysis demonstrated that resting cells contained small amounts of phosphorylated extracellular signal-related kinase 1 and extracellular signal-related kinase 2 (phospho-ERK1 and phospho-ERK2, respectively; FIG. 4, Panel a). In contrast, exposure of cells to IL-17A induced strong phosphorylation of ERK1 and ERK2 in four galectin-7 knockdown cell lines (sh-1, sh-2, sh-3, and sh-4): 2.0- to 6.6-fold increases as compared with control cells (FIG. 4, Panel a). The total ERK1 and ERK2 proteins were expressed at comparable levels in all cells with or without IL-17A stimulation.

In contrast, the upstream components of the NF-κB pathway (including phospho-NF-κB, total NF-κB, phospho-IκBα, and total IκBα) remained unchanged in response to IL-17A (FIG. 4, Panel a), suggesting that galectin-7 does not mediate activation of the NF-κB pathway. Specific chemical inhibitors, including MAP kinase p38 inhibitor (SB203580), INK inhibitor (SP600125), NF-κB inhibitor (PDTC), phosphatidylinositol 3-kinase (PI3K) inhibitor (LY294002), and MAPK/ERK inhibitor (PD98059) were used to target their corresponding pathways in galectin-7 knockdown keratinocytes after stimulation with IL-17A. Among these compounds, the MAPK ERK inhibitor PD98059 significantly blocked IL-6 and IL-8 production induced by IL-17A (data not shown). IL-17A-induced IL-6 and IL-8 secretion was not blocked by inhibitors of MAP kinases p38 (SB203580), INK (SP600125), NF-κB (PDTC), or by the inhibitor of phosphatidylinositol 3-kinase (PI3K; LY294002; data not shown). The data suggested that the regulatory role of galectin-7 in IL-17A-induced cytokine expression is primarily mediated by its effect on the MAPK ERK signaling pathway via suppression of ERK phosphorylation.

Example 5 MiR-146a Induces Inflammatory Mediators in Keratinocytes Through the MAPK ERK Pathway To identify the intracellular pathways via which miR-146a increases the expression of proinflammatory cytokines after stimulation by IL-17A, the activation of the MAPK and NF-κB pathways in miR-146-overexpressing keratinocytes was examined in this example. As shown in Panel b of FIG. 4, the MAPK ERK pathway was highly activated by IL-17A in miR-146a-overexpressing cells, when compared with control cells. It is also found that ERK phosphorylation was significantly enhanced (more than fourfold, $P<0.01$; FIG. 4, Panel b). In line with the data from galectin-7 knockdown cells, there were no obvious differences in phosphorylation of NF-κB and IκBα or their total protein levels between the miR-146a-overexpressing cells and control cells (FIG. 4, Panel b). Collectively, these results suggested that miR-146a promotes IL-17A-induced production of IL-6 and IL-8 through the MAPK ERK pathway.

Figure 5:
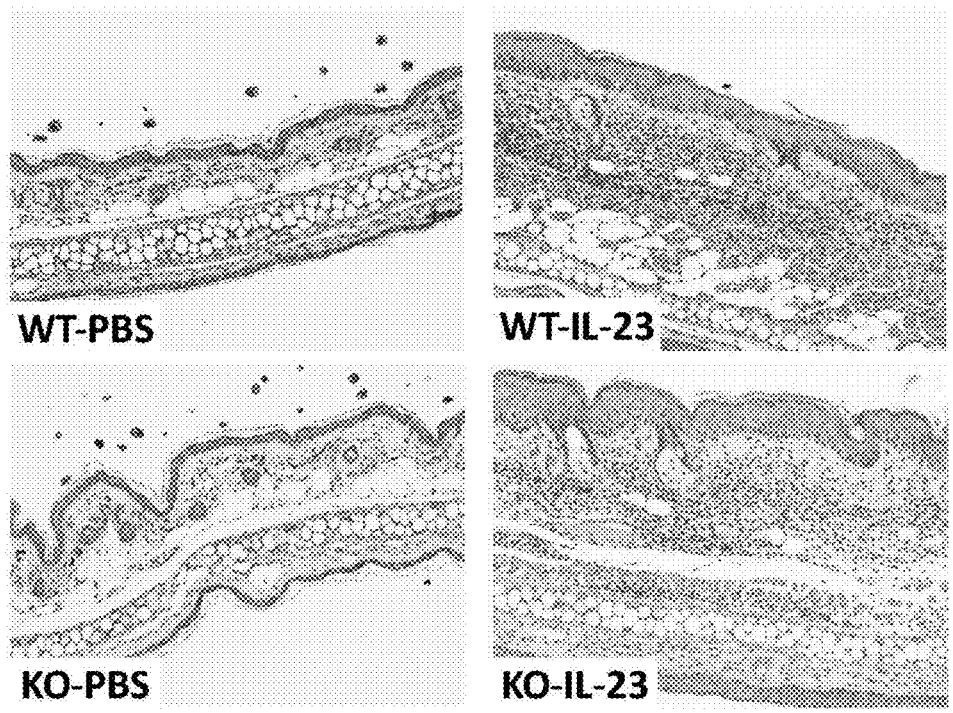
FIG. 5. Galectin-7-deficient mice exhibit hyperproliferative keratinocytes and increased immune-cell infiltration. Panel a: H&E staining of ear sections isolated from IL-23-injected or PBS-injected WT or galectin-7-deficient (knockout; KO) mice. Scale bar: 50 m. Panel b: Ear thickness of WT and galectin-7-deficient (KO) mice was measured every other day for 15 days after IL-23 or PBS injection (WT/PBS, n=5; WT/IL-23, n=18; KO/PBS, n=5, KO/IL-23, n=19). For statistical analysis, ear thickness of KO-IL-23 at each time point was compared with that in the corresponding WT-IL-23 group. Panel c: Epidermal thicknesses of WT and KO mice were quantified on histological slides 15 days after IL-23 or PBS injection in the same mice as described in Panel b. Panel d: Leukocytes were counted in 400× magnified visual fields of tissue sections isolated from IL-23-injected mice (WT, n=6; KO, n=5); ns: not significant, $P<0.01$, *$P<0.001$.
Figure 5:
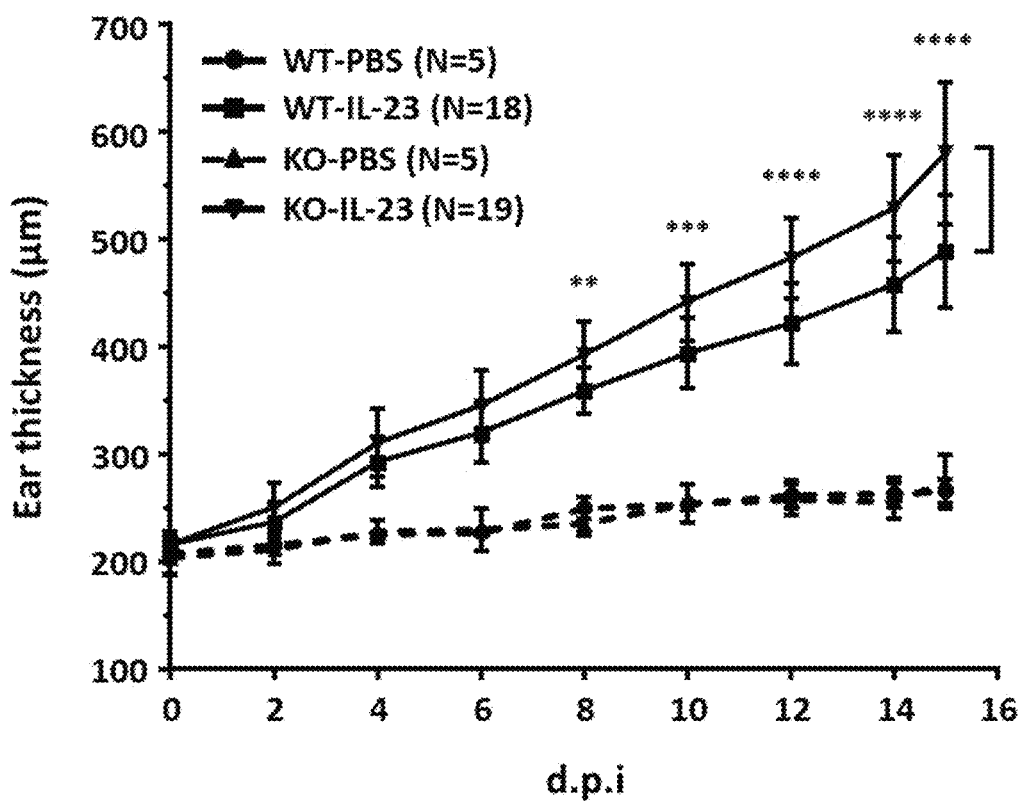
Figure 5:
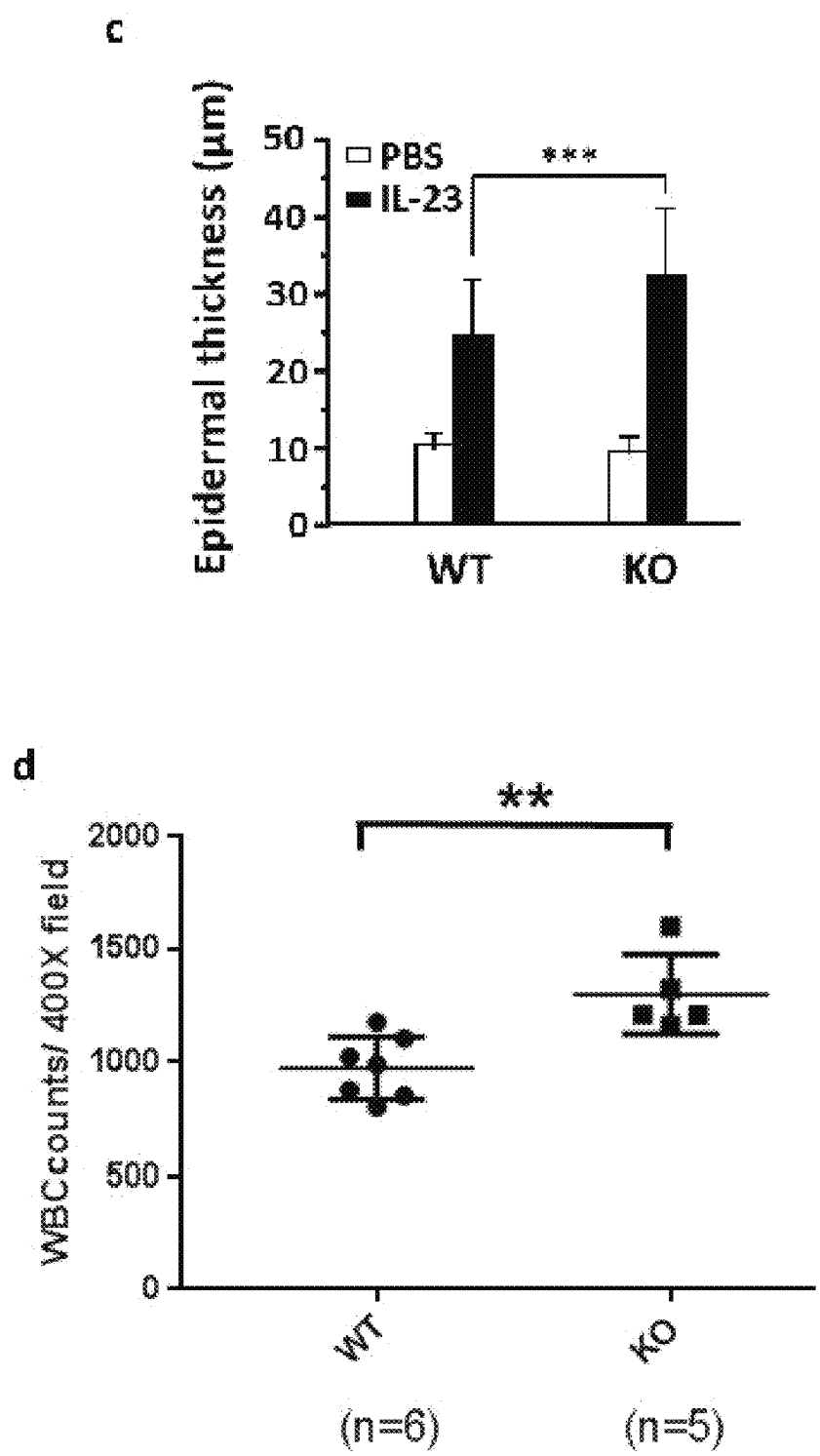

Example 6 Galectin-7-Deficient Mice are More Prone to Develop IL-23-Induced Psoriasiform Dermatitis and Manifest Intensified Epidermal Hyperplasia, Inflammation To further assess the participation of galectin-7 in the regulation of inflammatory responses in vivo, galectin-7-deficient mice were studied to determine the role of galectin-7 in IL-23-induced skin inflammation. In response to IL-23 stimulation, WT mice showed ear swelling resulting from hyperplasia of epidermal keratinocytes and leukocytes infiltration as revealed by H&E staining (FIG. 5, Panel a). Skin sections from galectin-7-deficient mice showed greater increases in ear and epidermal thickness compared with their littermate WT controls on day 14 after IL-23 injection (FIG. 5, Panels b and c). In addition, the number of infiltrating leukocytes significantly increased in galectin-7-deficient mice (FIG. 5, Panel d). In microarray analysis, it is also found that the amounts of proinflammatory-cytokine mRNAs (IL-17A, CXCL5, and IL-19) were elevated in galectin-7-deficient mice when compared with WT mice (Table 1).

TABLE 1

Microarray data of WT mice with IL-23 injection

| PBS, WT | PBS, KO | IL-23, WT | IL-23, KO | Gene Name |
|---|---|---|---|---|
| 1.00 | −1.12 | 2.89 | 3.01 | keratin 6B |
| 1.00 | −1.80 | 1.33 | 2.54 | interleukin 17A |
| 1.00 | 2.47 | 1.06 | 3.38 | chemokine (C-X-C motif) ligand 5 |
| 1.00 | 1.60 | 8.83 | 9.50 | S100 calcium binding protein A8 (calgranulin A) |
| 1.00 | 1.35 | 5.05 | 5.31 | S100 calcium binding protein A9 (calgranulin B) |
| 1.00 | 1.52 | 5.92 | 14.61 | interleukin 19 |

Taken together, these results indicate that galectin-7 has a suppressive effect on keratinocyte-mediated inflammatory responses.

Figure 6:
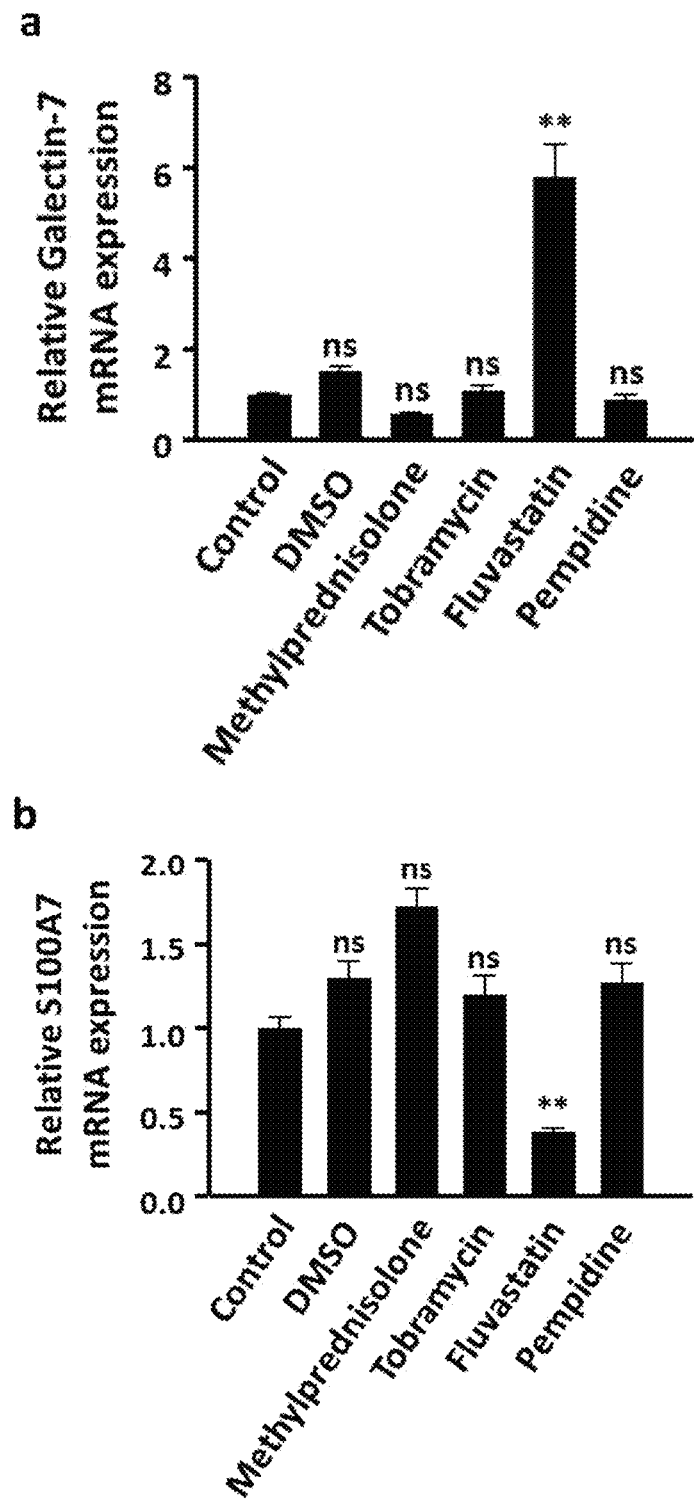
FIG. 6. Fluvastatin increases galectin-7 levels in keratinocytes and attenuated IL-23 induced epidermal thickness. Panels a and b: Real-time PCR analysis of mRNA expression of galectin-7 and S100A7 in HaCaT cells treated with methylprednisolone (10.6 µM), tobramycin (8.6 µM), fluvastatin (9.2 µM), pempidine (13 µM), or vehicle control (dimethyl sulfoxide; DMSO) for 24 hours. The relative fold changes were calculated by the ΔΔCt method; data from all the samples were normalized to the mock sample, and GAPDH served as an endogenous control. Panels c and d: Production of cytokines IL-6 and IL-8 by HaCaT cells treated for 2 days with fluvastatin (fluva, 9.2 µM) with or without IL-17A (200 ng/ml) was measured by ELISA. In statistical analysis, each group was compared with its mock treatment control (without IL-17A, DMSO, or fluvastatin treatment). In addition, in the presence IL-17A, the mock group was compared with DMSO and fluvastatin groups for statistical analysis. Panel e: Immunoblotting analysis of galectin-7 in keratinocytes treated with TNF-α and IL-17A with or without fluvastatin. Panel f: Ear thickness of different groups of mice subjected to intradermal injections of IL-23 or PBS, and treated with fluvastatin, pravastatin, or saline. ns: not significant, *$P<0.05$, $P<0.01$, *$P<0.001$.
Figure 6:
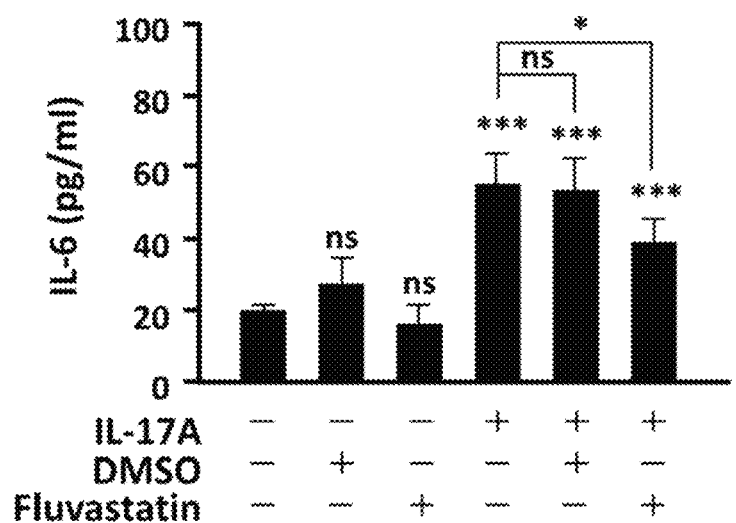
Figure 6:
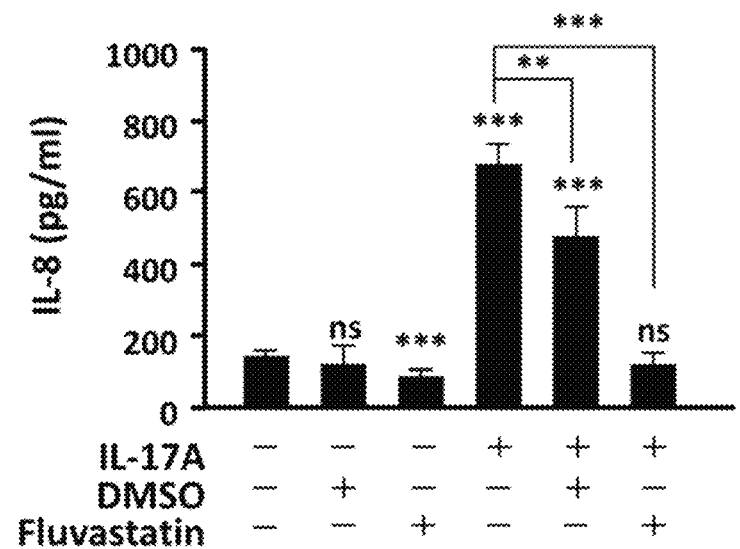
Figure 6:
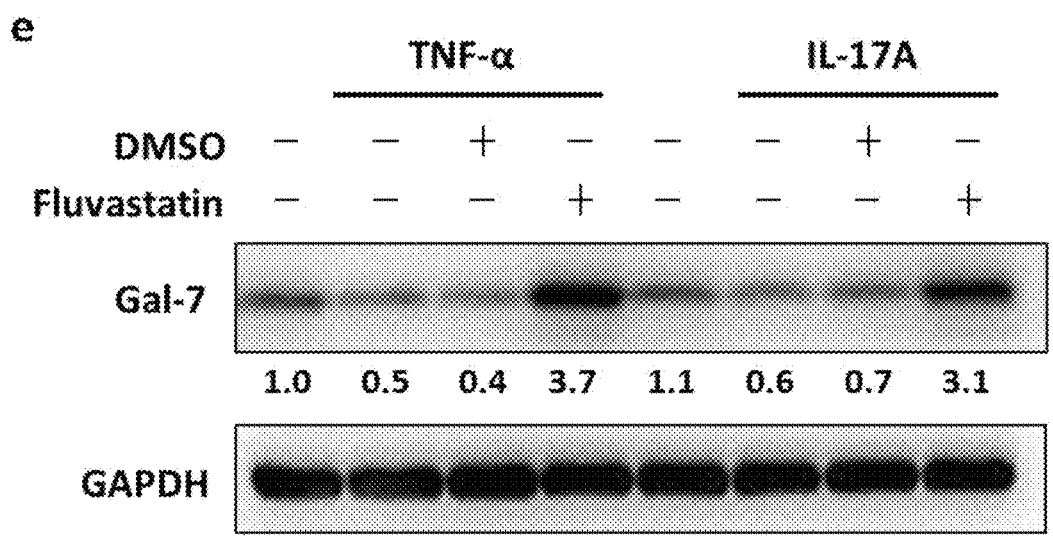
Figure 6:
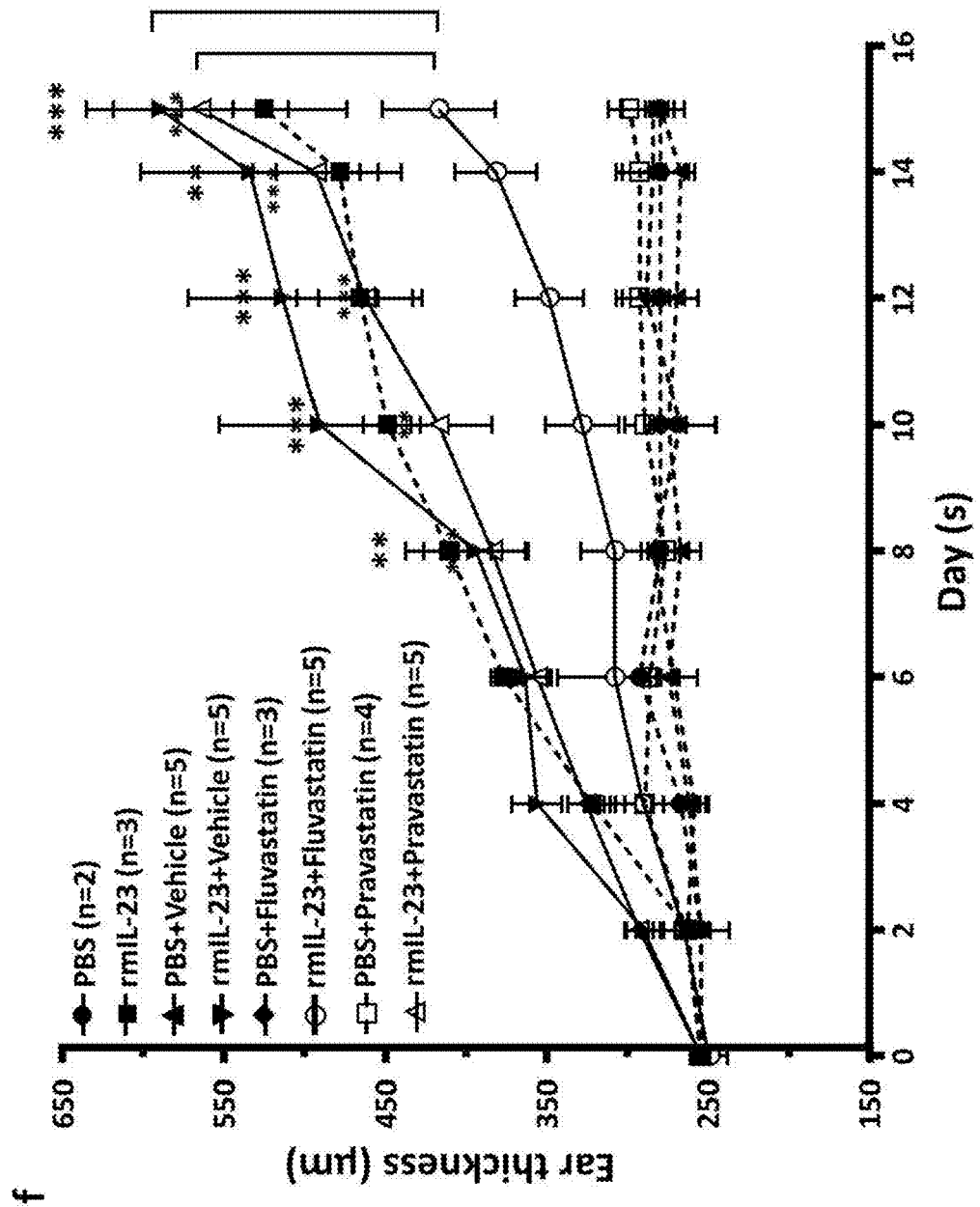

Example 7 Fluvastatin Increases Galectin-7 Levels and Suppresses Production of Proinflammatory Cytokines in Keratinocytes, and Attenuated IL-23 Induced Epidermal Thickness In Vivo To exploit the observations on the anti-inflammatory and antiproliferative effects of galectin-7, microarray databases were scrutinized for approved drugs that can induce galectin-7 expression. Four compounds were identified by connectivity map data (cMAP) analysis: methylprednisolone, tobramycin, fluvastatin, and pempidine. Among them, only fluvastatin induced galectin-7 mRNA and protein expression (FIG. 6, Panel a) and reduced S100A7 mRNA expression (FIG. 6, Panel b). Time-lapse analysis of fluvastatin-treated keratinocytes revealed suppression of cell proliferation; this suppression correlated with p21 overexpression as revealed by immunoblot analysis (data not shown). The influence of other statin drugs were next examined, and the data indicated that atorvastatin, cerivastatin, pitavastatin, lovastatin, mevastatin, and simvastatin all induced galectin-7 expression (data not shown). It is found that fluvastatin attenuated IL-17A-induced IL-6 and IL-8 secretion (FIG. 6, Panels c and d). Further, fluvastatin enhanced galectin-7 expression above the basal levels, even in the presence of cytokines (TNF-α and IL-17A) that suppress galectin-7 expression (FIG. 6, Panel e).

The effect of fluvastatin or pravastatin on psoriasis was further confirmed in animal models, in which fluvastatin, rather than pravastatin, attenuated IL-23 induced ear skin thickening and keratinocyte hyperplasia (FIG. 6, Panel f).

In sum, these results demonstrated that statin drugs, especially fluvastatin, are potent galectin-7 inducers that suppress IL-17A and IL-23 induced cytokine production and skin hyperplasia.

Example 8 Galectin-7 Expression is Correlated to EGFR Mutations in Lung Cancer

Galectin-7 in human is encoded by galectin-7 gene. In this example, the relationship between the expressed level of galectin-7 and EGRF signaling in various lung cancer cell lines was investigated.

Figure 7:
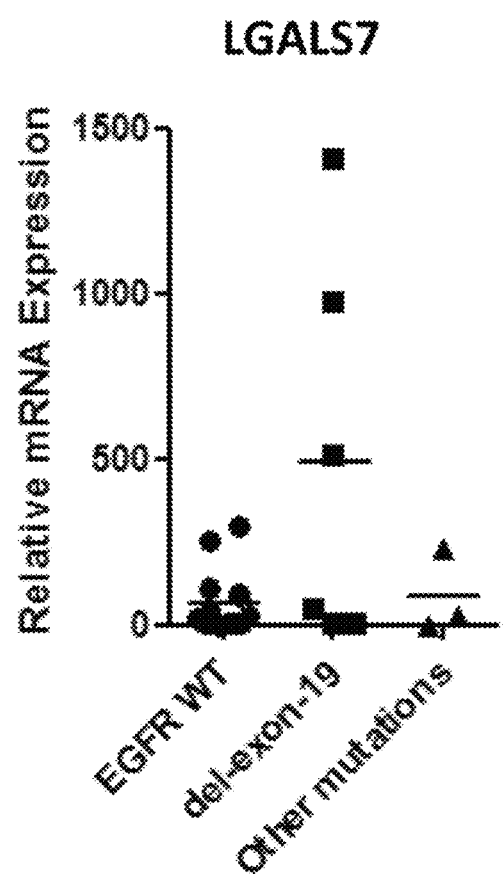
FIG. 7. Activating EGFR mutations increased galectin-7 expression in lung cancer. Panel a, galectin-7 mRNA levels in 21 lung cancer cell lines with distinct activating EGFR mutations were measured by qPCR (n=4). The relative mRNA expressions were calculated using the ΔΔCt method and normalized to an endogenous control (GAPDH) and the Ct value of the mock sample. Panels b and c, lung cancer cells were treat with 10 µM TKIs, gefitinib, or the EGFR inhibitor, for 24 hours. Protein expression of p-EGFR, p-ERK, p-Akt in endogenous (Panel b), and in ectopically overexpressed galectin-7 (Panel c) were measure by immunoblot assay. Panel d, lung cancer cells were starved overnight before stimulating with 10 ng/ml EGF for indicated times, and protein levels of galectin-7 were measured by immunoblot assay. All the immunoblot experiments were done at least in triplicate and the relative fold changes of galectin-7 were calculated and normalized to the control.
Figure 7:
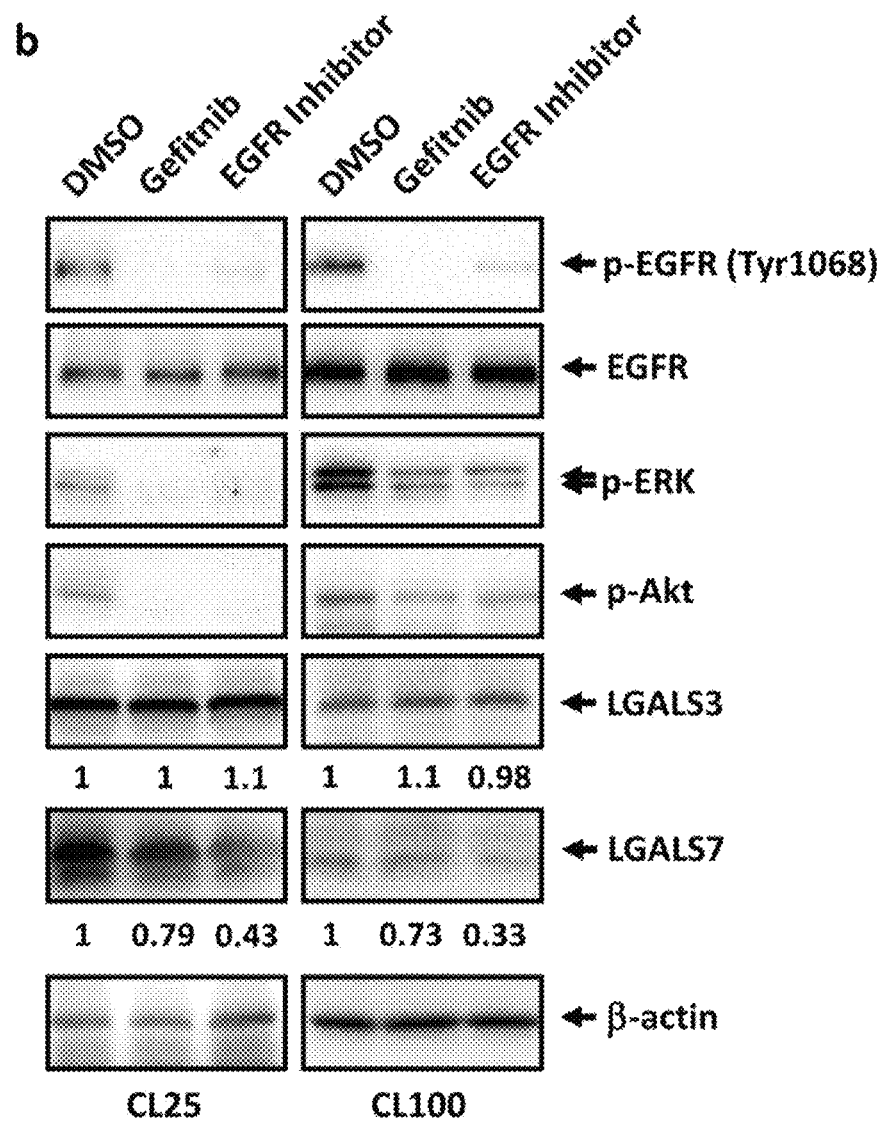
Figure 7:
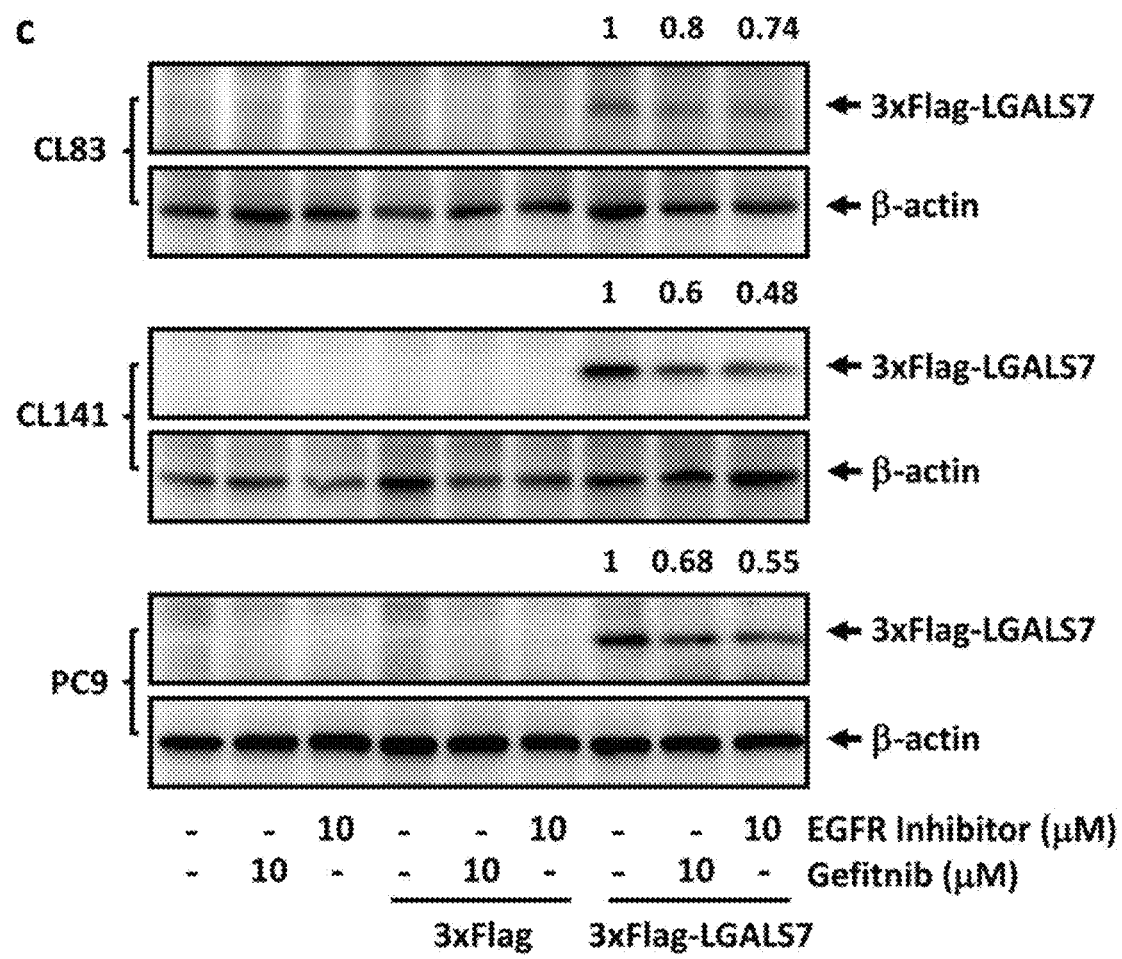
Figure 7:
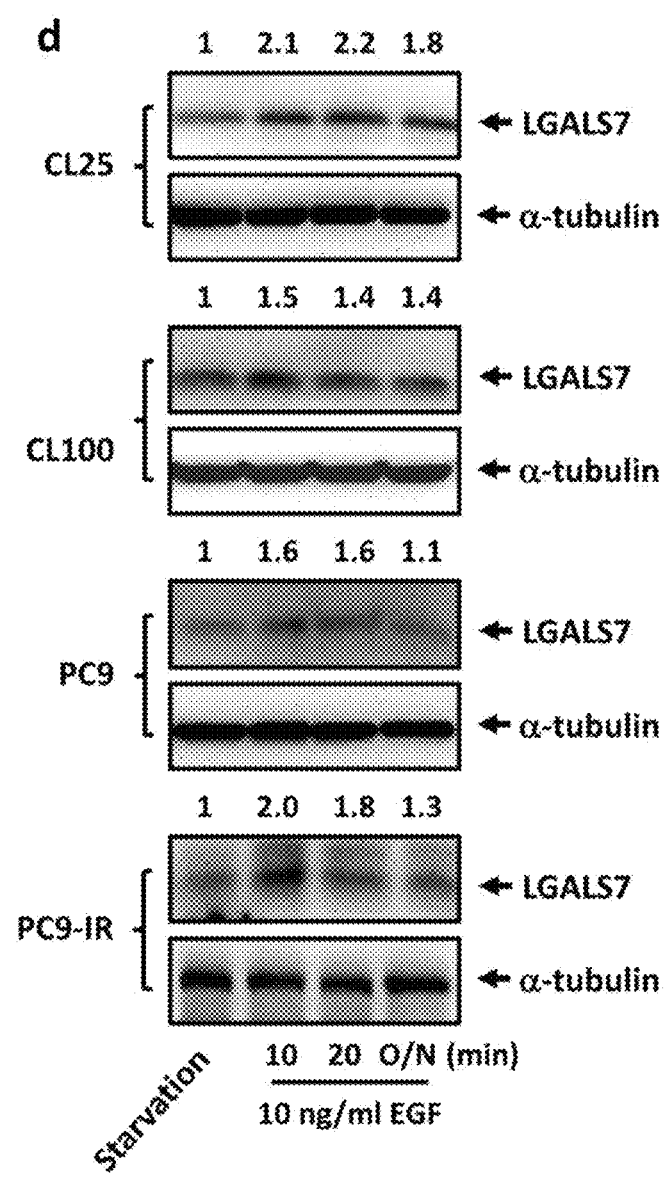

Galectin-7 mRNA levels in 21 lung cancer cell lines were measured by quantitative real-time PCR (qPCR). It was found that approximately one-third of the cell lines exhibited above-background level of galectin-7; three of six cell lines with EGFR mutation (i.e., EGFR exon 19 deletion) exhibited exceedingly high levels of galectin-7 (FIG. 7, Panel a).

To characterize the relationship between galectin-7 expression and EGFR signaling, two of the cell lines, CL25 and CL100, were exposed to a tyrosine kinase inhibitor (TKI) (e.g., gefitinib) and an EGFR inhibitor, to block EGFR activation. It was found that galectin-7 was downregulated after the treatment (FIG. 7, Panel b). Similarly, for cell lines having ectopically overexpressed galectin-7, such as CL83, CL141, and PC9 cells, the level of galectin-7 in each cell line was also downregulated after the treatment (FIG. 7, Panel c). In contrast, activation of EGFR signaling by epidermal growth factor (EGF) transiently upregulated galectin-7 expression in CL25, CL100, PC9, and PC9-IR (FIG. 7, Panel d).

The galectin-7 expression in tumors from patients with variable stages of lung adenocarcinoma was determined by IHC staining. Among the 189 patients in this analysis, 35 exhibited positive staining (18.5%). In addition, galectin-7 expression was significantly associated with activating EGFR mutations (P=0.0025), including deletions in exon19 and the L858R mutation (Table 2). Further, tumors from 27 out of 102 patients (26.5%) in the EGFR mutation group were positive for galectin-7, while only 8 out of 87 patients (9.2%) were positive in the wild-type EGFR group. In addition, a significant association of galectin-7 expression with deletions in exon 19 of EGFR (P=0.0006), but not with the L858R mutation (P=0.0824) (Table 3) was illustrated.

TABLE 2

Clinical characteristics of EGFR mutation analyses in 189 patients

| Variables | EGFR Mutation (−) N = 87 (%) | EGFR Mutation (+) N = 102 (%) | p[a] |
|---|---|---|---|
| | Galectin-7 | | |
| (−) | 79 (90.8%) | 75 (73.5%) | 0.0025 |
| (+) | 8 (9.2%) | 27 (26.5%) | |

[a]p value from Fisher's exact test.
[b]Patients with exon 19 deletion or L858R mutation were both included.

TABLE 3

Galectin-7 expression analyses in 189
patients with lung adenocarcinoma

| Variables | Galectin-7 (−)<br>N = 154 (%) | Galectin-7 (+)<br>N = 35 (%) | p[a] |
|---|---|---|---|
| EGFR mutation | | | |
| (−) | 79 (51.3%) | 8 (22.9%) | |
| Exon 19 deletion | 30 (19.5%) | 16 (45.7%) | 0.0006 |
| L858R | 45 (29.2%) | 11 (31.4%) | 0.0824 |

[a]p value from Fisher's exact test.

Example 9 Galectin-7 Negatively Regulates Lung Cancer Cell Progression

Figure 8:
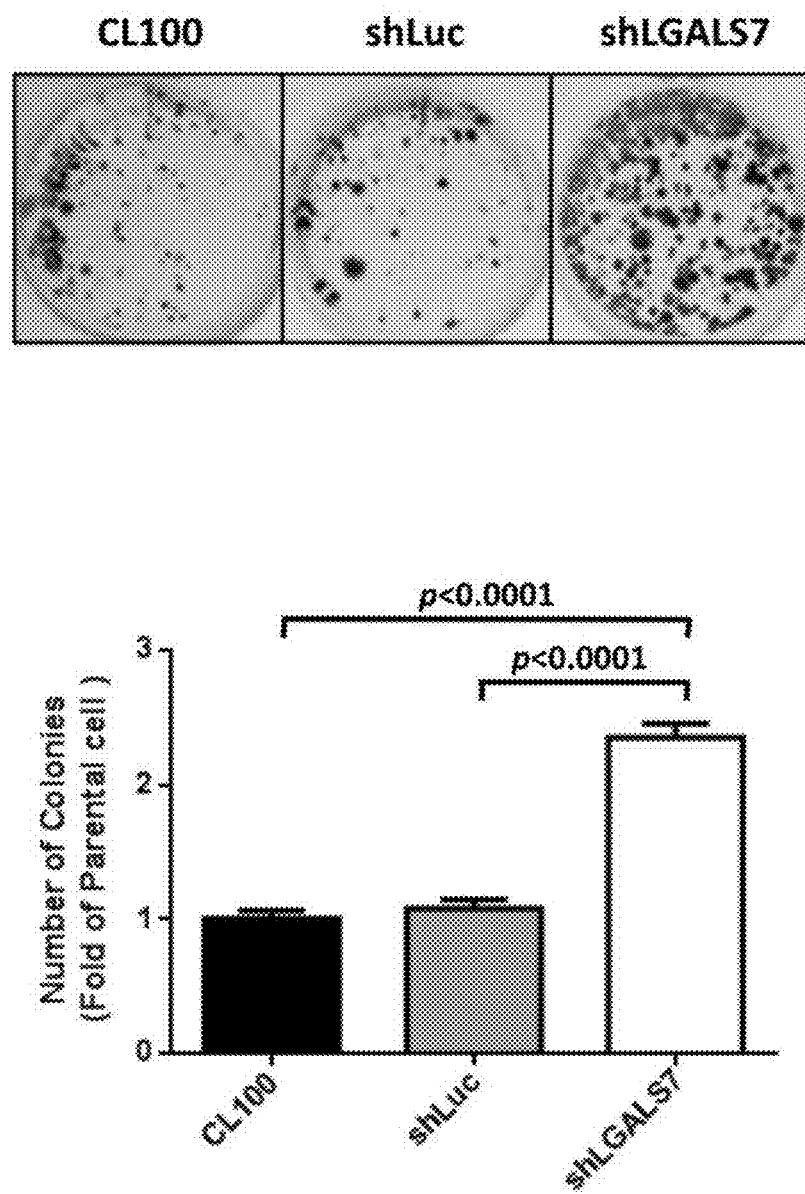
FIG. 8. Knockdown of galectin-7 enhanced colony formation and sphere formation. Panel a, control and galectin-7 knockdown CL100 cells were seeded in 24-well plate at the density of 200 cells/well. After 14 days incubation, cells were fixed and stained using 0.05% crystal violet solution (n=5). Panels b and c, control and galectin-7 knockdown CL100 cells were suspended in stem cell culture medium and seeded in ultra-low attachment 24-well plate. After 12 days incubation, sphere number and diameter were counted and analyzed under a microscope (n=3).
Figure 8:
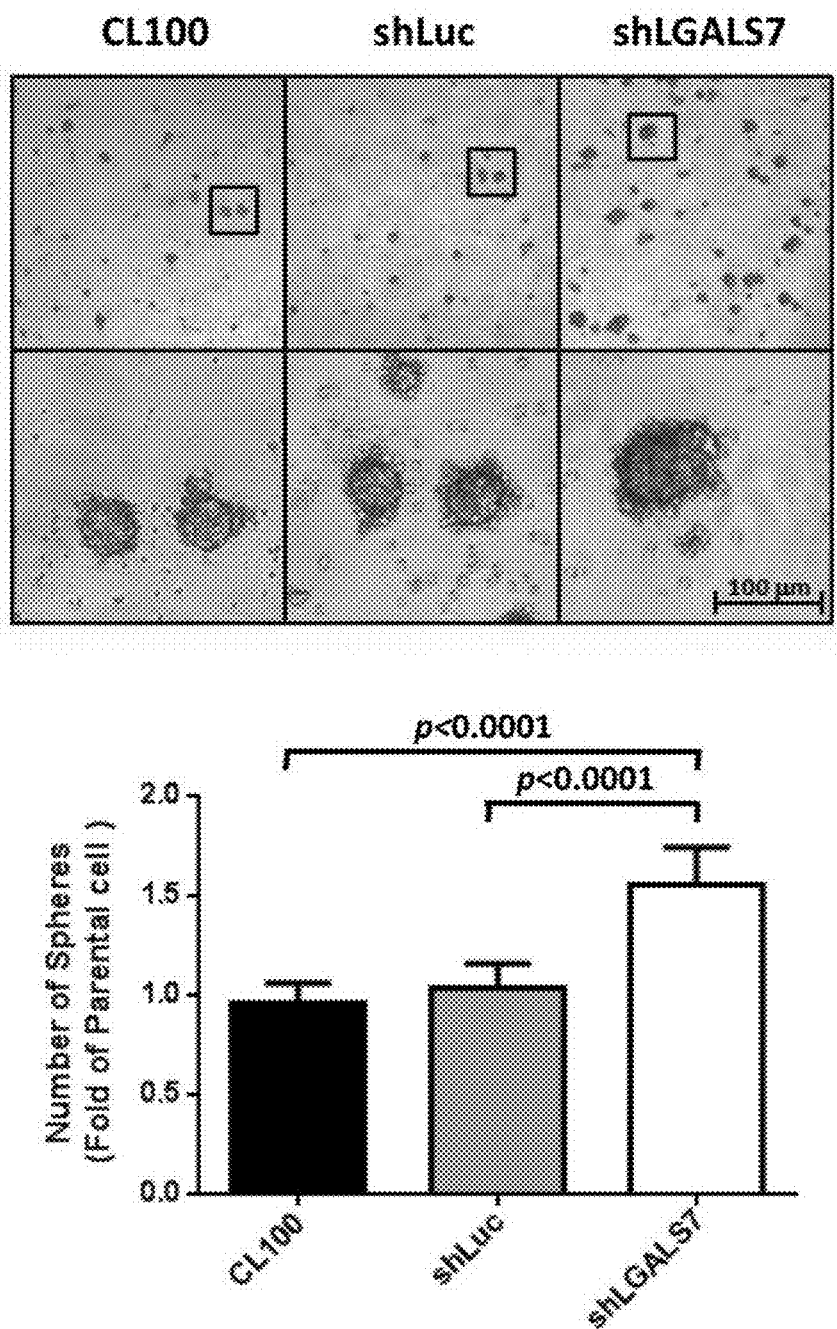
Figure 8:
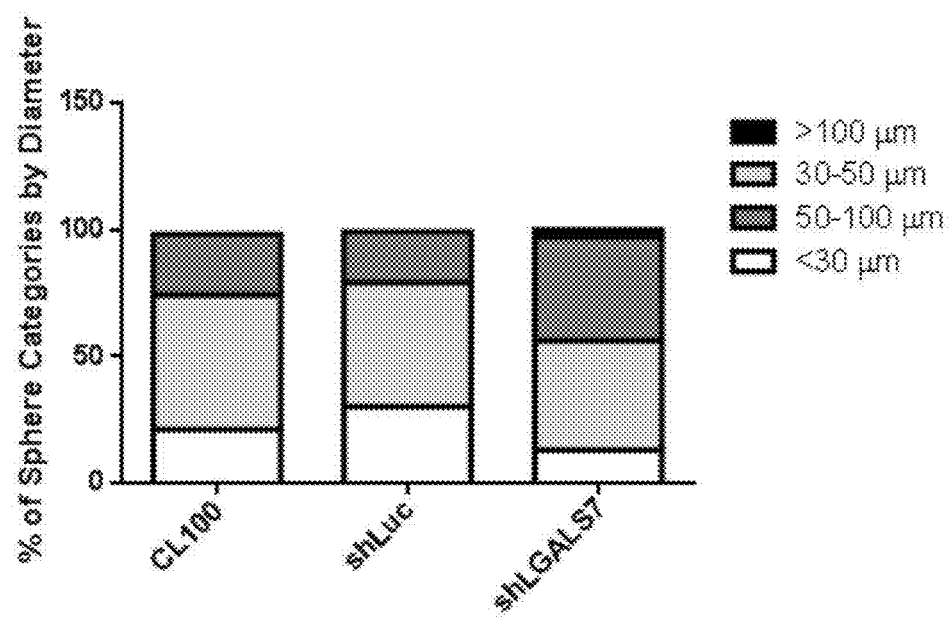

To study the role of galectin-7 in lung cancer, effects of galectin-7 expression on several cellular functions, including cell proliferation, colony formation, sphere formation, and cell migration were performed. Cell proliferation was not affected by altered expression of galectin-7 (data not shown), but the ability of colony formation and sphere formation (i.e., the number of both of the colonies and the spheres) were increased as galectin-7 was knockdown (FIG. 8, Panels a and b). In addition, the enlarged size of the spheres were generated from lung cancer stem cells (FIG. 8, Panel c).

Figure 9:
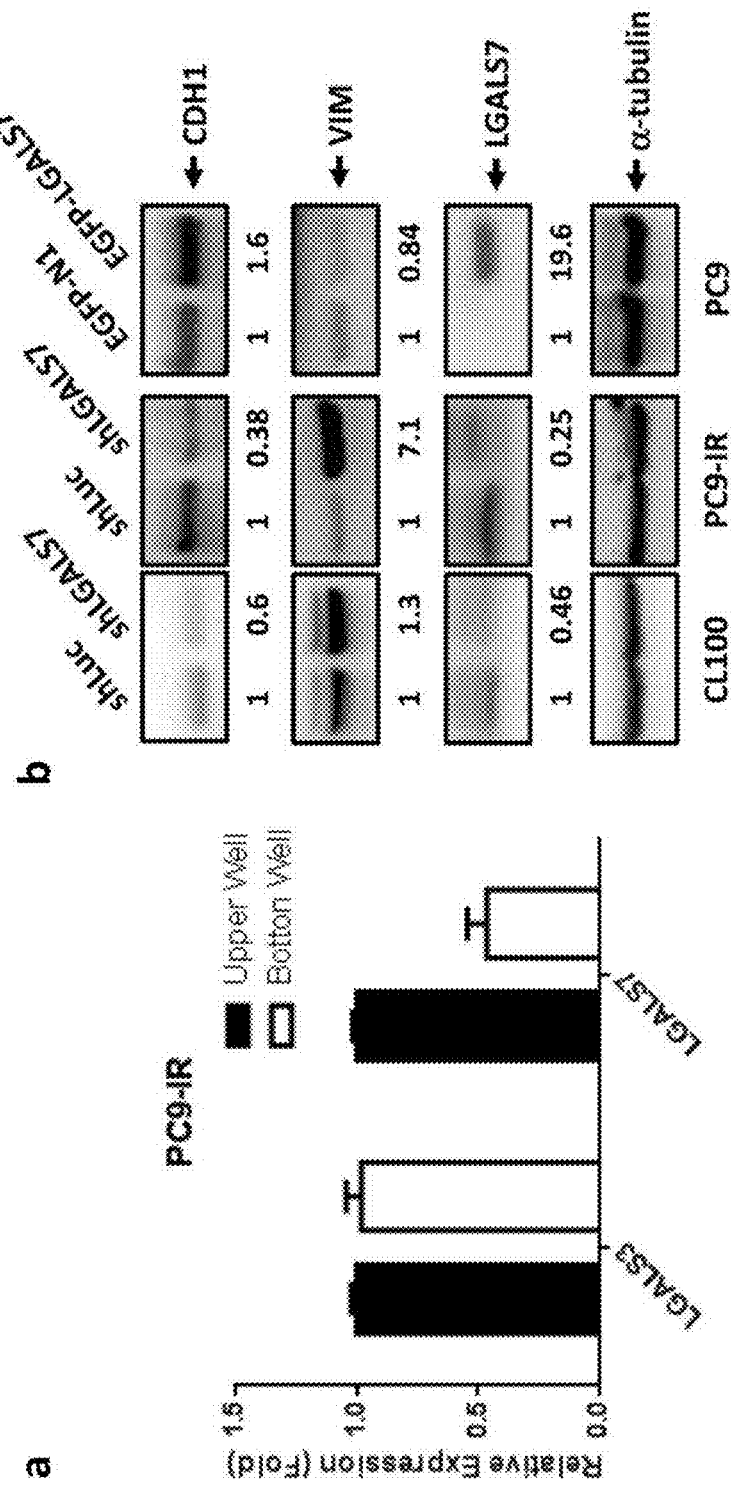
FIG. 9. Galectin-7 suppressed lung cancer cells migration. Panel a, $10^6$ PC9-TR cells were seeded in transwell culture plates for 16 hours. After incubation, the mRNA of the cells from the upper and bottom wells were collected and analyzed by qPCR (n=4). Protein expression of CDH1, VIM, and galectin-7 were measured by immunoblot (Panel b); migration ability was measured by transwell migration assay (Panel c), single cell migration assay (n=3) (Panel d), and wound healing assay (n=4) (Panel e) in control, galectin-7-overexpressing (EGFP-LGALS7), and galectin-7 knockdown (shLGALS7) lung cancer cells. All immunoblot experiments were done at least in triplicate and the relative fold changes of CDH1, VIM, and galectin-7 were calculated and normalized to the control.
Figure 9:
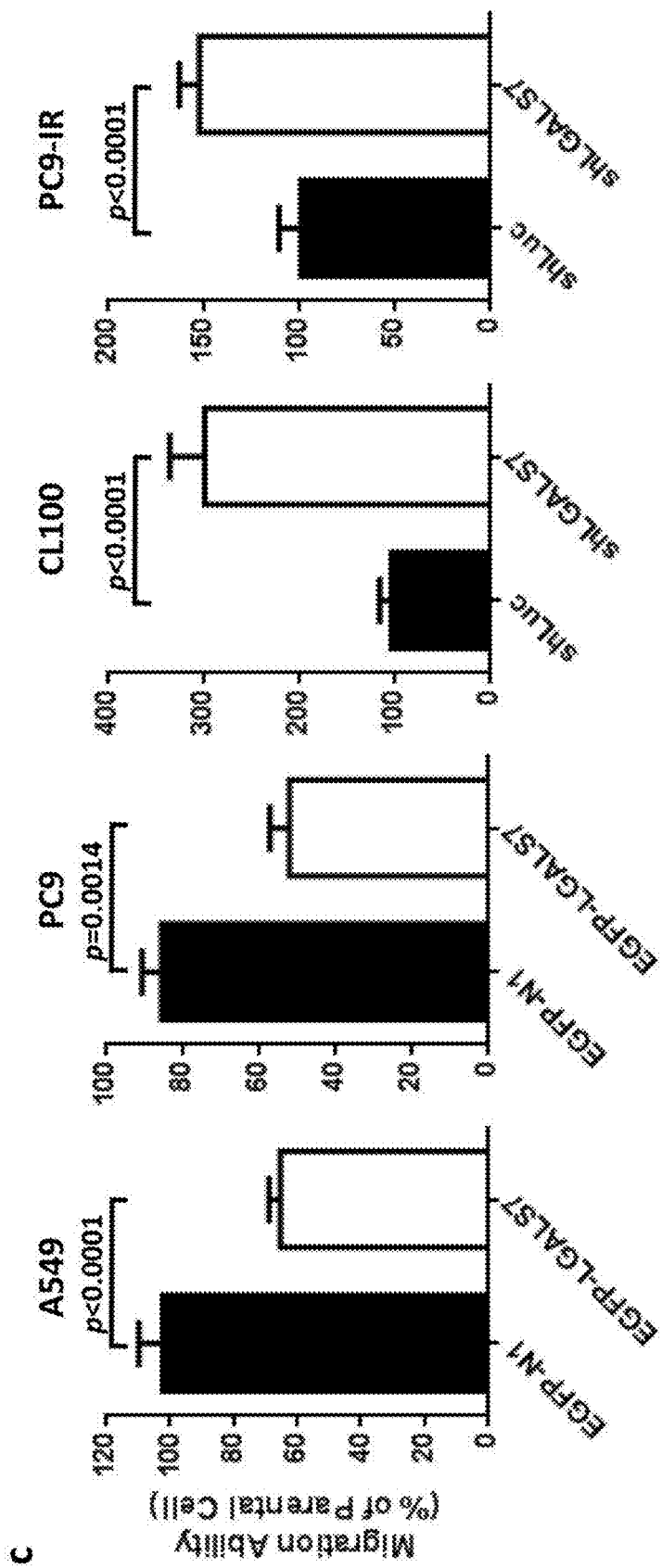
Figure 9:
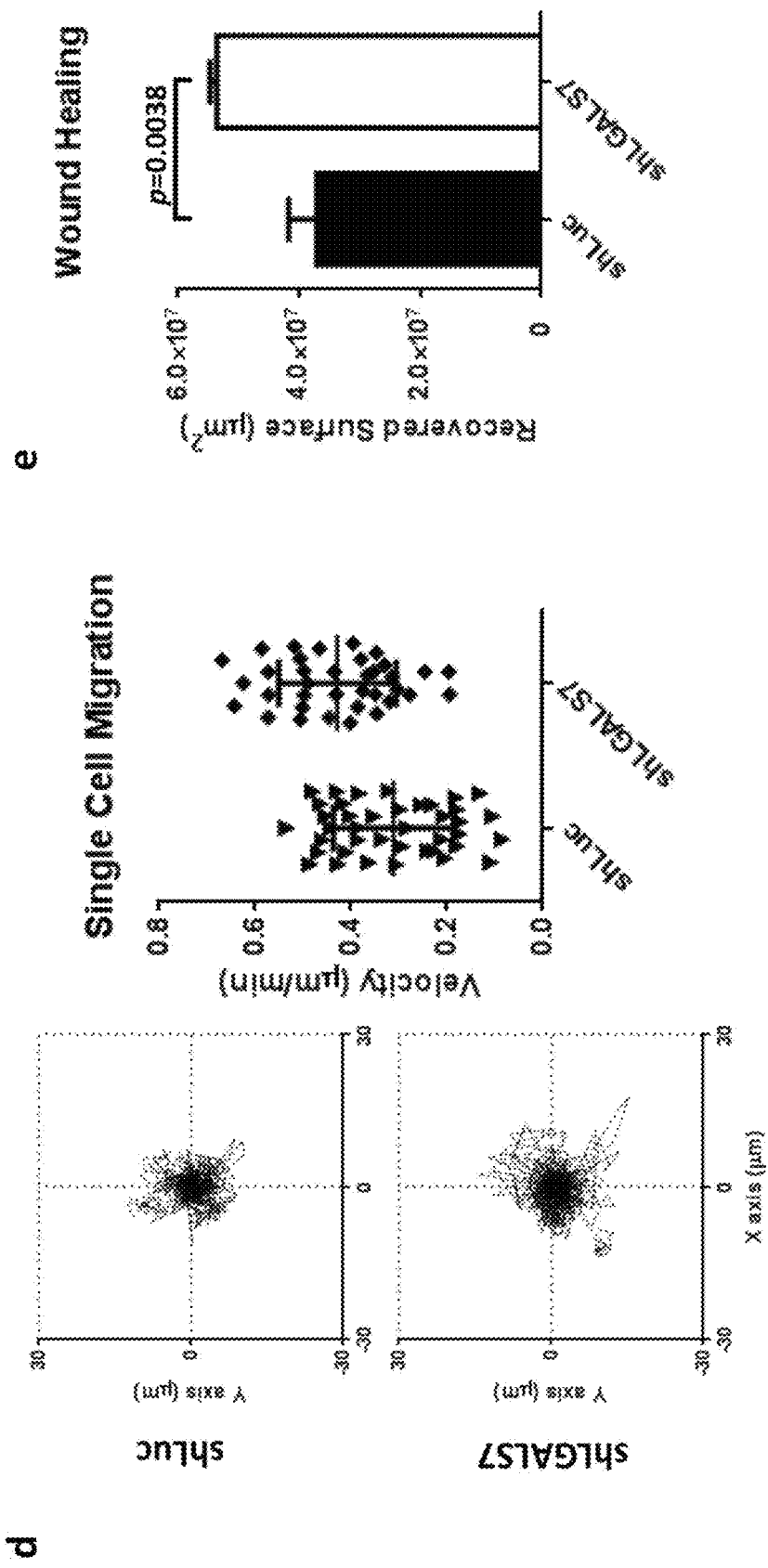

In terms of cell migration, PC9-IR cells were seeded in transwell culture plates for 16 hours. After incubation, the cells from the upper and bottom wells were collected respectively, and the mRNA of the cells were extracted and analyzed separately. Galectin-7 mRNA in cells from the bottom well was decreased as compared to those from the upper well (FIG. 9, Panel a).

The expression of E-cadherin (also known as cadherin 1, CDH1) and vimentin (VIM), two typical epithelial-mesenchymal transition (EMT) markers, were also examined by immunoblot analysis. As illustrated in FIG. 9, Panel b, CDH1 was downregulated, while VIM was upregulated in galectin-7 knockdown lung cancer cells (i.e., CL100 and PC9-IR cells). In contrast, in galectin-7-overexpressing PC9 cells, we found CDH1 was upregulated, and VIM was downregulated (FIG. 9, Panel b). These findings indicate galectin-7 may negatively regulate lung cancer cell migration, suggesting that galectin-7 may suppress tumor metastasis and recurrence.

The effects of galectin-7 on motility of lung cancer cells were also evaluated. According to FIG. 9, Panel c, knockdown of galectin-7 promoted cell migration in CL100 and PC9-IR cells, with induction of a 2.9-fold and 1.48-fold increase respectively, whereas overexpression of galectin-7 reduced cell invasion and migration in A549 and PC9 cells. In addition, in single cell migration assay and wound healing scratch assay, galectin-7 knockdown in PC9-IR cells exhibited an approximately 1.4-fold increase in velocity as compared to that in control cells (FIG. 9, Panels d and e).

Figure 10:
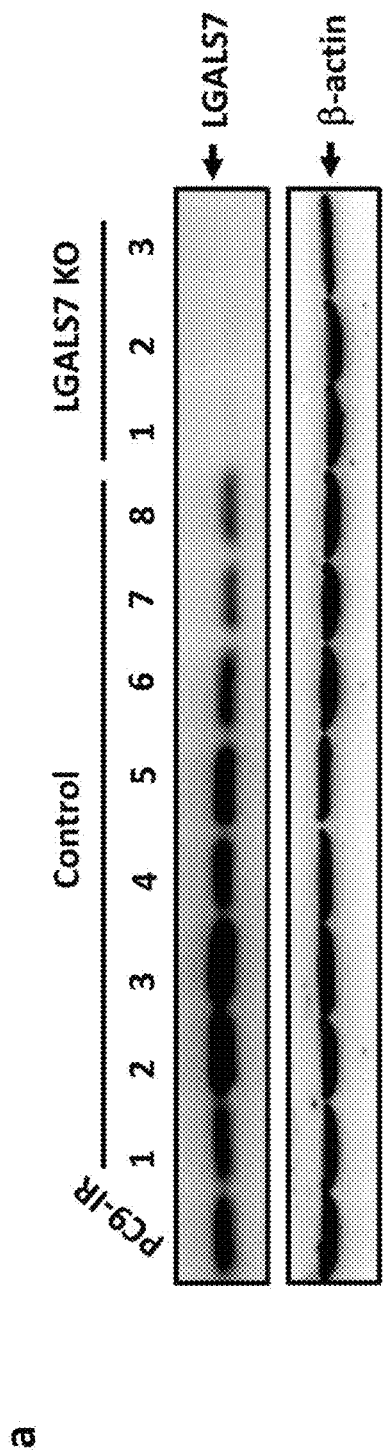
FIG. 10. Ablation of galectin-7 promoted cell migratory ability. Panel a, galectin-7 knockout cell clones of PC9-IR cells were generated using CRISPR. Migration ability was measured by transwell migration assay (n=6) (Panel b) and wound healing assay (n=4) (Panel c) in control and galectin-7 knockout (KO) cell clones. Panel d, each single galectin-7 KO cell clone was transfected with either control (p3×FLAG-CMV-14) or galectin-7-overexpressing (p3× FLAG-LGALS7) plasmids, and migration ability was measured by transwell migration assay (n=5).
Figure 10:
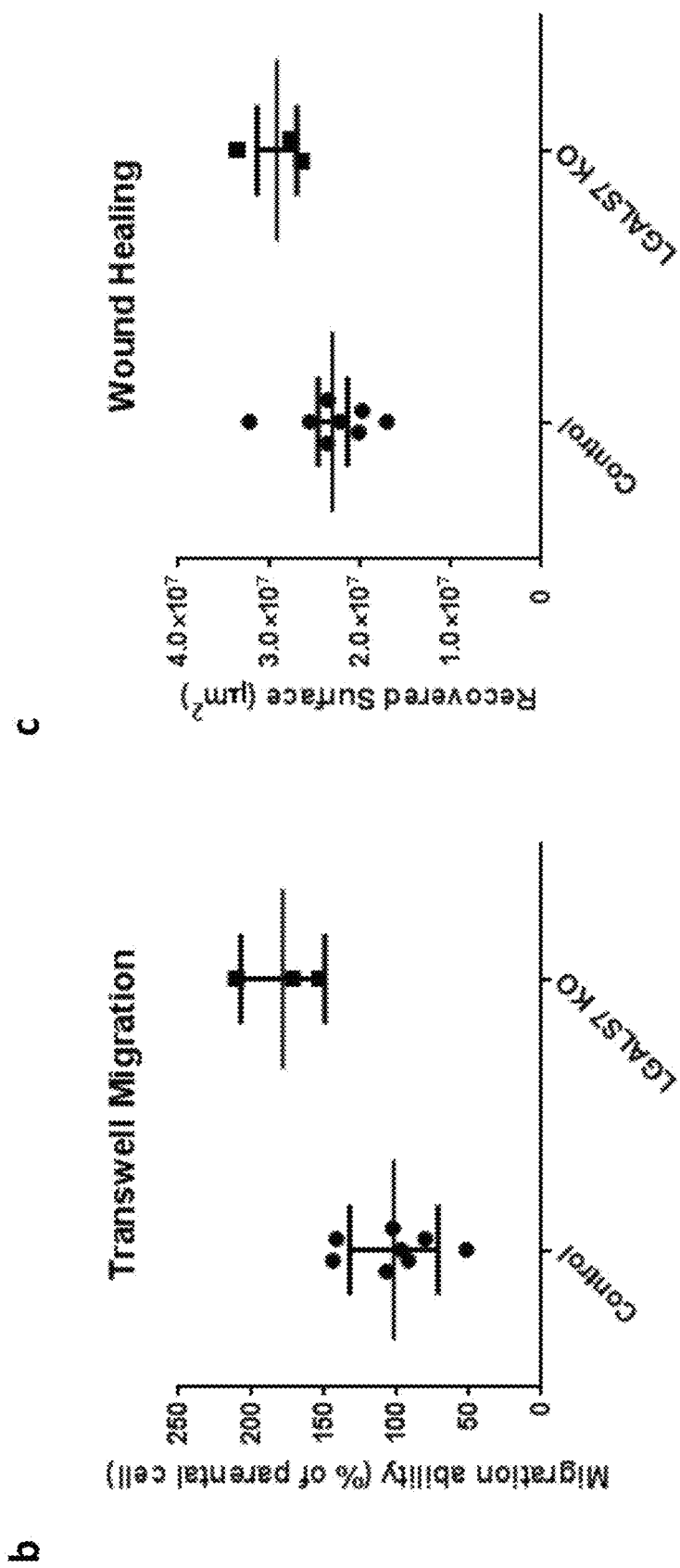
Figure 10:
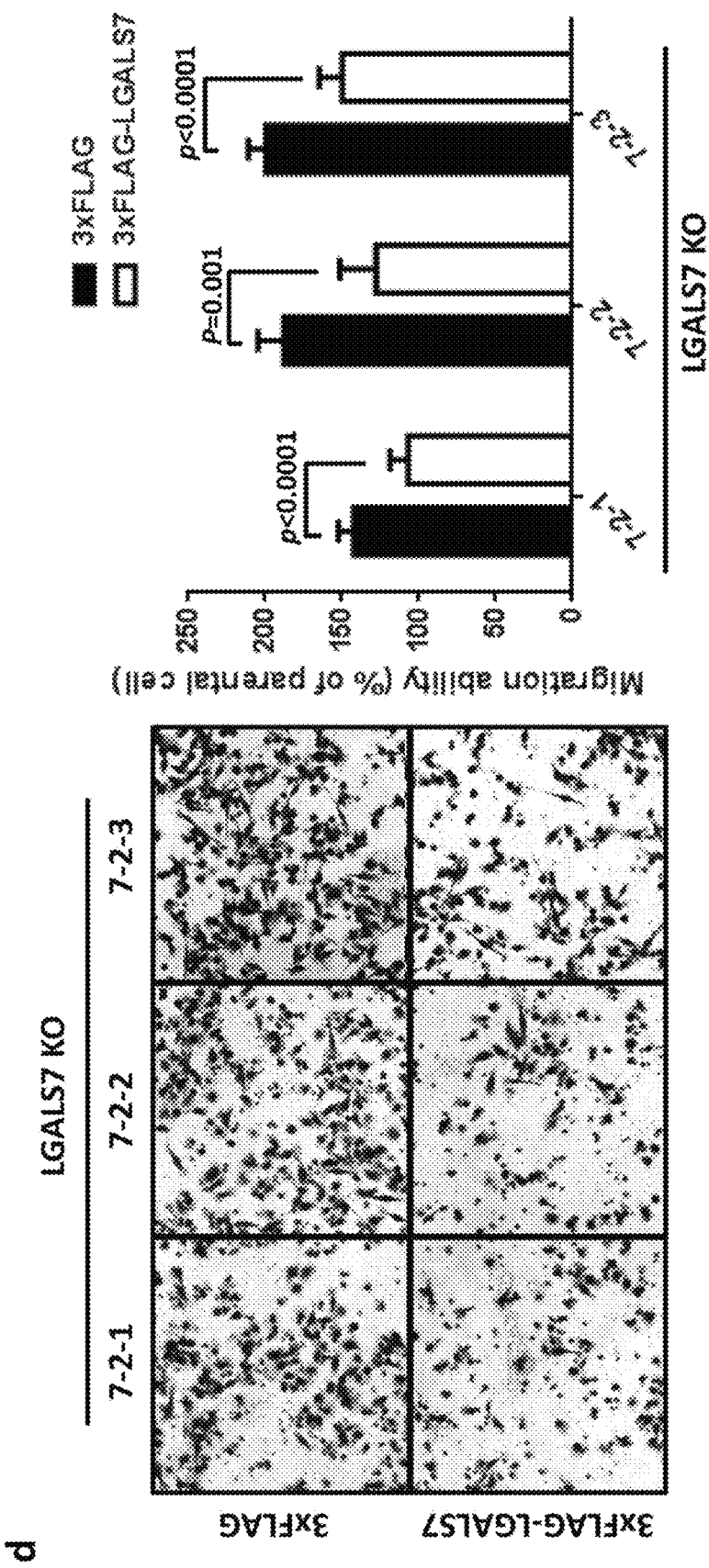

Galectin-7 knockout cell clones were generated using clustered regularly interspaced short palindromic repeats (CRISPR) in PC9-IR cells (FIG. 10, Panel a), and examined by transwell migration and wound healing scratch assays. As illustrated in FIG. 10, Panels b and c, ablation of galectin-7 expression promoted cell migratory ability. Furthermore, re-introduction of galectin-7 into galectin-7 knockout PC9-IR cells restored the suppression of galectin-7 on cell migration (FIG. 10, Panel d).

Figure 11:
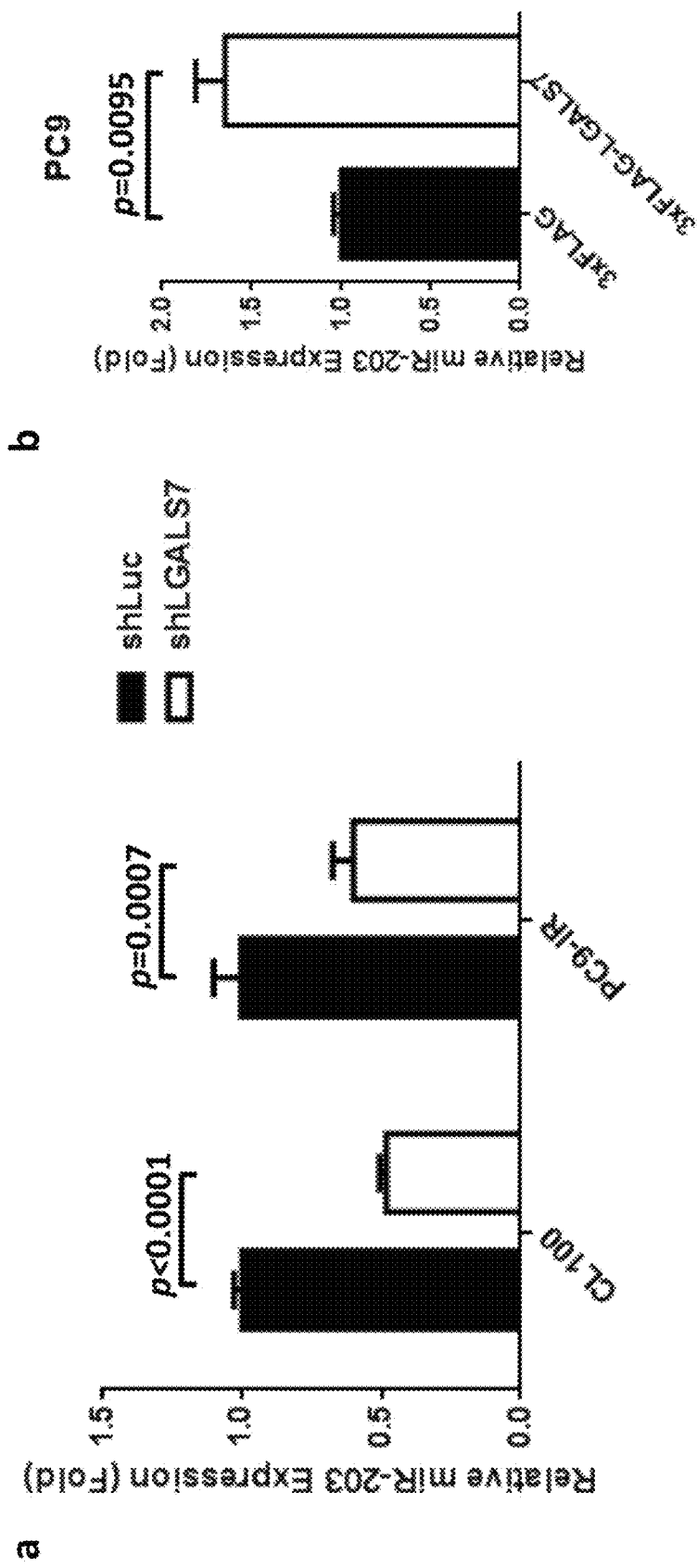
FIG. 11. miR-203 synergized in galectin-7-induced inhibition of cancer cell migration. Panels a and b, miR-203 expression was analyzed by qPCR in control, galectin-7 knockdown (n=4) (Panel a), and galectin-7-overexpressing (n=4) (Panel b) lung cancer cells. Panel c, control and galectin-7 knockdown PC9-IR cells were transfected with miR-203-overexpressing PMIRH203AA-1 (PMIR-203) vector and its scramble control vector, and migration ability was measured by transwell migration assay (n=4). Panel d, control and galectin-7-overexpressing PC9 cells were transfected with antisense miR-203 vector MZIP203-PA-1 (MZIP-203) or its scramble control vector, and migration ability was measured by transwell migration assay (n=4).
Figure 11:
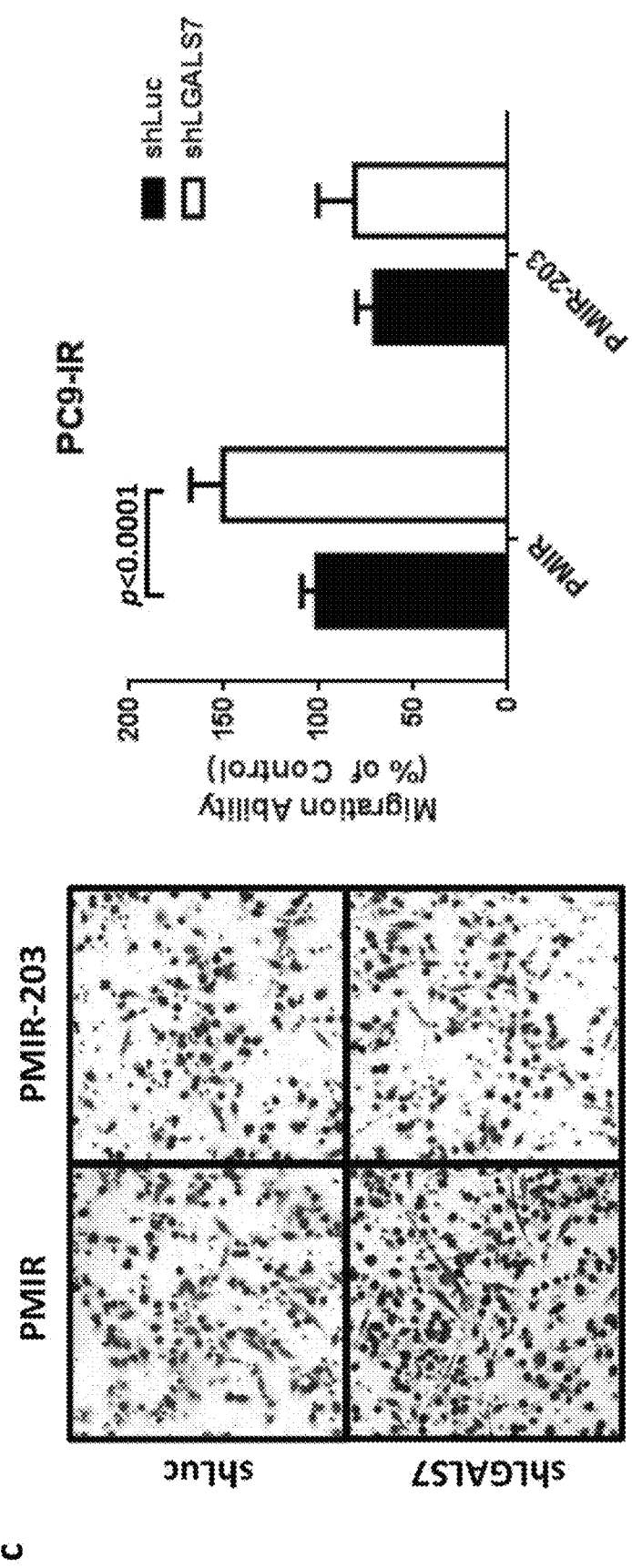
Figure 11:
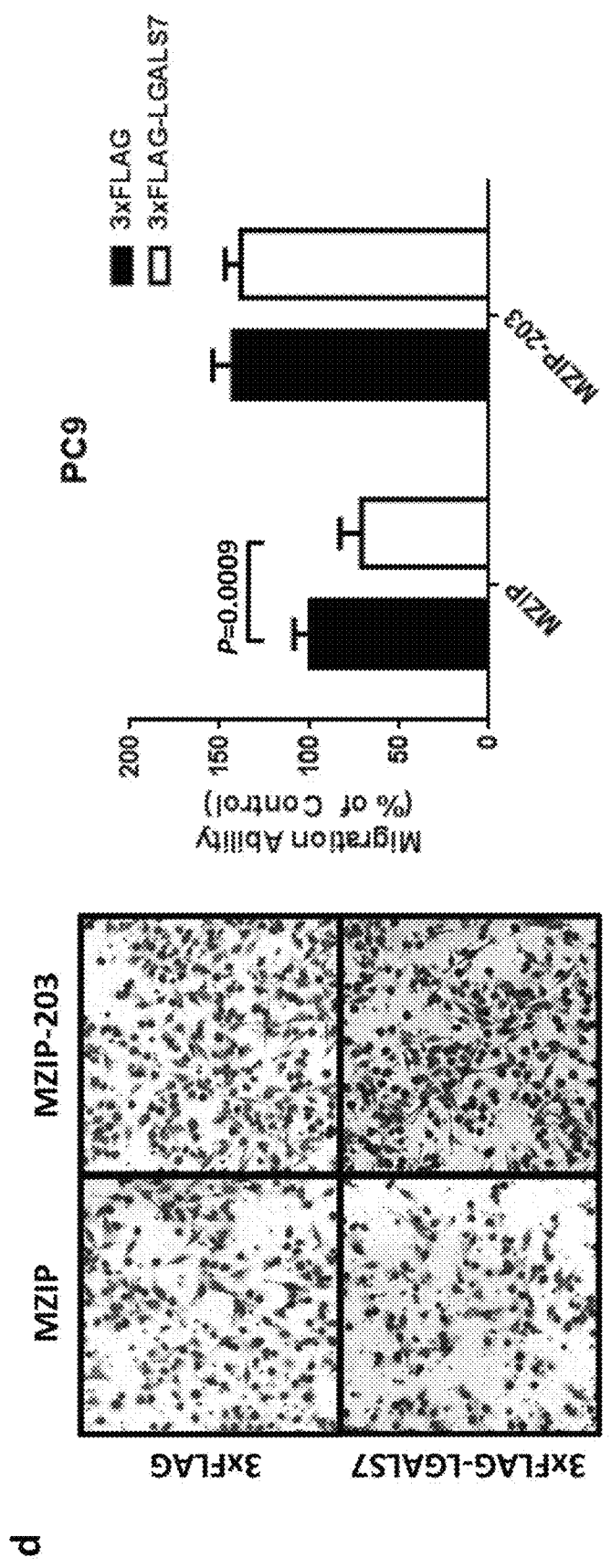

Example 10 Galectin-7 Regulates Cell Migration Through miR-203 in Lung Cancer Cells The relationship between miR-203 and galectin-7 in lung cancer cells was determined in the present example. As provided in FIG. 11, miR-203 was downregulated in galectin-7 knockdown CL100 and PC9-IR cells, and upregulated in galectin-7-overexpressing PC9 cells (FIG. 11, Panels a and b). In addition, overexpression of miR-203 in both control and galectin-7 knockdown PC9-IR cells resulted in the enhancement of cell migration, suggesting that the effect of galectin-7 knockdown was attenuated by miR-203 overexpression (FIG. 11, Panel c). Furthermore, knockdown of miR-203 restored the suppression of galectin-7 on cell migration (FIG. 11, Panel d), which confirmed that miR-203 may help in galectin-7-mediated inhibition of cancer cell migration.

Figure 12:
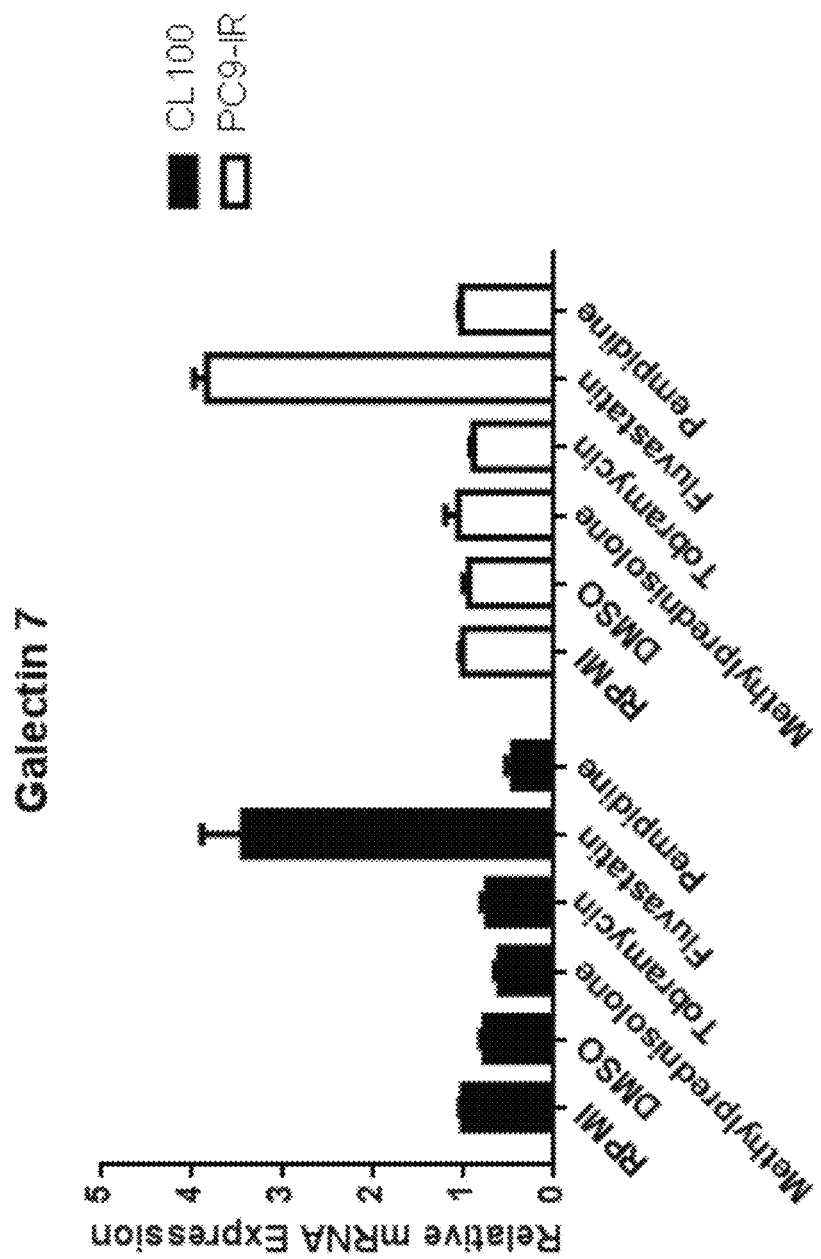
FIG. 12. Statins enhanced galectin-7 expression in lung cancer cells through mevalonate pathway. Panel a, CL100 and PC9-IR cells were treated with methylprednisolone (10.6 µM), tobramycin (8.6 µM), fluvastatin (9.2 µM), and pempidine (13 µM) for 24 hours; LGLAS7 mRNA levels were measured by qPCR (n=4). Panel b, lung cancer cells were tested with 10 µM atorvastatin (Atorva), cerivastatin (Ceriva), fluvastatin (Fluva), lovastatin (Lova), mevastatin (Meva), pitarvastatin (Pitarva), pravastatin (Prava), rosuvastatin (Rosuva), and simvastatin (Simva) for 24 hours, and measured for LGLAS7 protein levels by immunoblot assay. Panel c, 10 µM statins, including atorvastatin (Atorva), fluvastatin (Fluva), lovastatin (Lova), rosuvastatin (Rosuva), and simvastatin (Simva), were co-administrated with 200 µM mevalonate for 24 hours in PC9-IR cells; galectin-7 levels were measured by immunoblot assay. All immunoblot experiments were done at least in triplicate and the relative fold changes of galectin-7 were calculated and normalized to DMSO control.
Figure 12:
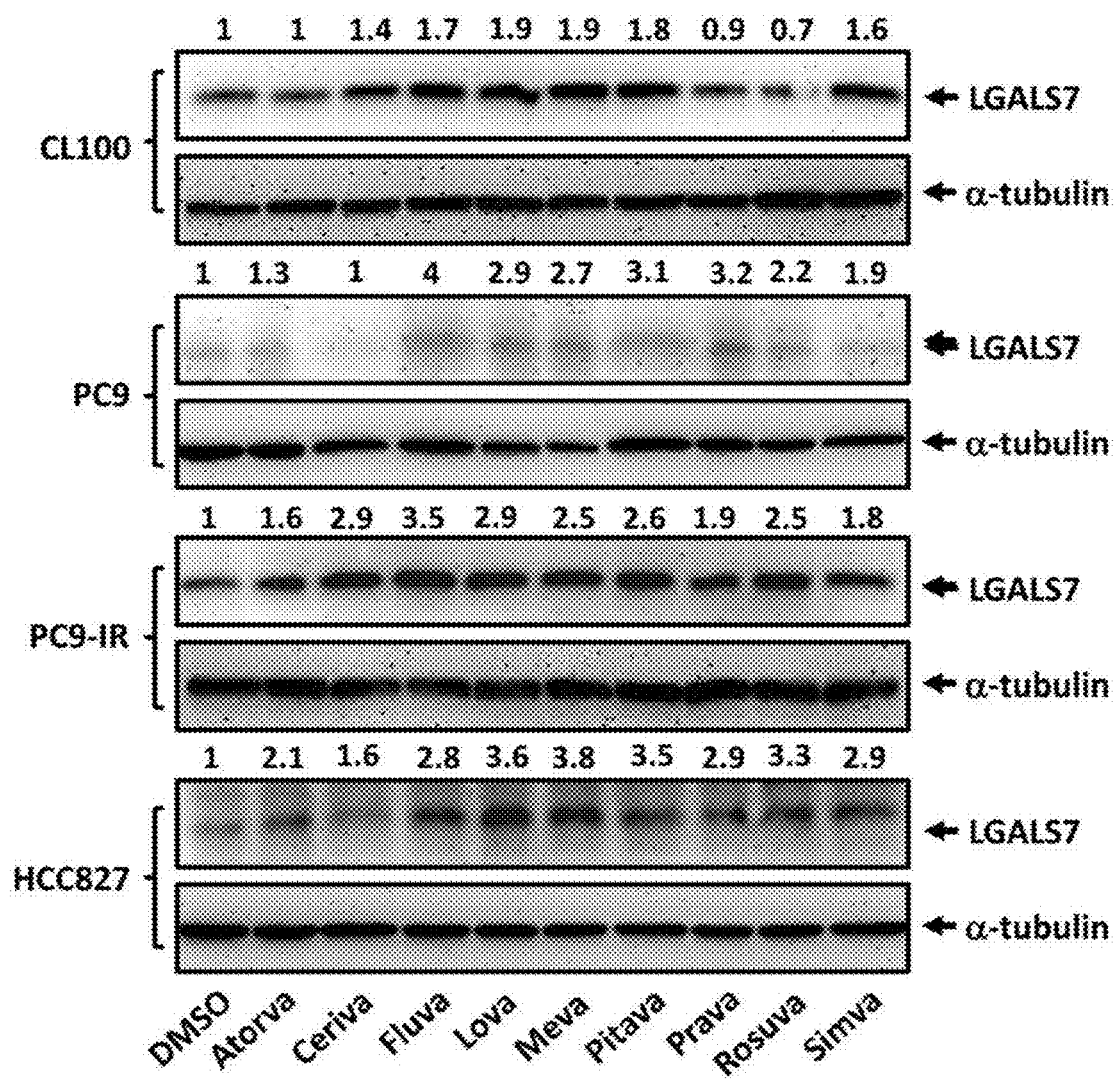
Figure 12:
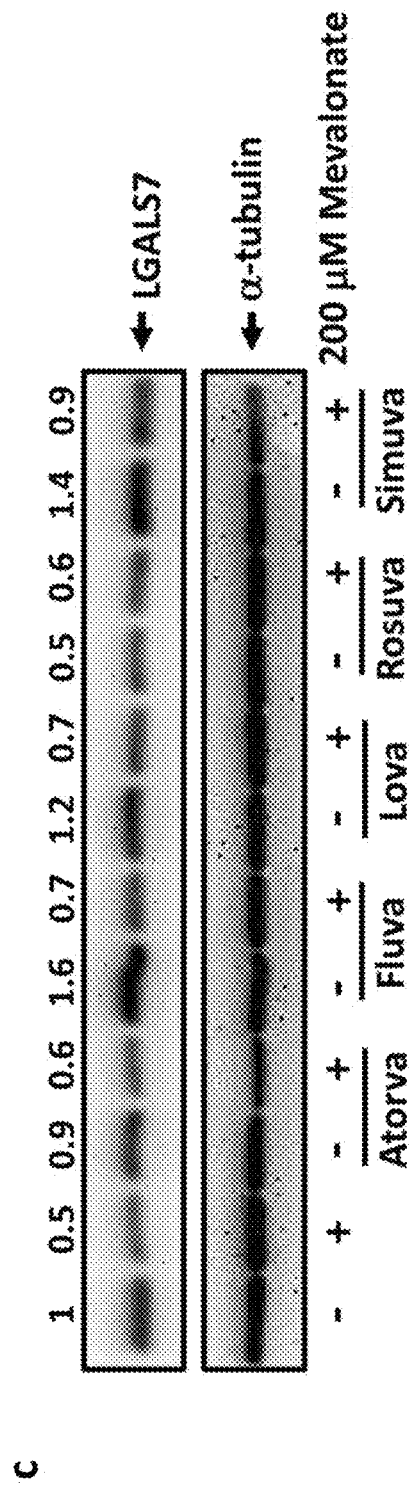

Example 11 Statins Enhance Galectin-7 Expression in Lung Cancer Cells Through Regulating the Mevalonate-Ras Pathway From Connectivity Map (cMAP, https://clue.io/cmap), four compounds: methylprednisolone, tobramycin, fluvastatin, and pempidine, were predicted to induce galectin-7 expression in several cancer cell lines. After examination, only fluvastatin induced galectin-7 expression in lung cancer cell lines (FIG. 12, Panel a). Next, lung cancer cells were treated with several statins in clinical use, including atorvastatin, cerivastatin, fluvastatin, lovastatin, mevastatin, pitavastatin, pravastatin, rosuvastatin, and simvastatin, and the majority of these statins enhanced galectin-7 expression (FIG. 12, Panel b). As an antagonist of HMG-CoA reductase inhibitors (i.e., statins), mevalonate, a main downstream product of the HMG-CoA reductase pathway, was used in the experiment. Administration of mevalonate reversed statin-induced upregulation of galectin-7 (FIG. 12, Panel c).

Figure 13:
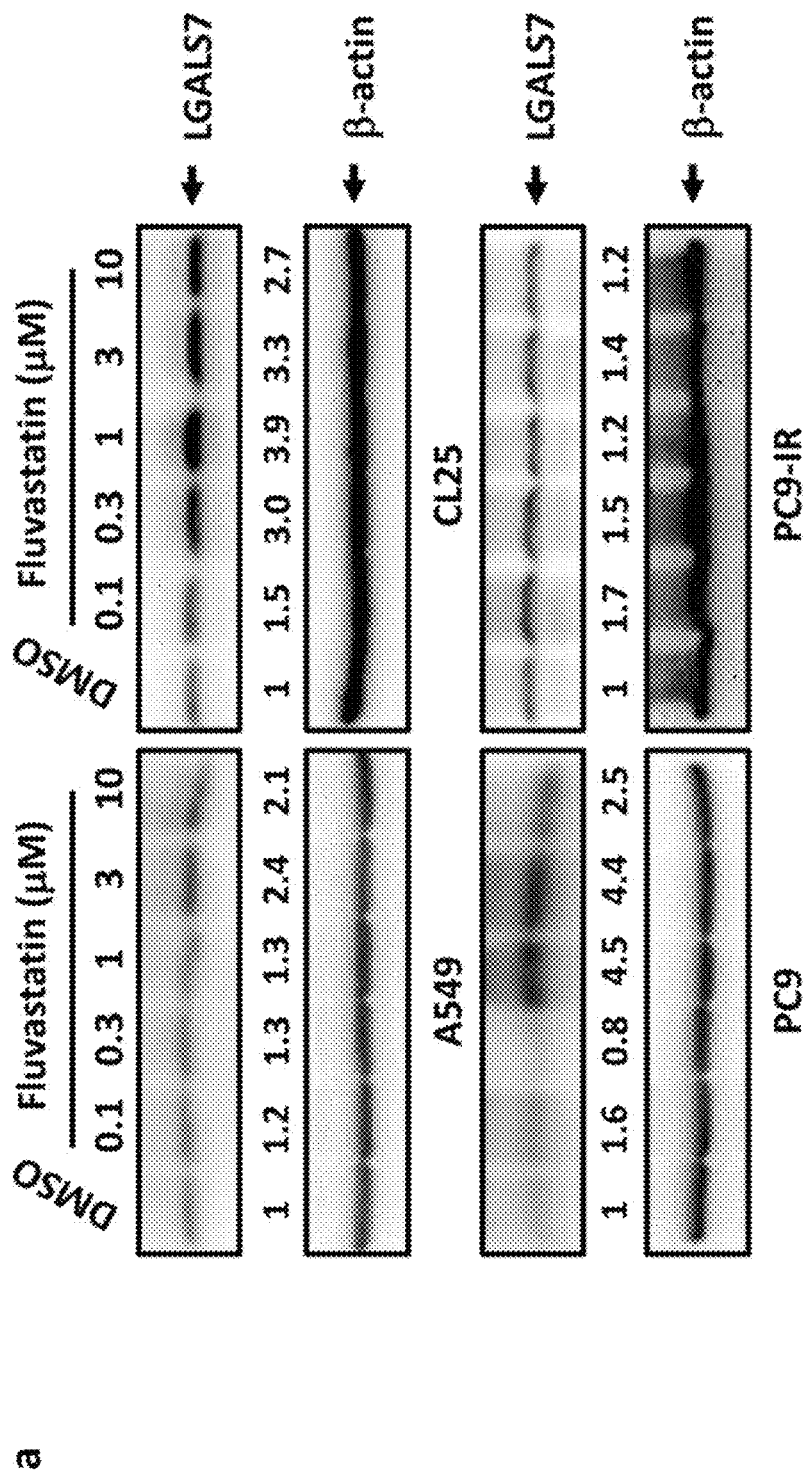
FIG. 13. Statins enhanced galectin-7 expression and inhibit cell migration in lung cancer cells through the mevalonate-Ras pathway. Panel a, lung cancer cells were treated with a series of fluvastatin ranging from 0.1 to 10 M for 24 hours; cell lysates were collected and analyzed by immunoblot. Panel b, NOD SCID mice were transplanted subcutaneously with A549, PC9, and PC9-IR cells, and treated with 30 mg/kg fluvastatin and lovastatin in saline solution. On day 21, tumor plaques were harvested and galectin-7 levels were measured by IHC staining and immunoblot assay. The relative fold changes of galectin-7 were calculated and normalized to the mean expression of saline-treated control group. Panel c, fluvastatin was co-administrated with 200 µM Mevalonate (Mev), 20 µM GGPP, and 20 µM FPP, respectively, to PC9-IR cells for 24 hours, and protein level of galectin-7 was determined by immunoblot assay. All immunoblot experiments were done at least in triplicate and the relative fold changes of galectin-7 were calculated and normalized to the control.
Figure 13:
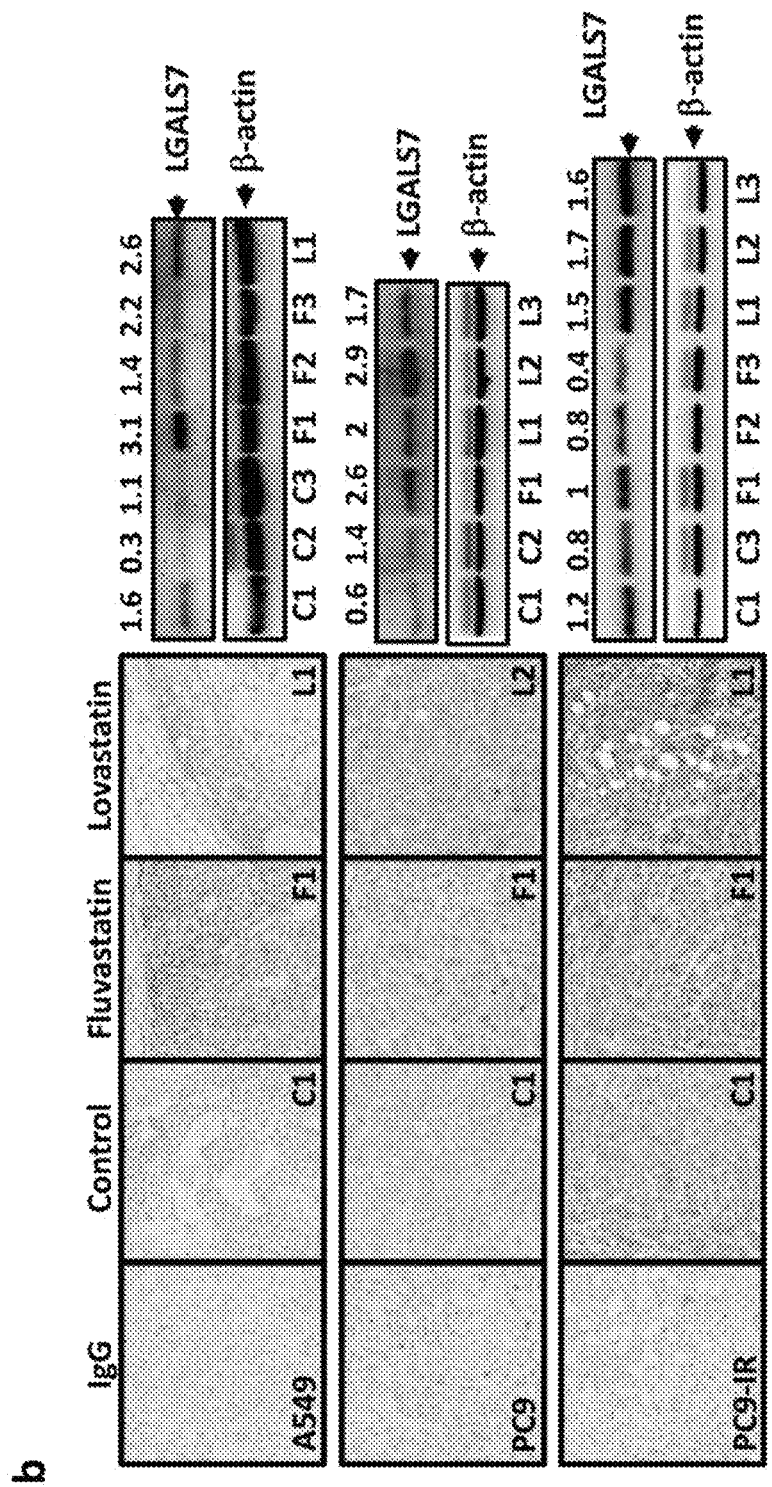
Figure 13:
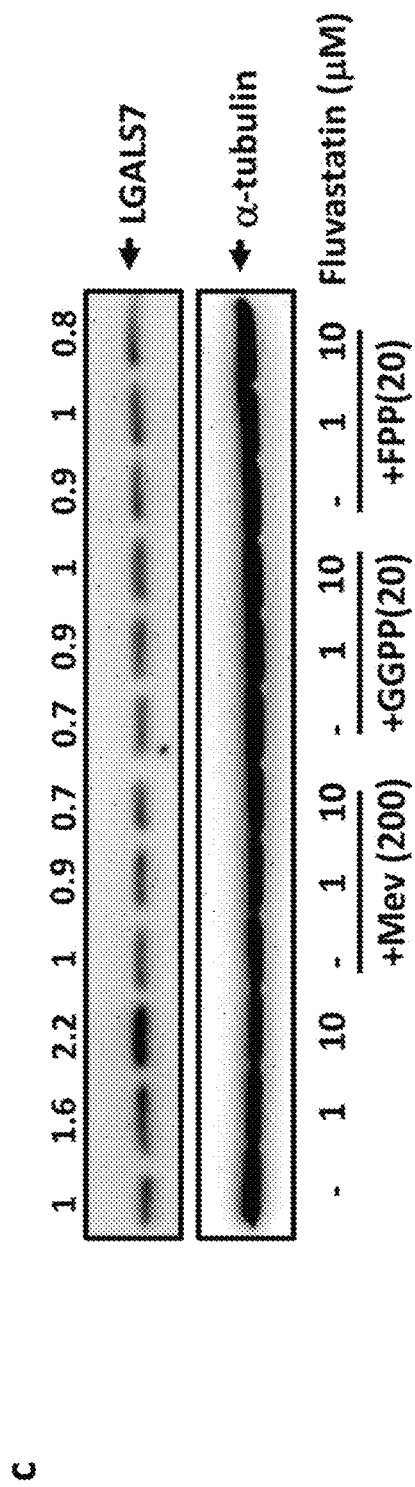

By immunoblot analysis, galectin-7 protein levels were upregulated in several lung cancer cell lines by fluvastatin in a dose-dependent manner (FIG. 13, Panel a). The effects of fluvastatin on lung cancer cells in vivo were also assessed. NOD SCID mice were subcutaneously transplanted with A549, PC9, and PC9-IR cells and treated with fluvastatin and lovastatin daily by oral gavage. On day 21, tumor plaques were harvested, and galectin-7 levels were measured by IHC staining and immunoblot. Both fluvastatin and lovastatin increased galectin-7 expression in transplanted tumors as compared to the saline-treated control group (FIG. 13, Panel b). Similarly, administration of mevalonate reversed statin-induced upregulation of galectin-7 (FIG. 13, Panel c). In addition, co-administration of GGPP and FPP, which are two other downstream products of the HMG-CoA reductase pathway, blocked fluvastatin-induced galectin-7 upregulation (FIG. 13, Panel c). These results suggest that statins induce galectin-7 upregulation through the mevalonate pathway.

Figure 14:
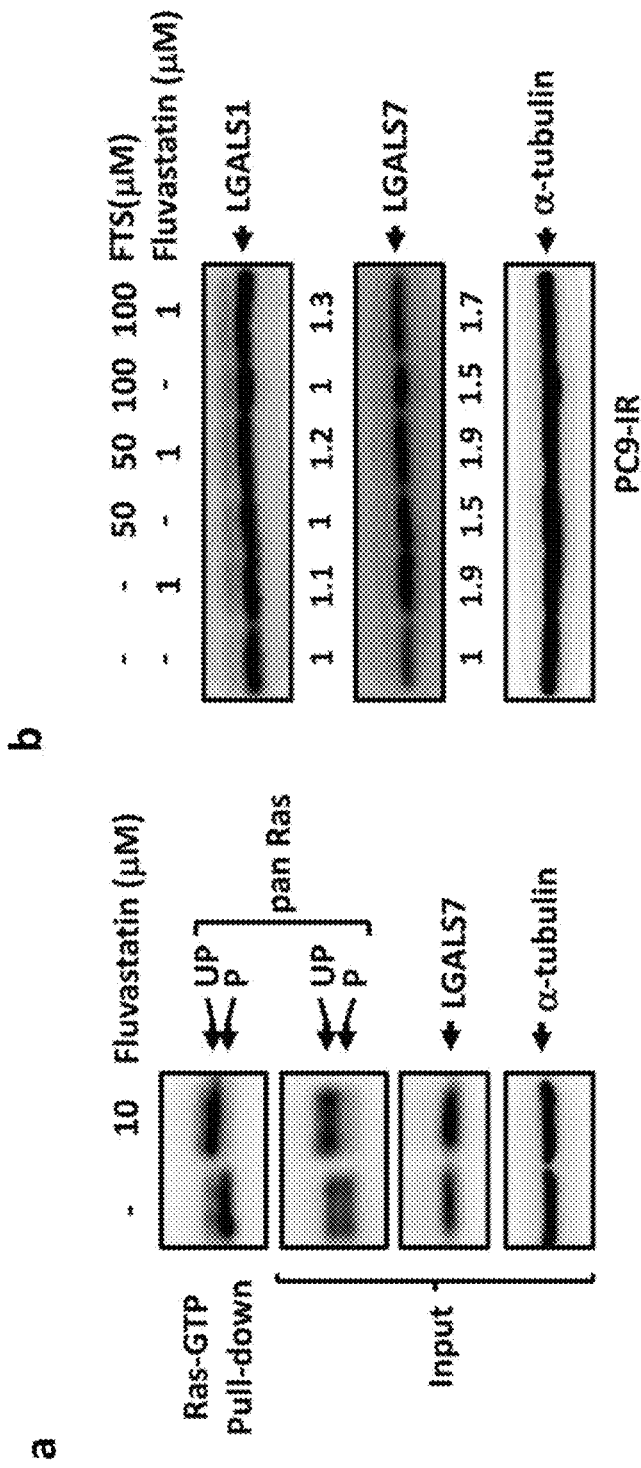
FIG. 14. Ras was involved in fluvastatin-induced galectin-7 upregulation. Panel a, PC9-IR cells were treated with 10 µM fluvastatin for 24 hours. Ras-GTP was pulled down using Raf-RBD beads. Panel b, 1 µM fluvastatin was co-administrated with 50 and 100 M FTS for 24 hours. Protein expression of galectin-1 (LGALS1), galectin-7, and pan Ras were measured by immunoblot assay. Prenylated Ras (P) corresponded to the lower band whereas the upper band corresponded to the unprenylated (UP) moiety. All immunoblot experiments were done at least in triplicate and the relative fold changes of galectin-7 were calculated and normalized to the control.

GGPP and FPP are also two important factors for Ras prenylation and critical for membrane-translocation and activation of Ras. In the present study, a pull-down assay of Ras-GTP using Raf-RBD beads was performed and followed by immunoblot analysis to evaluate the role of Ras in the context of the fluvastatin-galectin-7 axis. As illustrated in FIG. 14, Panel a, fluvastatin treatment inhibited Ras prenylation and subsequent Ras-GTP formation. According to literatures, Ras inhibition may boost galectin-7 expression, and therefore the effects of Ras inhibition, by using a Ras inhibitor (e.g., farnesyl thiosalicylic acid (FTS)), on fluvastatin-induced galectin-7 expression was determined. Both fluvastatin and FTS treatment increased galectin-7 expression in PC9-IR cells, but co-administration of these two compounds only slightly increased galectin-7 expression which is comparable to that induced by fluvastatin alone (FIG. 14, Panel b).

Figure 15:
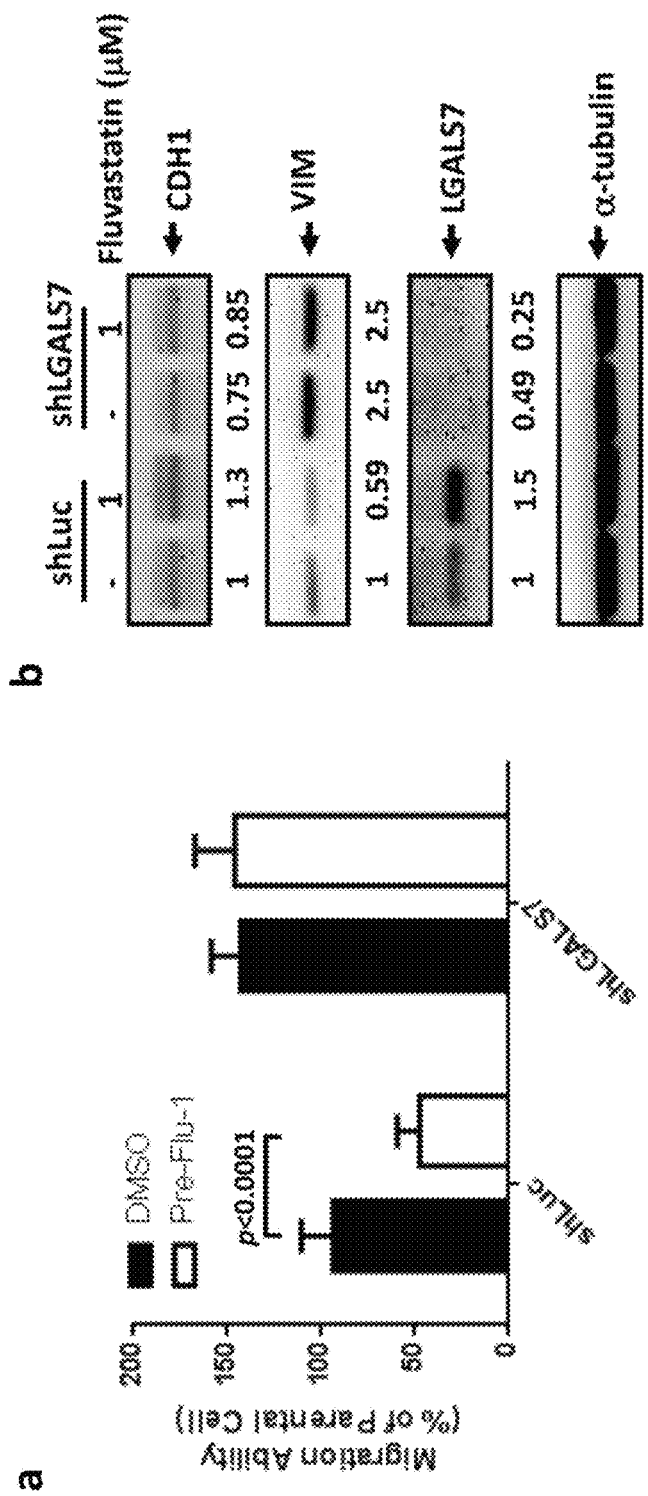
FIG. 15. Galectin-7 influenced fluvastatin-induced inhibition of cell migration. Panel a, control and galectin-7 knockdown PC9-IR cells were pretreated with 1 µM fluvastatin for 24 hours, and a transwell migration assay were performed (n=3). Panel b, protein expression of CDH1, VIM, and galectin-7 were measured by immunoblot assay. All immunoblot experiments were done at least in triplicate and the relative fold changes of CDH1, VIM, and galectin-7 were calculated and normalized to the control.

Example 12 Galectin-7 is a Key Determinant in Fluvastatin-Induced Inhibition of Cell Migration To exploit the role of galectin-7 in fluvastatin-induced inhibition of cell migration in lung cancer cells, a transwell migration assay was employed using PC9-IR cells. Control and galectin-7 knockdown PC9-IR cells were pretreated with 1 μM fluvastatin for 24 hours before performing a transwell migration assay. As provided in FIG. 15, Panel a, knockdown of galectin-7 completely restored fluvastatin-induced inhibition of cell migration. In addition, fluvastatin-induced changes in EMT markers, such as CDH1 not being upregulated, and VIM not being downregulated, in galectin-7 knockdown PC9-IR cells (FIG. 15, Panel b). The results suggest that galectin-7 helps in fluvastatin-induced inhibition of cell migration.

Example 13 Galectin-7 Levels in Squamous Cancer Cells

The levels of galectin-7 in other cancers such as esophageal cancer, oral cancer, or skin cancer were provided in the present Example. Relative galectins mRNA expression among these cancers was approached by a meta-analysis method, and all of the galectin-7 was downregulated in these cancers. Data were summarized in Table 4-6.

TABLE 4

Relative galectins mRNA expression fold change in skin squamous cancer cell lines (SSCs) as compared to keratinocytes HaCaT cell (Data meta-analysis of GSE4975)

| ID_REF | HaCaT | SSC-12 | SSC-6 | Gene Symbol |
|---|---|---|---|---|
| 208450_at | 1.00 | 5.15 | 2.53 | Galectin-2 |
| 220440_at | 1.00 | 2.72 | 1.12 | Galectin-13 |
| 220158_at | 1.00 | 1.36 | 1.27 | Galectin-14 |
| 203236_s_at | 1.00 | −1.10 | 1.40 | Galectin-9 |
| 204272_at | 1.00 | −1.15 | 1.37 | Galectin-4 |
| 210731_s_at | 1.00 | −1.34 | −2.01 | Galectin-8 |
| 201105_at | 1.00 | −1.47 | 2.62 | Galectin-1 |
| 208949_s_at | 1.00 | −4.78 | −1.01 | Galectin-3 |
| 206400_at | 1.00 | −9.40 | −11.81 | Galectin-7/Galectin-7B |

TABLE 5

Relative galectins mRNA expression fold change in 15 paired esophageal squamous cell cancer (ESCC) samples and matched nonmalignant mucosa were analyzed (Data meta-analysis of GSE75241)

| Transcripts Cluster Id | [Normal] | [Tumor] | Gene Symbol |
|---|---|---|---|
| 2386867 | 1 | 1.24 | Galectin-8\|HEATR1 |
| 3333877 | 1 | −1.19 | Galectin-12 |
| 3536706 | 1 | −2.04 | Galectin-galectin-3 |
| 3715274 | 1 | 1.01 | Galectin-9 |
| 3832736 | 1 | −2.17 | Galectin-7/Galectin-7B |
| 3833238 | 1 | −1.13 | Galectin-14 |
| 3861557 | 1 | −1.20 | Galectin-4 |
| 3944882 | 1 | 3.77 | Galectin-1 |
| 3960174 | 1 | −1.11 | Galectin-2 |

TABLE 6

Relative galectins mRNA expression fold change in eight oral squamous cell carcinoma (OSCC) cell lines (H-Series and M9) compared with a primary culture of normal oral keratinocytes (NK) (Data meta-analysis of GSE31853)

| Probe Set ID | [Normal] | [OSCC] | Gene Symbol |
|---|---|---|---|
| 201105_at | 1.00 | −2.20 | Galectin-1 |
| 203236_s_at | 1.00 | −1.12 | Galectin-9 |
| 204272_at | 1.00 | 1.00 | Galectin-4 |
| 206400_at | 1.00 | −50.87 | Galectin-7/Galectin-7B |
| 208450_at | 1.00 | 1.00 | Galectin-2 |
| 208933_s_at | 1.00 | 1.83 | Galectin-8 |
| 208949_s_at | 1.00 | −2.13 | Galectin-3 |
| 210731_s_at | 1.00 | 1.00 | Galectin-8 |
| 210732_s_at | 1.00 | 1.27 | Galectin-8 |
| 219998_at | 1.00 | −1.51 | Galectin-L |
| 220158_at | 1.00 | −1.01 | Galectin-14 |
| 220440_at | 1.00 | 1.02 | Galectin-13 |

Figure 16:
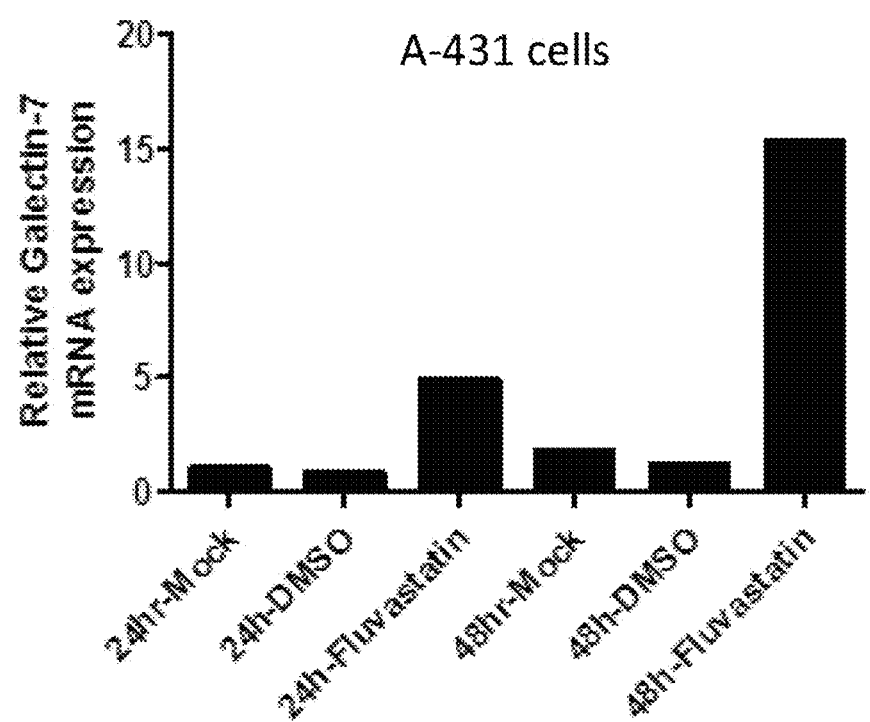
FIG. 16. Fluvastatin increases galectin-7 levels in skin cancer A-431 cells. Real-time PCR analysis of mRNA expression of galectin-7 in A-431 cells treated with fluvastatin (9.2 µM), vehicle control (DMSO), or non-treatment control (Mock) for 24 hours or 48 hours as indicated. The relative fold changes were calculated by the ΔΔCt method; data from all the samples were normalized to the mock sample, and GAPDH served as an endogenous control.

To elucidate the effect of fluvastatin on upregulation of galectin-7 in these cancer cells, skin cancer A-431 cells were used as an example. A-431 cells were treated with fluvastatin for 24 hours and 48 hours, and galectin-7 levels were assayed by qPCR. As exhibited in FIG. 16, fluvastatin increased galectin-7 expression as compared to DMSO and Mock control.

In summary, the present disclosure demonstrates the effects of galectin-7 on psoriasis as well as cancers, and that the agent (e.g., the statin drug) useful in enhancing the expression of galectin-7 provides a potential means to treat both psoriasis and cancers.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. An antibody or a fragment thereof that binds to galectin-7, comprising:
   a heavy chain variable region comprising a first heavy chain complementarity determining region (CDR-H1), a second heavy chain CDR (CDR-H2), and a third heavy chain CDR (CDR-H3), wherein the CDR-H1, the CDR-H2, and the CDR-H3 respectively comprise the amino acid sequences of SEQ ID NOs: 1, 2 and 3; and
   a light chain variable region comprising a first light chain CDR (CDR-L1), a second light chain CDR (CDR-L2), and a third light chain CDR (CDR-L3), wherein the CDR-L1, the CDR-L2, and the CDR-L3 respectively comprise the amino acid sequences of SEQ ID NOs: 4, 5 and 6.

2. The antibody or the fragment thereof of claim 1, wherein the heavy chain variable region is at least 85% identical to SEQ ID NO: 7, and the light chain variable region is at least 85% identical to SEQ ID NO: 8.

3. The antibody or the fragment thereof of claim 2, wherein the heavy chain variable region has the amino acid sequence of SEQ ID NO: 7, and the light chain variable region has the amino acid sequence of SEQ ID NO: 8.

4. A method of selecting a drug candidate suitable for treating psoriasis or cancer in a subject, comprising,
   (a) incubating keratinocytes with one or more candidate drugs;
   (b) determining the expression level of galectin-7 in the keratinocytes of step (a) by use the antibody or the fragment thereof of claim 1; and
   (c) selecting the drug candidate from the one or more candidate drugs based on the expression level determined in step (b), wherein the drug candidate increases the expression level of galectin-7.

5. The method of claim 4, wherein the selected drug candidate in the step (c) is a statin.

6. The method of claim 5, wherein the subject has the psoriasis, and the statin is fluvastatin, atorvastatin, cerivastatin, pitavastatin, or simvastatin.

7. The method of claim 5, wherein the subject has the cancer, and the statin is fluvastatin, atorvastatin, cerivastatin, pitavastatin, simvastatin, lovastatin, mevastatin, pravastatin, or rosuvastatin.

8. The method of claim 4, wherein the heavy chain variable region of the antibody or the fragment thereof is at least 85% identical to SEQ ID NO: 7, and the light chain variable region of the antibody or the fragment thereof is at least 85% identical to SEQ ID NO: 8.

9. The method of claim 8, wherein the heavy chain variable region of the antibody or the fragment thereof has the amino acid sequence of SEQ ID NO: 7, and the light chain variable region of the antibody or the fragment thereof has the amino acid sequence of SEQ ID NO: 8.

10. A method of treating psoriasis or cancer in a subject, comprising:
    (1) selecting a drug candidate suitable for treating the psoriasis or the cancer by,
       (1a) incubating keratinocytes with one or more candidate drugs;
       (1b) determining the expression level of galectin-7 in the keratinocytes of step (1a) by use the antibody or the fragment thereof of claim 1; and
       (1c) selecting the drug candidate from the one or more candidate drugs based on the expression level determined in step (1b), wherein the drug candidate increases the expression level of galectin-7; and
    (2) treating the subject by administering to the subject an effective amount of a pharmaceutical composition, which comprises the selected drug candidate in the step (1c) and a pharmaceutically acceptable carrier.

11. The method of claim 10, wherein the selected drug candidate in the step (1c) is a statin.

12. The method of claim 11, wherein the subject has the psoriasis, and the statin is fluvastatin, atorvastatin, cerivastatin, pitavastatin, or simvastatin.

13. The method of claim 11, wherein the subject has the cancer, and the statin is fluvastatin, atorvastatin, cerivastatin, pitavastatin, simvastatin, lovastatin, mevastatin, pravastatin, or rosuvastatin.

14. The method of claim 10, wherein the subject has the psoriasis, and the pharmaceutical composition further comprises an TNF-α inhibitor, which is an anti-TNF-α antibody or a TNF-α antagonist.

15. The method of claim 10, wherein the subject has the cancer, and the pharmaceutical composition further comprises a renin-angiotensin system (Ras) inhibitor, which is farnesyl thiosalicylic acid (FTS), ARS-853, or ARS-162.

16. The method of claim 10, wherein the subject is a human.

17. The method of claim 10, wherein the cancer is bladder cancer, biliary cancer, bone cancer, brain tumor, breast cancer, cervical cancer, colorectal cancer, dysgerminoma, esophageal cancer, epidermal cancer, gastric cancer, gastrointestinal stromal tumor (GIST), glioma, non-Hodgkin's lymphoma, head and neck cancer, intestinal cancer, Kaposi's sarcoma, liver cancer, lung cancer, lymphoma, lymphoid leukemia, melanoma, myeloid leukemia, nasopharyngeal cancer, oral cancer, ovary cancer, pancreatic cancer, prostate cancer, retinoblastoma, renal cell carcinoma, sarcoma, seminoma, skin cancer, spleen cancer, squamous cell carcinoma, teratoma, teratocarcinoma, thyroid cancer, or thyroid follicular cancer.

18. The method of claim 17, wherein the cancer is esophageal cancer, lung cancer, oral cancer, or skin cancer.

* * * * *

SEQUENCE LISTING

<160> NUMBER OF SEQ ID NOS: 26

<210> SEQ ID NO 1
<211> LENGTH: 5
<212> TYPE: PRT

```
<213> ORGANISM: Artificial Sequence
<220> FEATURE:
<223> OTHER INFORMATION: Synthetic

<400> SEQUENCE: 1

Asn Tyr Gly Met Asn
1               5

<210> SEQ ID NO 2
<211> LENGTH: 17
<212> TYPE: PRT
<213> ORGANISM: Artificial Sequence
<220> FEATURE:
<223> OTHER INFORMATION: Synthetic

<400> SEQUENCE: 2

Trp Ile Asn Thr Tyr Thr Gly Glu Pro Thr Tyr Ala Asp Asp Phe Lys
1               5                   10                  15

Gly

<210> SEQ ID NO 3
<211> LENGTH: 10
<212> TYPE: PRT
<213> ORGANISM: Artificial Sequence
<220> FEATURE:
<223> OTHER INFORMATION: Synthetic

<400> SEQUENCE: 3

Arg Arg Arg Pro Tyr Tyr Ala Met Asp Tyr
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Synthetic

<400> SEQUENCE: 4

Lys Ala Ser Glu Asn Val Gly Ile Tyr Val Ser
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Synthetic

<400> SEQUENCE: 5

Gly Ala Ser Asn Arg Tyr Thr
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic

<400> SEQUENCE: 6

Gly Gln Ser Tyr Ile Tyr Pro Phe Thr
1               5

<210> SEQ ID NO 7
<211> LENGTH: 138
```

<212> TYPE: PRT
<213> ORGANISM: Artificial Sequence
<220> FEATURE:
<223> OTHER INFORMATION: Synthetic

<400> SEQUENCE: 7

Met Asp Trp Leu Trp Asn Leu Leu Phe Leu Met Ala Ala Ala Gln Ser
1               5                   10                  15

Ala Gln Ala Gln Ile Gln Leu Val Gln Ser Gly Pro Glu Leu Lys Lys
            20                  25                  30

Pro Gly Glu Thr Val Lys Ile Ser Cys Lys Ala Ser Gly Tyr Thr Phe
        35                  40                  45

Thr Asn Tyr Gly Met Asn Trp Val Lys Gln Ala Pro Gly Lys Gly Leu
    50                  55                  60

Lys Trp Met Gly Trp Ile Asn Thr Tyr Thr Gly Glu Pro Thr Tyr Ala
65                  70                  75                  80

Asp Asp Phe Lys Gly Arg Phe Ala Phe Ser Leu Glu Thr Ser Ala Ser
                85                  90                  95

Thr Ala Tyr Leu Gln Ile Asn Asn Leu Lys Asn Glu Asp Met Ala Thr
            100                 105                 110

Tyr Phe Cys Ala Leu Arg Arg Arg Pro Tyr Tyr Ala Met Asp Tyr Trp
        115                 120                 125

Gly Gln Gly Thr Ser Val Thr Val Ser Ser
    130                 135

<210> SEQ ID NO 8
<211> LENGTH: 127
<212> TYPE: PRT
<213> ORGANISM: Artificial Sequence
<220> FEATURE:
<223> OTHER INFORMATION: Synthetic

<400> SEQUENCE: 8

Met Glu Ser Gln Thr Leu Val Phe Ile Ser Ile Leu Leu Trp Leu Tyr
1               5                   10                  15

Gly Ala Asp Gly Asn Ile Val Met Thr Gln Ser Pro Lys Ser Met Ser
            20                  25                  30

Met Ser Val Gly Glu Arg Val Thr Leu Ser Cys Lys Ala Ser Glu Asn
        35                  40                  45

Val Gly Ile Tyr Val Ser Trp Tyr Gln Gln Lys Pro Glu Gln Ser Pro
    50                  55                  60

Lys Leu Leu Ile Tyr Gly Ala Ser Asn Arg Tyr Thr Gly Val Pro Asp
65                  70                  75                  80

Arg Phe Thr Gly Ser Gly Ser Ala Thr Asp Phe Thr Leu Thr Ile Ser
                85                  90                  95

Ser Val Gln Ala Glu Asp Leu Ala Asp Tyr His Cys Gly Gln Ser Tyr
            100                 105                 110

Ile Tyr Pro Phe Thr Phe Gly Ser Gly Thr Lys Leu Glu Ile Lys
        115                 120                 125

<210> SEQ ID NO 9
<211> LENGTH: 15
<212> TYPE: DNA
<213> ORGANISM: Artificial Sequence
<220> FEATURE:
<223> OTHER INFORMATION: Synthetic

<400> SEQUENCE: 9
aactatggaa tgaac                                                15

<210> SEQ ID NO 10
<211> LENGTH: 51
<212> TYPE: DNA
<213> ORGANISM: Artificial Sequence
<220> FEATURE:
<223> OTHER INFORMATION: Synthetic

<400> SEQUENCE: 10
tggataaaca cctacactgg agagccaaca tatgctgatg acttcaaggg a         51

<210> SEQ ID NO 11
<211> LENGTH: 30
<212> TYPE: DNA
<213> ORGANISM: Artificial Sequence
<220> FEATURE:
<223> OTHER INFORMATION: Synthetic

<400> SEQUENCE: 11
cgacgacgcc cttactatgc tatggactac                                  30

<210> SEQ ID NO 12
<211> LENGTH: 33
<212> TYPE: DNA
<213> ORGANISM: Artificial Sequence
<220> FEATURE:
<223> OTHER INFORMATION: Synthetic

<400> SEQUENCE: 12
aaggccagtg agaatgtggg catttatgta tcc                              33

<210> SEQ ID NO 13
<211> LENGTH: 21
<212> TYPE: DNA
<213> ORGANISM: Artificial Sequence
<220> FEATURE:
<223> OTHER INFORMATION: Synthetic

<400> SEQUENCE: 13
ggggcatcca accggtacac t                                           21

<210> SEQ ID NO 14
<211> LENGTH: 27
<212> TYPE: DNA
<213> ORGANISM: Artificial Sequence
<220> FEATURE:
<223> OTHER INFORMATION: Synthetic

<400> SEQUENCE: 14
ggacagagtt acatctatcc attcacg                                     27

<210> SEQ ID NO 15
<211> LENGTH: 357
<212> TYPE: DNA
<213> ORGANISM: Artificial Sequence
<220> FEATURE:
<223> OTHER INFORMATION: Synthetic

<400> SEQUENCE: 15
cagatccagt tggtgcagtc tggacctgag ctgaagaagc ctggagagac agtcaagatc    60
tcctgcaagg cttctgggta taccttcaca aactatggaa tgaactgggt gaagcaggct   120
ccaggaaagg gtttaaagtg gatgggctgg ataaacacct acactggaga gccaacatat   180
gctgatgact tcaagggacg gtttgccttc tctttggaaa cctctgccag cactgcctat   240

```
ttgcagatca acaacctcaa aaatgaggac atggctacat atttctgtgc attacgacga    300
cgcccttact atgctatgga ctactggggt caaggaacct cagtcaccgt ctcctca       357
```

<210> SEQ ID NO 16
<211> LENGTH: 321
<212> TYPE: DNA
<213> ORGANISM: Artificial Sequence
<220> FEATURE:
<223> OTHER INFORMATION: Synthetic

<400> SEQUENCE: 16

```
aacattgtaa tgacccaatc tcccaaatcc atgtccatgt cagtaggaga gagggtcacc     60
ttgagctgca aggccagtga aatgtgggca atttatgtat cctggtatca acagaaacca   120
gagcagtctc ctaaactgct gatatacggg gcatccaacc ggtacactgg ggtccccgat   180
cgcttcacag gcagtggatc tgcaacagat ttcactctga ccatcagcag tgtgcaggct   240
gaagaccttg cagattatca ttgtggacag agttacatct atccattcac gttcggctcg   300
gggacaaagt tggaaataaa a                                              321
```

<210> SEQ ID NO 17
<211> LENGTH: 20
<212> TYPE: DNA
<213> ORGANISM: Artificial Sequence
<220> FEATURE:
<223> OTHER INFORMATION: Synthetic

<400> SEQUENCE: 17

```
ctgcccgagg gcatccgccc                                                 20
```

<210> SEQ ID NO 18
<211> LENGTH: 20
<212> TYPE: DNA
<213> ORGANISM: Artificial Sequence
<220> FEATURE:
<223> OTHER INFORMATION: Synthetic

<400> SEQUENCE: 18

```
gggcggatgc cctcgggcag                                                 20
```

<210> SEQ ID NO 19
<211> LENGTH: 18
<212> TYPE: DNA
<213> ORGANISM: Artificial Sequence
<220> FEATURE:
<223> OTHER INFORMATION: Synthetic

<400> SEQUENCE: 19

```
cagacgacgg cttcaagg                                                   18
```

<210> SEQ ID NO 20
<211> LENGTH: 20
<212> TYPE: DNA
<213> ORGANISM: Artificial Sequence
<220> FEATURE:
<223> OTHER INFORMATION: Synthetic

<400> SEQUENCE: 20

```
aagatcctca cggagtccag                                                 20
```

<210> SEQ ID NO 21
<211> LENGTH: 18
<212> TYPE: DNA
<213> ORGANISM: Artificial Sequence

```
<220> FEATURE:
<223> OTHER INFORMATION: Synthetic

<400> SEQUENCE: 21
gagcctaccc tgccactg                                                 18

<210> SEQ ID NO 22
<211> LENGTH: 21
<212> TYPE: DNA
<213> ORGANISM: Artificial Sequence
<220> FEATURE:
<223> OTHER INFORMATION: Synthetic

<400> SEQUENCE: 22
aggcaaaggc aggttataag g                                             21

<210> SEQ ID NO 23
<211> LENGTH: 19
<212> TYPE: DNA
<213> ORGANISM: Artificial Sequence
<220> FEATURE:
<223> OTHER INFORMATION: Synthetic

<400> SEQUENCE: 23
agccacatcg ctcagacac                                                19

<210> SEQ ID NO 24
<211> LENGTH: 19
<212> TYPE: DNA
<213> ORGANISM: Artificial Sequence
<220> FEATURE:
<223> OTHER INFORMATION: Synthetic

<400> SEQUENCE: 24
gcccaatacg accaaatcc                                                19

<210> SEQ ID NO 25
<211> LENGTH: 25
<212> TYPE: DNA
<213> ORGANISM: Artificial Sequence
<220> FEATURE:
<223> OTHER INFORMATION: Synthetic

<400> SEQUENCE: 25
agugguucuu aacaguucaa caguu                                         25

<210> SEQ ID NO 26
<211> LENGTH: 22
<212> TYPE: DNA
<213> ORGANISM: Artificial Sequence
<220> FEATURE:
<223> OTHER INFORMATION: Synthetic

<400> SEQUENCE: 26
gugaaauguu uaggaccacu ag                                            22
```